United States Patent
Banka et al.

(10) Patent No.: US 8,329,709 B2
(45) Date of Patent: Dec. 11, 2012

(54) 5H-CYCLOPENTA[D]PYRIMIDINES AS AKT PROTEIN KINASE INHIBITORS

(75) Inventors: Anna L. Banka, Boulder, CO (US); Josef R. Bencsik, Boulder, CO (US); James Blake, Boulder, CO (US); Martin Hentemann, Boulder, CO (US); Nicholas C. Kallan, Boulder, CO (US); Jun Liang, South San Francisco, CA (US); Ian S. Mitchell, Boulder, CO (US); Stephen T. Schlachter, Boulder, CO (US); Eli M. Wallace, Boulder, CO (US); Rui Xu, Boulder, CO (US); Tony P. Tang, Boulder, CO (US)

(73) Assignees: Genentech, Inc., South San Francisco, CA (US); Array BioPharma Inc., Boulder, CO (US)

( * ) Notice: Subject to any disclaimer, the term of this patent is extended or adjusted under 35 U.S.C. 154(b) by 0 days.

(21) Appl. No.: 12/812,377

(22) PCT Filed: Jan. 9, 2009

(86) PCT No.: PCT/US2009/030617
§ 371 (c)(1), (2), (4) Date: Jun. 16, 2011

(87) PCT Pub. No.: WO2009/089462
PCT Pub. Date: Jul. 16, 2009

(65) Prior Publication Data
US 2011/0251181 A1 Oct. 13, 2011

Related U.S. Application Data

(60) Provisional application No. 61/020,129, filed on Jan. 9, 2008.

(51) Int. Cl.
*A61K 31/517* (2006.01)
*C07D 239/70* (2006.01)
(52) U.S. Cl. ..................... 514/258.1; 544/253
(58) Field of Classification Search ............... 514/258.1; 544/253
See application file for complete search history.

(56) References Cited

U.S. PATENT DOCUMENTS

| | | | |
|---|---|---|---|
| 8,003,651 B2 | 8/2011 | Mitchell et al. |
| 8,063,050 B2 | 11/2011 | Mitchell et al. |
| 2005/0130954 A1 | 6/2005 | Mitchell et al. |
| 2010/0168123 A1 | 7/2010 | Mitchell et al. |
| 2011/0015204 A1 | 1/2011 | Bencsik et al. |
| 2011/0065716 A1 | 3/2011 | Bencsik et al. |
| 2011/0092479 A1 | 4/2011 | Ahrendt et al. |
| 2011/0160221 A1 | 6/2011 | Bencsik et al. |
| 2011/0245230 A1 | 10/2011 | Mitchell et al. |
| 2011/0269773 A1 | 11/2011 | Mitchell et al. |

FOREIGN PATENT DOCUMENTS

| | | | |
|---|---|---|---|
| WO | WO 2005/051304 A2 | 6/2005 |
| WO | WO 2005/113762 A1 | 12/2005 |
| WO | WO 2008/006040 A1 | 1/2008 |
| WO | WO2008006040 | * | 1/2008 |
| WO | WO2009154207 | * | 12/2008 |

OTHER PUBLICATIONS

Hers, AKT signalling in health and disease, 2011, Cellular Signalling, vol. 23, p. 1515-1527.*
Alessi et al., "Characterization of a 3-phosphoinositide-dependent protein kinase which phosphorylates and activates protein kinase Bα", *Curr. Biol.*, 7, 261-269 (1997).
Balendran et al., "PDK1 acquires PDK2 activity in the presence of a synthetic peptide derived from the carboxyl terminus of PRK2", *Curr. Biol.*, 9, 393-404 (1999).
Bellacosa et al., "Molecular Alterations of the AKT2 Oncogene in Ovarian and Breast Carcinomas", *Int. J. Cancer, (Pred. Oncol.)* 64, 280-285 (1995).
Brodbeck et al., "A Human Protein Kinase Bγ with Regulatory Phosphorylation Sites in the Activation Loop and in the C-terminal Hydrophobic Domain", *J. Biol. Chem.*, 274, No. 14, 9133-9136 (1999).
Brognard et al., "Akt/Protein Kinase B is Constitutively Active in Non-Small Cell Lung Cancer Cells and Promotes Cellular Survival and Resistance to Chemotherapy and Radiation", *Cancer Res.*, 61, 3986-3997 (2001).
Cheng et al., "AKT2, a putative oncogene encoding a member of a subfamily of protein-serine/threonine kinases, is amplified in human ovarian carcinomas", *Proc. Natl. Acad. Sci. USA*, vol. 89, 9267-9271 (1992).
Cheng et al., "Amplification of AKT2 in human pancreatic cancer cells and inhibition of AKT2 expression and tumorigenicity by antisense RNA", *Proc. Natl. Acad. Sci., USA*, vol. 93, 3636-3641 (1996).
Coffer et al., "Molecular cloning and characterization of a novel putative protein-serine kinase related to the cAMP-dependent and protein kinase C families", *Eur. J. Biochem.*, 201, 475-481 (1991).

(Continued)

*Primary Examiner* — Golam M M Shameem
*Assistant Examiner* — Karen Cheng
(74) *Attorney, Agent, or Firm* — Viksnins Harris & Padys PLLP

(57) ABSTRACT

Compounds of Formula I are useful for inhibiting AKT protein kinases. Methods using compounds of Formula I and stereoisomers and pharmaceutically acceptable salts thereof, for in vitro, in situ, and in vivo diagnosis, prevention or treatment of such disorders in mammalian cells, or associated pathological conditions are disclosed. Formula (I).

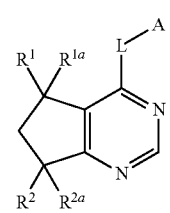

33 Claims, No Drawings

OTHER PUBLICATIONS

Cohen, "Protein kinases—the major drug targets of the twenty-first century?" *Nature Rev. Drug Discovery*, vol. 1, 309-315 (2002).

Delcommenne et al., "Phosphoinositide-3-OH kinase-dependent regulation of glycogen synthase kinase 3 and protein kinase B/AKT by the integrin-linked kinase", *Proc. Natl. Acad. Sci. USA*, vol. 95, 11211-11216 (1998).

Georgakis et al., *Expert Rev. Anticancer Ther. 6 (1)*, pp. 131-140, 2006.

Graff et al., "Increased AKT Activity Contributes to Prostate Cancer Progression by Dramatically Accelerating Prostate Tumor Growth and Diminishing p27Kip1 Expression", *J. Biol. Chem.*, vol. 275, No. 32, 24500-24505 (2000).

Granville et al., *Clin. Cancer Res. 12 (3)*, pp. 679-689, 2006.

Hardie et al., "The Protein Kinase Facts Book. I and II", *Academic Press*, San Diego, CA., 48-56 (1995).

Hass-Kogan et al., "Protein kinase B (PKB/Akt) activity is elevated in glioblastoma cells due to mutation of the tumor suppressor PTEN/MMAC", *Current Biology*, 8, 1195-1198 and Supp. page (1998).

Hay, "The Akt-mTOR tango and its relevance to cancer", *Cancer Cell*, vol. 8, 179-183 (2005).

Hemmings, "Akt Signaling: Linking Membrane Events to Life and Death Decisions", *Science*, vol. 275, 628-630 (1997).

Kim et al., *Current Opinion in Investig. Drugs 6 (12)*, pp. 1250-1258, 2005.

Li et al., "Targeting Serine/Threonine Protein Kinase B/Akt and Cell-cycle Checkpoint Kinases for Treating Cancer", *Current Topics in Med. Chem.*, 2, 939-971 (2002).

Li, Q., "Recent progress in the discovery of Akt inhibitors as anti-cancer agents", *Expert Opinion: Informa Healthcare 17(9)*, pp. 1077-1130, 2007.

Luo et al., *Molecular Cancer Ther. 4 (6)*, pp. 977-986, 2005.

Nakatani et al., "Identification of a Human Akt3 (Protein Kinase B γ) Which Contains the Regulatory Serine Phosphorylation Site", *Biochem. Biophys. Res. Commun.*, 257, 906-910 (1999).

Patent Cooperation Treaty, International Search Report for PCT/US2009/030617, 13 pages, dated May 27, 2009.

Staal, "Molecular cloning of the akt oncogene and its human homologues AKT1 and AKT2: Amplification of AKT1 in a primary human gastric adenocarcinoma", *Proc. Natl. Acad. Sci., USA*, vol. 84, 5034-5037 (1987).

Toker et al., "Akt/Protein Kinase B is Regulated by Autophosphorylation at the Hypothetical PDK-2 Site", *J. Biol. Chem.*, vol. 275, No. 12, 8271-8274 (2000).

Toker et al., "Akt Signaling and Cancer: Surviving but not Moving On", *Cancer Res. 66 (8)*, 3963-3966 (2006).

Zinda et al., "AKT-1, -2, and -3 are Expressed in Both Normal and Tumor Tissues of the Lung, Breast, Prostate, and Colon," *Clin. Cancer Res.*, vol. 7, 2475-2479 (2001).

\* cited by examiner

5H-CYCLOPENTA[D]PYRIMIDINES AS AKT PROTEIN KINASE INHIBITORS

RELATED APPLICATIONS

This application claims priority to U.S. Provisional Application No. 61/020,129 that was filed on Jan. 9, 2008.

BACKGROUND OF THE INVENTION

1. Field of the Invention

The present invention relates to novel inhibitors of serine/threonine protein kinases (e.g., AKT and related kinases), to pharmaceutical compositions comprising the compounds, to a process for making the compounds and to the use of the compounds in therapy. More particularly it relates to certain 4-substituted 5H-cyclopenta[d]pyrimidines useful in the treatment and prevention of hyperproliferative diseases, such as cancer and inflammation, in mammals.

2. Description of the State of the Art

Protein kinases (PK) are enzymes that catalyze the phosphorylation of hydroxy groups on tyrosine, serine and threonine residues of proteins by transfer of the terminal (gamma) phosphate from ATP. Through signal transduction pathways, these enzymes modulate cell growth, differentiation and proliferation, i.e., virtually all aspects of cell life in one way or another depend on PK activity (Hardie, G. and Hanks, S. (1995) *The Protein Kinase Facts Book. I and II*, Academic Press, San Diego, Calif.). Furthermore, abnormal PK activity has been related to a host of disorders, ranging from relatively non-life threatening diseases such as psoriasis to extremely virulent diseases such as glioblastoma (brain cancer). Protein kinases are an important target class for therapeutic modulation (Cohen, P. (2002) Nature Rev. Drug Discovery 1:309).

Significantly, atypical protein phosphorylation and/or expression is often reported to be one of the causative effects of abnormal cellular proliferation, metastasis and cell survival in cancer. The abnormal regulation and/or expression of various kinases, including Akt, VEGF, ILK, ROCK, p70S6K, Bcl, PKA, PKC, Raf, Src, PDK1, ErbB2, MEK, IKK, Cdk, EGFR, BAD, CHK1, CHK2 and GSK3 amongst numerous others, has been specifically implicated in cancer.

Protein kinases include two classes; protein tyrosine kinases (PTK) and serine-threonine kinases (STK). The Protein Kinase B/Akt enzymes are a group of serine/threonine kinases that are overexpressed in a variety of human tumors. One of the best-characterized targets of the PI3K lipid products is the 57 KD serine/threonine protein kinase Akt, downstream of PI3K in the signal transduction pathway (Hemmings, B. A. (1997) Science 275:628; Hay N. (2005) Cancer Cell 8:179-183). Akt is the human homologue of the protooncogene v-akt of the acutely transforming retrovirus AKT8. Due to its high sequence homology to protein kinases A and C, Akt is also called Protein Kinase B (PKB) and Related to A and C(RAC). Three isoforms of Akt are known to exist, namely Akt1, Akt2 and Akt3, which exhibit an overall homology of 80% (Staal, S. P. (1987) Proc. Natl. Acad. Sci. 84:5034; Nakatani, K. (1999) Biochem. Biophys. Res. Commun. 257:906; Li et al (2002) Current Topics in Med. Chem. 2:939-971; WO 2005/113762). The Akt isoforms share a common domain organization that consists of a pleckstrin homology domain at the N-terminus, a kinase catalytic domain, and a short regulatory region at the C-terminus. In addition, both Akt2 and Akt3 exhibit splice variants. Upon recruitment to the cell membrane by PtdInd(3,4,5)$P_3$, Akt is phosphorylated (activated) by PDK1 at T308, T309 and T305 for isoforms Akt1 (PKBα), Akt2 (PKBβ) and Akt3 (PKBγ), respectively, and at S473, S474 and S472 for isoforms Akt1, Akt2 and Akt3, respectively. Such phosphorylation is believed to occur by the mTOR-Rictor complex, although PDK1 (Balendran, A., (1999) Curr. Biol. 9:393), autophosphorylation (Toker, A. (2000) J. Biol. Chem. 275:8271) and integrin-linked kinase (ILK) (Delcommenne, M. (1998) Proc. Natl. Acad. Sci. USA, 95:11211) have been implicated in this process. Akt activation requires its phosphorylation on residue Ser 473 in the C-terminal hydrophobic motif (Brodbeck et al (1999) J. Biol. Chem. 274:9133-9136; Coffer et al (1991) Eur. J. Biochem. 201:475-481; Alessi et al (1997) Curr. Biol. 7:261-269). Although monophosphorylation of Akt activates the kinase, bis(phosphorylation) is required for maximal kinase activity.

Akt is believed to assert its effect on cancer by suppressing apoptosis and enhancing both angiogenesis and proliferation (Toker et al (2006) Cancer Res. 66(8):3963-3966). Akt is overexpressed in many forms of human cancer including, but not limited to, colon (Zinda et al (2001) Clin. Cancer Res. 7:2475), ovarian (Cheng et al (1992) Proc. Natl. Acad. Sci. USA 89:9267), brain (Haas Kogan et al (1998) Curr. Biol. 8:1195), lung (Brognard et al (2001) Cancer Res. 61:3986), pancreatic (Bellacosa et al (1995) Int. J. Cancer 64:280-285; Cheng et al (1996) Proc. Natl. Acad. Sci. 93:3636-3641), prostate (Graff et al (2000) J. Biol. Chem. 275:24500) and gastric carcinomas (Staal et al (1987) Proc. Natl. Acad. Sci. USA 84:5034-5037).

The PI3K/Akt/mammalian target of rapamycin (mTOR) pathway has been explored for targeted small molecule inhibitor therapy (Georgakis, G. and Younes, A. (2006) Expert Rev. Anticancer Ther. 6(1):131-140; Granville et al (2006) Clin. Cancer Res. 12(3):679-689). Inhibition of PI3K/Akt signaling induces apoptosis and inhibits the growth of tumor cells that have elevated Akt levels (Kim et al (2005) Current Opinion in Investig. Drugs 6(12):1250-1258; Luo et al (2005) Molecular Cancer Ther. 4(6):977-986).

The development of kinase inhibitors that target abnormally regulated pathways and ultimately result in disease is of enormous ethical and commercial interest to the medical and pharmaceutical community. A compound that inhibits (1) recruitment of Akt to the cell membrane, (2) activation by PDK1 or PDK2, (3) substrate phosphorylation, or (4) one of the downstream targets of Akt could be a valuable anticancer agent, either as a stand-alone therapy or in conjunction with other accepted procedures.

United States Patent Application Publication 2005/0130954 discloses inter alia, a variety of compounds that act as AKT inhibitors. The compounds are said to be useful in the treatment of hyperproliferative diseases such as cancer.

SUMMARY OF THE INVENTION

In one aspect, the invention relates to compounds that are inhibitors of AKT protein kinases. Accordingly, the compounds of the invention are useful in the treatment of hyperproliferative diseases, such as cancer and inflammation, in mammals.

More specifically, one aspect of the present invention provides compounds of Formula I:

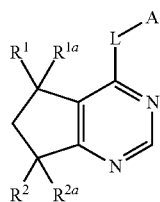

and stereoisomers and pharmaceutically acceptable salts thereof, wherein $R^1$, $R^{1a}$, $R^2$, $R^{2a}$, L and A are as defined herein.

Another aspect of the present invention provides methods of preventing or treating a disease or disorder modulated by AKT, comprising administering to a mammal in need of such treatment an effective amount of a compound of this invention or a stereoisomer or pharmaceutically acceptable salt thereof. Examples of such diseases and disorders include, but are not limited to, hyperproliferative disorders (such as cancer), neurodegeneration, cardiac hypertrophy, pain, migraine and neurotraumatic disease.

Another aspect of the present invention provides methods of preventing or treating cancer, comprising administering to a mammal in need of such treatment an effective amount of a compound of this invention, or a stereoisomer or pharmaceutically acceptable salt thereof, alone or in combination with one or more additional compounds having anti-cancer properties.

In another aspect, the present invention provides a method of inhibiting the production of AKT protein kinases in a mammal, which comprises administering to said mammal a compound of Formula I, or a stereoisomer or pharmaceutically acceptable salt thereof in an amount effective to inhibit production of an AKT protein kinase.

In still yet another aspect, the present invention provides methods of inhibiting the activity of AKT protein kinases, comprising contacting said kinase with a compound of Formula I.

The inventive compounds may be used advantageously in combination with other known therapeutic agents. Accordingly, this invention also provides pharmaceutical compositions comprising a compound of Formula I or a stereoisomer or pharmaceutically acceptable salt thereof, in combination with a second therapeutic agent.

Another aspect of the present invention provides a method of treating a hyperproliferative disease in a mammal comprising administering a therapeutically effective amount of a compound of this invention to the mammal.

Another aspect of the present invention provides the use of a compound of this invention in the manufacture of a medicament for the treatment of a hyperproliferative disease.

Another aspect of the present invention provides compounds of the present invention for use in the treatment of hyperproliferative diseases.

An additional aspect of the invention is the use of a compound of Formula I, or a stereoisomer or pharmaceutically acceptable salt thereof, for therapy. In one embodiment, the therapy comprises the treatment of an AKT protein kinase-mediated condition.

Another aspect of the present invention provides a pharmaceutical composition comprising a compound of the present invention in the treatment of a hyperproliferative disease.

Another aspect of the present invention provides a pharmaceutical composition comprising a compound of the present invention in the treatment of cancer.

Another aspect of the present invention provides a pharmaceutical composition comprising a compound of this invention or a pharmaceutically acceptable salt thereof, and a pharmaceutically acceptable carrier or excipient.

Another aspect of the present invention includes methods of preparing, methods of separation, and methods of purification of the compounds of this invention.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The term "alkyl" includes linear or branched-chain radicals of carbon atoms. Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu") and the like. The abbreviations are sometimes used in conjunction with elemental abbreviations and chemical structures, for example, methanol ("MeOH") or ethanol ("EtOH").

Additional abbreviations used throughout the application include, for example, benzyl ("Bz") and phenyl ("Ph").

The terms "treat" or "treatment" refer to therapeutic, prophylactic, palliative or preventative measures. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrases "therapeutically effective amount" or "effective amount" mean an amount of a compound of the present invention that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer, including melanoma, as well as head and neck cancer.

The phrase "pharmaceutically acceptable" indicates that the substance or composition must be compatible chemically and/or toxicologically, with the other ingredients comprising a formulation, and/or the mammal being treated therewith.

The phrase "pharmaceutically acceptable salt," as used herein, refers to pharmaceutically acceptable organic or inorganic salts of a compound of the invention.

The compounds of this invention also include other salts of such compounds which are not necessarily pharmaceutically acceptable salts, and which may be useful as intermediates for preparing and/or purifying compounds of this invention and/or for separating enantiomers of compounds of this invention.

The term "mammal" means a warm-blooded animal that has or is at risk of developing a disease described herein and includes, but is not limited to, guinea pigs, dogs, cats, rats, mice, hamsters, and primates, including humans.

AKT Inhibitors

The present invention provides compounds, and pharmaceutical formulations thereof, that are potentially useful in the treatment of diseases, conditions and/or disorders modulated by AKT.

One embodiment of this invention provides compounds of Formula I:

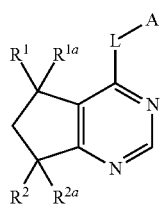

I and stereoisomers and pharmaceutically acceptable salts thereof, wherein:

$R^1$ and $R^{1a}$ are independently selected from hydrogen, methyl, ethyl, —CH=CH$_2$, —CH$_2$OH, CF$_3$, CHF$_2$ or CH$_2$F;

$R^2$ is selected from hydrogen, OH, OCH$_3$ or F;

$R^{2a}$ is selected from hydrogen, methyl or F, or $R^2$ and $R^{2a}$ are oxo;

L is selected from:

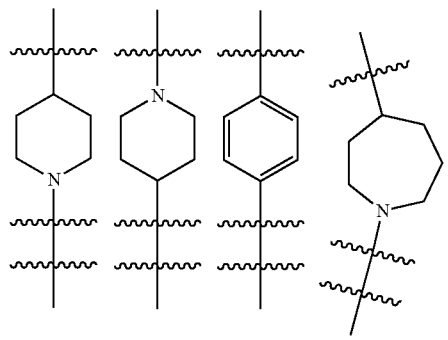

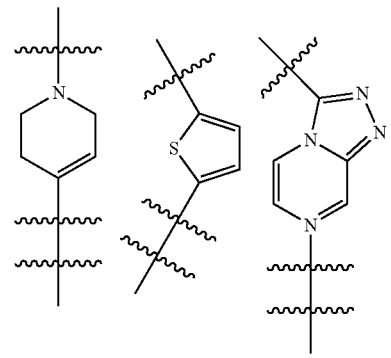

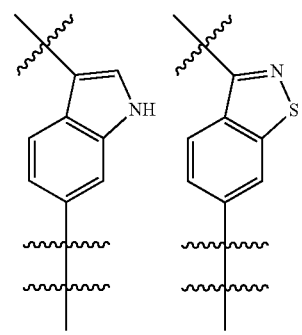

wherein the single wavy line is where L attaches to A and the double wavy line is where L attaches to the pyrimidine;

A is:

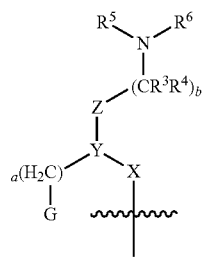

X is a direct bond from L to Y, CH$_2$, O, C=O, NH or C(=O)NH;

Y is CH or N;

Z is absent, CH$_2$ or O, wherein L, X, Y, Z and b are selected so that any nitrogen is not bonded directly to another nitrogen;

G is phenyl optionally substituted with one to four R$^a$ groups or a 5-6 membered heteroaryl optionally substituted by a halogen;

R$^3$ and R$^4$ are independently selected from hydrogen or methyl;

R$^5$ and R$^6$ are independently selected from hydrogen or C$_1$-C$_4$ alkyl;

a is 0 or 1;

b is 0, 1 or 2; and each R$^a$ is independently halogen, C$_1$-C$_6$-alkyl, C$_3$-C$_6$-cycloalkyl, —O—(C$_1$-C$_6$-alkyl), CF$_3$, —OCF$_3$, S(C$_1$-C$_6$-alkyl), CN, —OCH$_2$-phenyl, NH$_2$, —NO$_2$, —NH—(C$_1$-C$_6$-alkyl), —N—(C$_1$-C$_6$-alkyl)$_2$, piperidine, pyrrolidine, CH$_2$F, CHF$_2$, —OCH$_2$F, —OCHF$_2$, —OH, —SO$_2$(C$_1$-C$_6$-alkyl), C(O)NH$_2$, C(O)NH(C$_1$-C$_6$-alkyl), and C(O)N(C$_1$-C$_6$-alkyl)$_2$; or b is 1, R$^3$ is hydrogen and R$^4$ and R$^5$ together with the atoms to which they are attached form an optionally substituted 5-6 membered heterocyclic ring having one ring nitrogen atom, and R$^6$ is selected from the group consisting of hydrogen or C$_1$-C$_4$ alkyl optionally substituted with OH or O(C$_1$-C$_3$ alkyl), such that A has the structre:

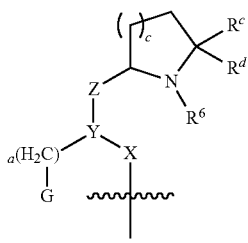

R$^c$ and R$^d$ are independently selected from hydrogen and methyl; and c is 1 or 2; or b is 1, Z is CH$_2$ and R$^5$ and Y together with the atoms to which they are attached form an optionally substituted 6 membered heterocyclic ring having one ring nitrogen atom, and R$^6$ is selected from the group consisting of hydrogen or C$_1$-C$_4$ alkyl optionally substituted with OH or O(C$_1$-C$_3$ alkyl), such that A has the structure:

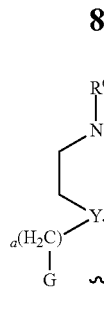

In certain embodiments, R$^1$ is methyl.

In certain embodiments, R$^{1a}$ is hydrogen.

In certain embodiments, R$^2$ is hydrogen.

In certain embodiments, R$^2$ is OH.

In certain embodiments, R$^{2a}$ is hydrogen.

In certain embodiments, Formula I is selected from:

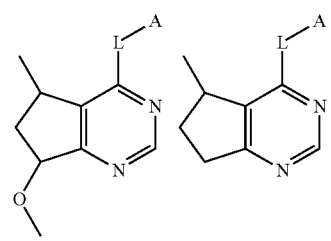

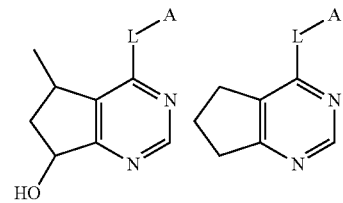

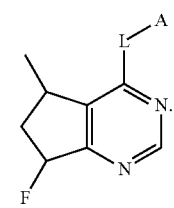

In certain embodiments, Formula I is selected from:

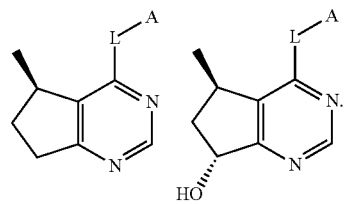

In certain embodiments, L is selected from:

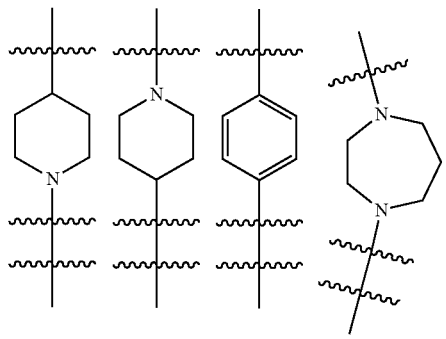

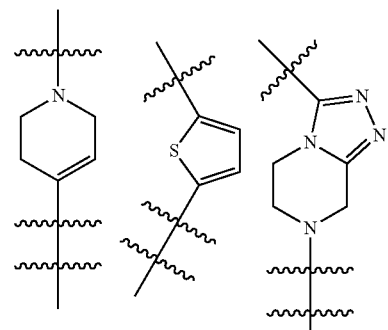

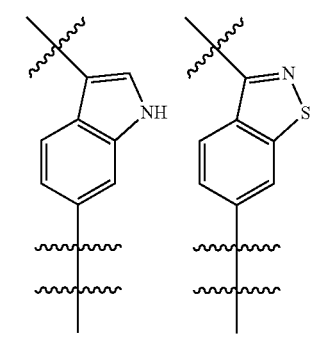

In certain embodiments, L is:

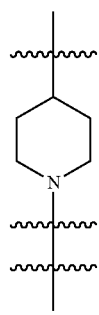

wherein the single wavy line is where L attaches A and the double wavy line is where L attaches to the pyrimidine, providing compounds of Formula Ia having the structure:

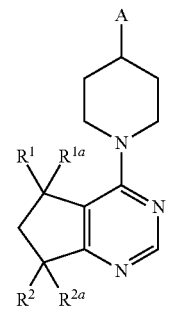

Ia

In certain embodiments, L is:

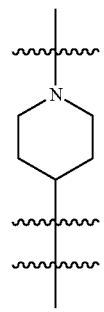

wherein the single wavy line is where L attaches A and the double wavy line is where L attaches to the pyrimidine, providing compounds of Formula Ib having the structure:

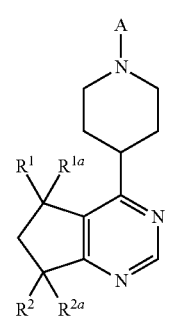

Ib

In certain embodiments, L is:

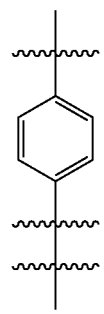

wherein the single wavy line is where L attaches A and the double wavy line is where L attaches to the pyrimidine, providing compounds of Formula Ic having the structure:

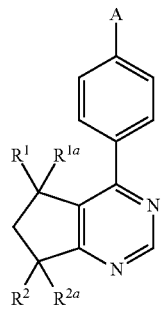

Ic

In certain embodiments, L is:

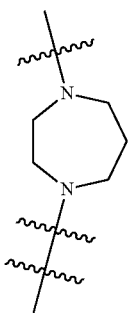

wherein the single wavy line is where L attaches A and the double wavy line is where L attaches to the pyrimidine, providing compounds of Formula Id having the structure:

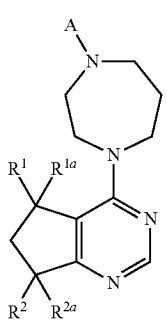

Id

In certain embodiments, L is:

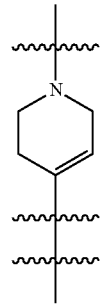

wherein the single wavy line is where L attaches A and the double wavy line is where L attaches to the pyrimidine, providing compounds of Formula Ie having the structure:

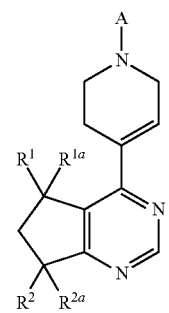

Ie

In certain embodiments, L is:

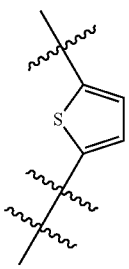

wherein the single wavy line is where L attaches A and the double wavy line is where L attaches to the pyrimidine, providing compounds of Formula If having the structure:

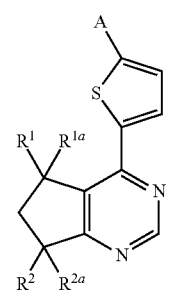

If

In certain embodiments, L is:

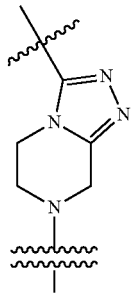

wherein the single wavy line is where L attaches A and the double wavy line is where L attaches to the pyrimidine, providing compounds of Formula Ig having the structure:

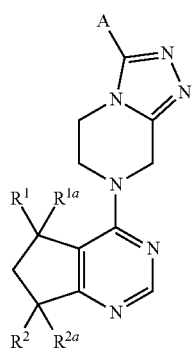

Ig

In certain embodiments, L is:

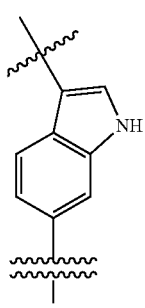

wherein the single wavy line is where L attaches A and the double wavy line is where L attaches to the pyrimidine, providing compounds of Formula Ih having the structure:

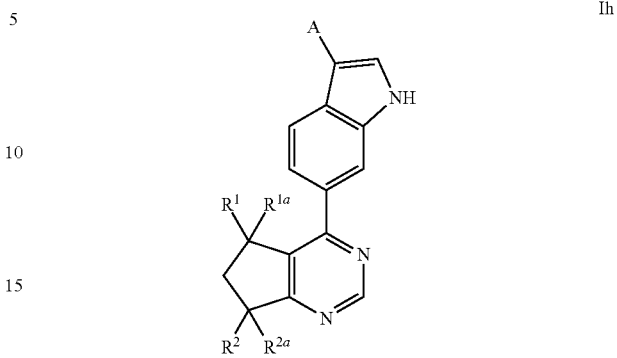

Ih

In certain embodiments, L is:

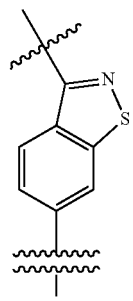

wherein the single wavy line is where L attaches A and the double wavy line is where L attaches to the pyrimidine, providing compounds of Formula Ii having the structure:

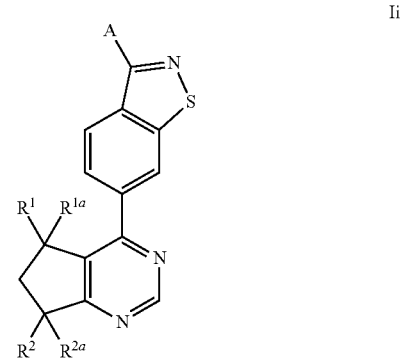

Ii

In certain embodiments, A is:

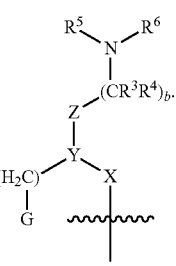

In certain embodiments, X is a direct bond from L to Y, CH$_2$, O, C=O, NH or C(=O)NH.
In certain embodiments, X is a direct bond from L to Y.
In certain embodiments, X is CH$_2$.
In certain embodiments, X is O.
In certain embodiments, X is C=O.
In certain embodiments, X is NH.
In certain embodiments, X is C(=O)NH.
In certain embodiments, Y is CH or N.
In certain embodiments, Y is N.
In certain embodiments, Y is CH.
In certain embodiments, Z is absent, CH$_2$ or O.
In certain embodiments, Z is absent or O.
In certain embodiments, Z is absent.
In certain embodiments, Z is CH$_2$.
In certain embodiments, Z is O.

The compounds of Formula I are such that L, X, Y, Z and b are selected so that any nitrogen is not bonded directly to another nitrogen.

In certain embodiments, X is a direct bond from L to Y, Y is CH$_2$ and Z is O, such that A has the structure A1:

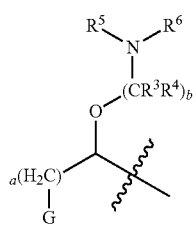

A1

In certain embodiments of A1, a is 0.
In certain embodiments of A1, b is 2.
In certain embodiments of A1, R$^3$ is hydrogen.
In certain embodiments of A1, R$^4$ is hydrogen.
In certain embodiments of A1, R$^5$ is C$_1$-C$_4$ alkyl. In certain embodiments of A1, R$^5$ is methyl.
In certain embodiments of A1, R$^6$ is C$_1$-C$_4$ alkyl. In certain embodiments of A1, R$^6$ is methyl.

In certain embodiments, X is C(=O)NH, Y is CH and Z is absent, such that A has the structure A2:

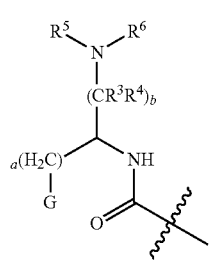

A2

In certain embodiments of A2, a is 1.
In certain embodiments of A2, b is 1.
In certain embodiments of A2, R$^3$ is hydrogen.
In certain embodiments of A2, R$^4$ is hydrogen.
In certain embodiments of A2, R$^5$ is hydrogen.
In certain embodiments of A2, R$^6$ is hydrogen.

In certain embodiments, X is a direct bond from L to Y, Y is CH and Z is absent, such that A has the structure A3:

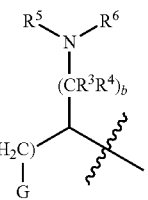

A3

In certain embodiments of A3, a is 0.
In certain embodiments of A3, b is 1.
In certain embodiments of A3, R$^3$ is hydrogen.
In certain embodiments of A3, R$^4$ is hydrogen.
In certain embodiments of A3, R$^5$ is C$_1$-C$_4$ alkyl. In certain embodiments of A3, R$^5$ is isopropyl.
In certain embodiments of A3, R$^6$ is hydrogen.

In certain embodiments, X is a direct bond from L to Y, Y is CH and Z is absent, such that A has the structure A4:

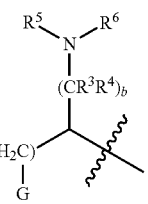

A4

In certain embodiments of A4, a is 0.
In certain embodiments of A4, a is 1.
In certain embodiments of A4, b is 0.
In certain embodiments of A4, b is 1.
In certain embodiments of A4, R$^3$ is hydrogen.
In certain embodiments of A4, R$^4$ is hydrogen.
In certain embodiments of A4, R$^5$ is hydrogen.
In certain embodiments of A4, R$^5$ is C$_1$-C$_4$ alkyl. In certain embodiments of A4, R$^5$ is isopropyl.
In certain embodiments of A4, R$^6$ is hydrogen.

In certain embodiments, X is NH, Y is CH and Z is absent, such that A has the structure A5:

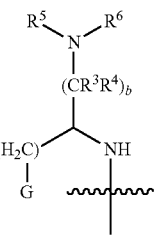

A5

In certain embodiments of A5, a is 0.
In certain embodiments of A5, b is 1.
In certain embodiments of A5, R$^3$ is hydrogen.
In certain embodiments of A5, R$^4$ is hydrogen.
In certain embodiments of A5, R$^5$ is C$_1$-C$_4$ alkyl. In certain embodiments of A5, R$^5$ is isopropyl.
In certain embodiments of A5, R$^6$ is hydrogen.

In certain embodiments, X is C=O, Y is N and Z is absent, such that A has the structure A6:

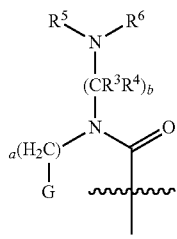

A6

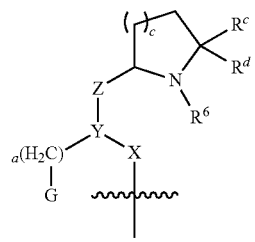

A8

In the embodiments of A6, b must be 1 or 2.
In certain embodiments of A6, a is 1.
In certain embodiments of A6, b is 2.
In certain embodiments of A6, $R^3$ is hydrogen.
In certain embodiments of A6, $R^4$ is hydrogen.
In certain embodiments of A6, $R^5$ is hydrogen.
In certain embodiments of A6, $R^6$ is hydrogen.
In certain embodiments, X is C=O, Y is CH and Z is absent, such that A has the structure A7:

wherein c is 1 or 2, $R^c$ and $R^d$ are independently selected from hydrogen and methyl, and $R^6$ is selected from the group consisting of H or $C_1$-$C_4$ alkyl optionally substituted with OH or O($C_1$-$C_3$ alkyl).

In certain embodiments, c is 1, such that A has the structure A8a:

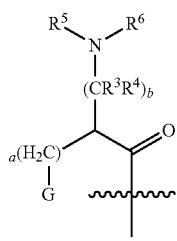

A7

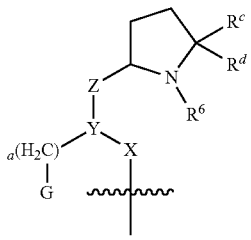

A8a

In certain embodiments of A7, a is 0.
In certain embodiments of A7, b is 1.
In certain embodiments of A7, $R^3$ is hydrogen.
In certain embodiments of A7, $R^4$ is hydrogen.
In certain embodiments of A7, $R^5$ is $C_1$-$C_4$ alkyl. In certain embodiments of A7, $R^5$ is tert-butyl. In certain embodiments of A7, $R^5$ is isopropyl.
In certain embodiments of A7, $R^6$ is hydrogen.
In certain embodiments, $R^3$ is hydrogen.
In certain embodiments, $R^3$ is methyl.
In certain embodiments, $R^4$ is hydrogen.
In certain embodiments, $R^4$ is methy.
In certain embodiments, $R^5$ is hydrogen.
In certain embodiments, $R^5$ is $C_1$-$C_4$ alkyl.
In certain embodiments, $R^5$ is methyl.
In certain embodiments, $R^5$ is isopropyl.
In certain embodiments, $R^5$ is tert-butyl.
In certain embodiments, $R^6$ is hydrogen.
In certain embodiments, $R^6$ is methyl.
In certain embodiments, a is 1.
In certain embodiments, a is 0.
In certain embodiments, b is 0.
In certain embodiments, b is 1.
In certain embodiments, b is 2.
In certain embodiments, Z is O and b is 2.
In certain embodiments, b is 1, $R^3$ is hydrogen and $R^4$ and $R^5$ together with the atoms to which they are attached form an optionally substituted 5-6 membered heterocyclic ring having one ring nitrogen atom, such that A has the structure A8:

In certain embodiments of A8a, X is C=O.
In certain embodiments of A8a, Y is CH.
In certain embodiments of A8a, Z is absent.
In certain embodiments of A8a, a is 0.
In certain embodiments of A8a, $R^c$ is methyl.
In certain embodiments of A8a, $R^d$ is methyl.
In certain embodiments of A8a, $R^6$ is hydrogen.
In certain embodiments, c is 2, such that A has the structure A8b:

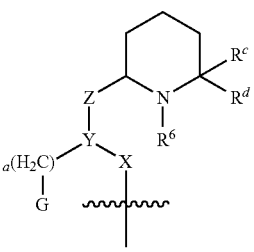

A8b

In certain embodiments, b is 1, Z is $CH_2$ and $R^5$ and Y together with the atoms to which they are attached form an optionally substituted 6 membered heterocyclic ring having one ring nitrogen atom, and $R^6$ is selected from the group consisting of hydrogen or $C_1$-$C_4$ alkyl optionally substituted with OH or O($C_1$-$C_3$ alkyl), such that A has the structure A9:

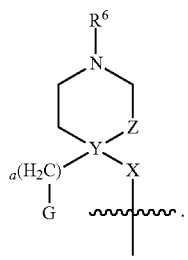

A9

In certain embodiments of Formula A9, X is a direct bond from L to Y.

In certain embodiments of Formula A9, a is 0.

In certain embodiments of Formula A9, $R^6$ is hydrogen.

In certain embodiments, G is phenyl optionally substituted with one to four $R^a$ groups or a 5-6 membered heteroaryl optionally substituted by a halogen.

In certain embodiments, each $R^a$ is independently halogen, $C_1$-$C_6$-alkyl, $C_3$-$C_6$-cycloalkyl, —O—($C_1$-$C_6$-alkyl), $CF_3$, —$OCF_3$, S($C_1$-$C_6$-alkyl), CN, —$OCH_2$-phenyl, $NH_2$, —$NO_2$, —NH—($C_1$-$C_6$-alkyl), —N—($C_1$-$C_6$-alkyl)$_2$, piperidine, pyrrolidine, $CH_2F$, $CHF_2$, —$OCH_2F$, —$OCHF_2$, —OH, —$SO_2$($C_1$-$C_6$-alkyl), C(O)$NH_2$, C(O)NH($C_1$-$C_6$-alkyl), and C(O)N($C_1$-$C_6$-alkyl)$_2$.

Referring to the G group of Formula I, examples include phenyl optionally substituted with one or more $R^a$ groups independently selected from F, Cl, Br, I, methyl, ethyl, isopropyl, tert-butyl, cyclopropyl, CN, $CF_3$, —OMe, —OEt, —$OCF_3$, —$NO_2$, —SMe and —$OCH_2$Ph. Exemplary embodiments of G include phenyl, 2-chlorophenyl, 3-chlorophenyl, 4-chlorophenyl, 4-fluorophenyl, 4-bromophenyl, 4-methylphenyl, 4-ethylphenyl, 4-isopropylphenyl, 4-trifluoromethylphenyl, 4-cyanophenyl, 4-methoxyphenyl, 4-ethoxyphenyl, 4-thiomethylphenyl, 4-trifluoromethoxyphenyl, 4-cyclopropylphenyl, 4-chloro-3-fluorophenyl, 3,4-difluorophenyl, 4-bromo-3-fluorophenyl, 3-fluoro-4-methylphenyl, 3-fluoro-4-methoxyphenyl, 3-fluoro-4-trifluoromethylphenyl, 4-cyano-3-fluorophenyl, 3,4-dichlorophenyl, 2,4-dichlorophenyl, 2,4-difluorophenyl, 2-chloro-4-fluorophenyl, 2-fluoro-4-chlorophenyl, 3,5-dichlorophenyl. 3,5-difluorophenyl, 3-chloro-5-fluorophenyl, 3-chloro-4-fluorophenyl, 3-bromo-4-fluorophenyl, 3,5-difluoro-4-chlorophenyl, 2,3-difluoro-4-chlorophenyl, 2,5-difluoro-4-chlorophenyl, 3,5-difluoro-4-bromophenyl, 2,3-difluoro-4-bromophenyl, 2,5-difluoro-4-bromophenyl, 4-(OCH$_2$Ph)-phenyl, 4-chlorophenyl, 2,4-dichlorophenyl, 3,4-dichlorophenyl, 4-chloro-3-fluorophenyl, 3-chloro-4-fluorophenyl, 3-fluoro-4-bromophenyl, 4-fluorophenyl, 3,4-difluorophenyl, 2,4-difluorophenyl 4-bromophenyl, 4-chloro-2-fluorophenyl, 4-methoxyphenyl, 4-methylphenyl, 4-cyanophenyl, 4-trifluoromethylphenyl, 4-iodophenyl, 4-nitrophenyl, 4-tert-butylphenyl, 2-fluorophenyl, 3-trifluoromethylphenyl, 2-fluoro-4-trifluoromethylphenyl, 3-fluoro-4-trifluoromethoxyphenyl, 3-fluoro-4-trifluoromethylphenyl and 4-trifluoromethoxyphenyl.

In certain embodiments, G is 4-chlorophenyl, 4-bromophenyl, trifluoromethylphenyl or 2,4-dichlorophenyl.

Referring to the G group of Formula I, the phrase "5-6 membered heteroaryl optionally substituted by a halogen" includes thiophenes and pyridines, optionally substituted by halogens. Particular examples include, but are not limited to, the structures:

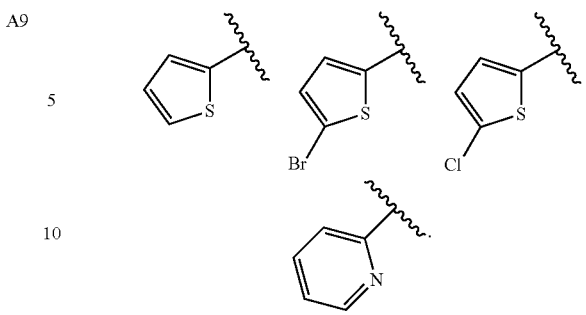

It will be appreciated that certain compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

It will be further appreciated that the compounds of the present invention may exist in unsolvated as well as solvated forms with pharmaceutically acceptable solvents such as water, ethanol, and the like, and it is intended that the invention embrace both solvated and unsolvated forms.

Synthesis of Compounds

Compounds of the present invention may be synthesized by synthetic routes that include processes analogous to those well-known in the chemical arts, particularly in light of the description contained herein. The starting materials are generally available from commercial sources such as Sigma-Aldrich (St. Louis, Mo.), Alfa Aesar (Ward Hill, Mass.), or TCI (Portland, Oreg.), or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database)).

For illustrative purposes, Schemes 1-20 shows a general method for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

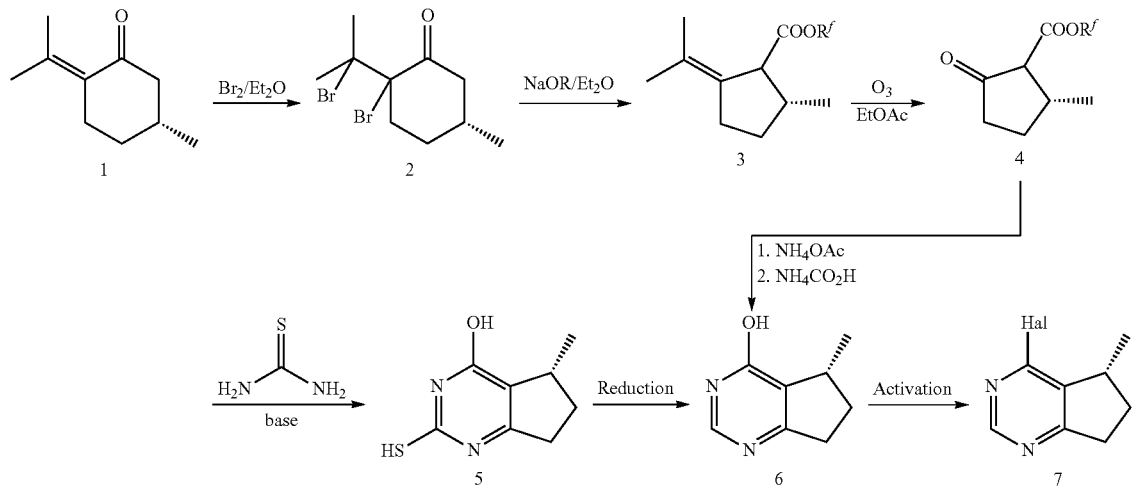

Scheme 1 shows a method of preparing compounds 7, wherein Hal is Br, Cl or I. According to Scheme 1, intermediate 3 can be prepared by brominating (+)-pulegone 1 to provide the di-bromide 2. The di-bromide 2 is then treated with a base, such as sodium ethoxide. Oxidative cleavage (e.g., ozonolysis at −80° C. to −50° C.) of the pulegenate 3, wherein $R^f$ is $C_1$-$C_3$ alkyl, gives the ketoester 4. The pyrimidine ring 5 is constructed by reaction of the ketoester 4 with thiourea in the presence of a base, such as KOH. The mercapto group at the 2-position of compound 5 is eliminated by reduction (e.g., Raney Ni in ammonia) to give compound 6. Alternatively, the ketoester 4 can be converted to the same hydroxypyrimidine 6 by treatment with, for example, an ammonia synthon, such as $NH_4OAc$, followed by treatment with $NH_4CO_2H$ in the presence of formamide at 50° C. to 250° C. and/or at high pressure. Activation of the hydroxypyrimidine 6 (e.g., $POCl_3$) provides the 4-halopyrimidine 7.

Scheme 2 shows a method of preparing compound 11, wherein Hal is Br, Cl or I and $R^1$ and $R^{1a}$ are defined herein. According to Scheme 2, amination of compound 8, wherein $R^g$ is $C_1$-$C_3$ alkyl, using an ammonia synthon (e.g., $NH_4OAc$) gives compound 9. Pyrimidine formation using, for example, ammonium formate in the presence of formamide at 50° C. to 250° C. and/or at high pressure gives the bicyclic unit 10. Activation of compound 10 using, for example, $POCl_3$ or $SOCl_2$ gives the activated pyrimidine 11.

Scheme 3

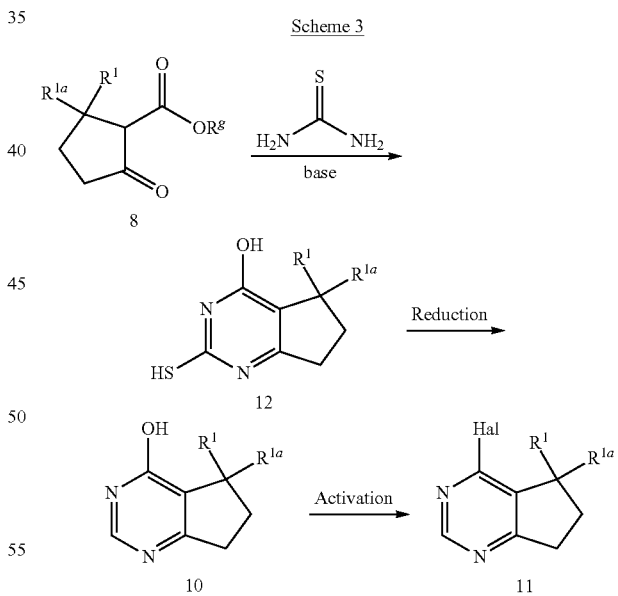

Scheme 2

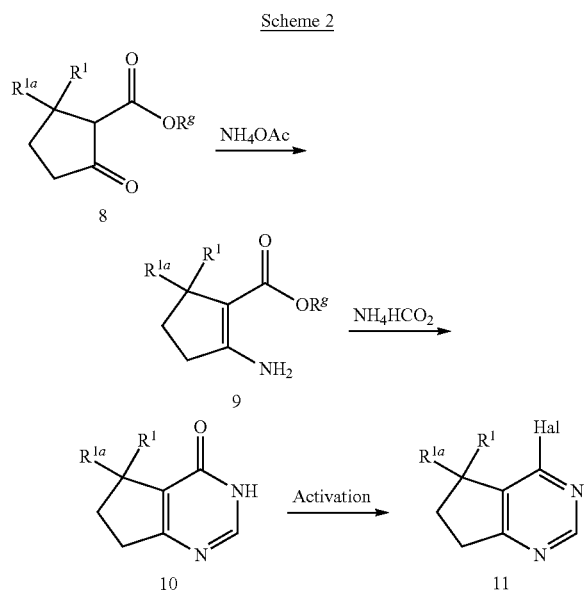

Scheme 3 shows an alternative method of preparing compound 11, wherein Hal is Br, Cl or I and $R^1$ and $R^{1a}$ groups are defined herein. According to Scheme 3, the pyrimidine ring is constructed by reacting the ketoester 8, wherein $R^g$ is $C_1$-$C_3$ alkyl, with thiourea in the presence of a base, such as KOH. The mercapto group at 2-position of compound 12 is eliminated by reduction (e.g., Raney Ni in ammonia) to give 10. Activation of compound 10 using, for example, $POCl_3$ or $SOCl_2$ gives the activated pyrimidine 11.

Scheme 4

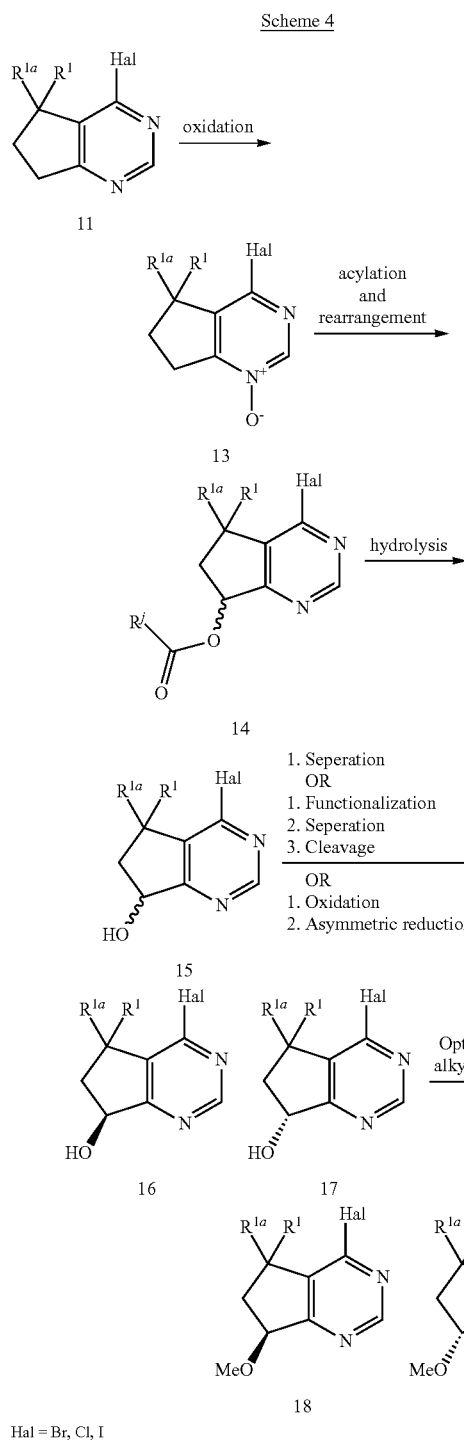

Hal = Br, Cl, I

Scheme 5

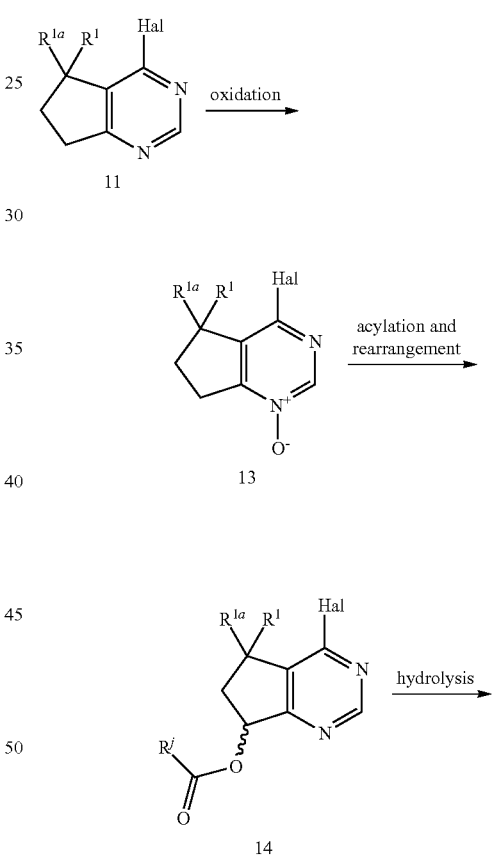

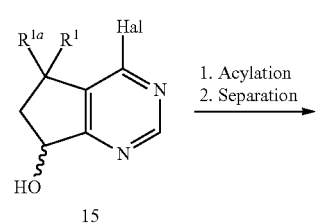

the alcohol 15. Compound 15 is then either: 1) subjected to separation (e.g., chromatography with a chiral or achiral stationary phase); 2) functionalized (e.g., 4-nitrobenzoyl chloride, $NEt_3$) to facilitate separation, separated (e.g., chromatography or recrystallisation) and then hydrolyzed upon treatment with a base, such as lithium hydroxide, in an aqueous/organic solvent mixture at 0° C. to room temperature; or 3) oxidized (e.g., Swern oxidation) followed by an asymmetric reduction (for example, a catalytic chiral catalyst in the presence of hydrogen, the Corey-Bakshi-Shibata catalyst ("CBS catalyst") or a borohydride reducing agent in the presence of a chiral ligand). All alternatives provide a route into the separate diastereomers 16 and 17.

Optionally, the 7-hydroxy group of compounds 16 and 17 may be alkylated with an alkylating reagent, such as an alkyl halide (e.g., MeI), in the presence of a base, such as NaH or KOH, to provide compounds 18 and 19.

Scheme 4 shows a method of preparing compounds 16, 17, 18 and 19, wherein Hal is Br, Cl or I and $R^1$ and $R^{1a}$ are defined herein. According to Scheme 4, oxidation of the 4-halopyrimidine 11 with an oxidizing agent, such as m-chloroperbenzoic acid ("m-CPBA"), Oxone or hydrogen peroxide provides the N-oxide 13. Rearrangement of the N-oxide 13 with acetic anhydride yields the intermediate 14, wherein $R^j$ is methyl if acetic anhydride is used. Compound 14 is then hydrolyzed under mild conditions (e.g., LiOH in an aqueous/organic solvent mixture at 0° C. to room temperature) to give

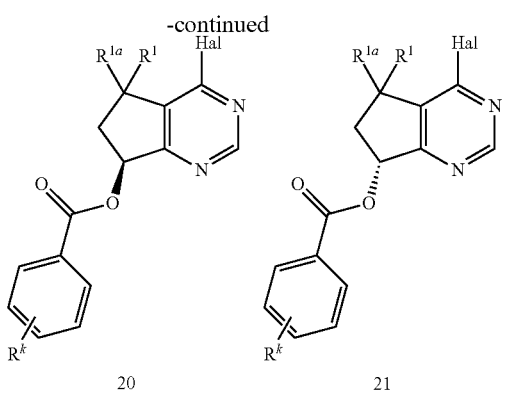

Scheme 5 shows a method of preparing compounds 20 and 21, wherein $R^k$ is halogen or $NO_2$, Hal is Br, Cl or I and $R^1$ and $R^{1a}$ are defined herein. According to Scheme 5, oxidation of the 4-halopyrimidine 11 with an oxidizing agent, such as m-CPBA, Oxone or hydrogen peroxide, provides the N-oxide 13. Rearrangement of the N-oxide 13 with acetic anhydride yields the intermediate 14, wherein $R^1$ is methyl if acetic anhydride is used. Compound 14 is then hydrolyzed under mild conditions (e.g., LiOH in an aqueous/organic solvent mixture at 0° C. to room temperature) to give the alcohol 15. Compound 15 is then functionalized (e.g., 4-nitrobenzoyl chloride or 4-bromobenzoyl chloride in the presence of $NEt_3$ at −20° C. to 50° C.) and separated (e.g., chromatography or recrystallization) to provide a route into the separate, protected diastereomers 20 and 21.

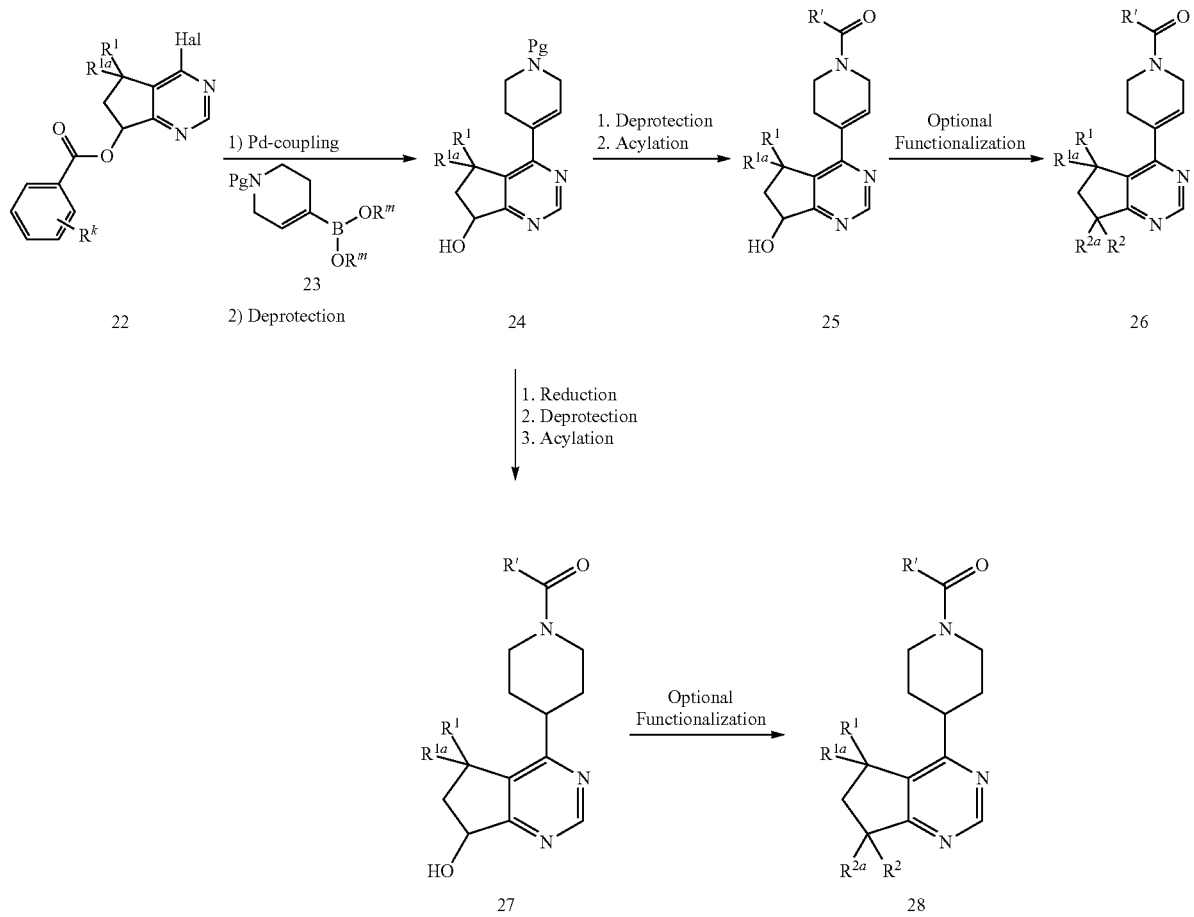

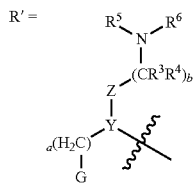

Scheme 6 shows a method for the formation of compounds 26 and 28, wherein $R^1$, $R^{1a}$, $R^2$ and $R^{2a}$ are as defined herein. A Pd-mediated coupling between the halopyrimidine 22, wherein Hal is Br, Cl or I and $R^k$ is halogen or $NO_2$, and an appropriately substituted boronic acid or ester 23, wherein PG is an amine protecting group and $R^m$ is hydrogen or alkyl optionally substituted with OH or the two $R^m$ groups together with the atoms to which they are attached form a 5 or 6 membered ring having one B atom and two O atoms with the remainder carbon atoms, and the ring may be optionally substituted with alkyl groups, using, for example, $Pd(PPh_3)_4$ or $Pd(dppf)Cl_2$ in the presence of $Na_2CO_3$ followed by removal of the benzoate protecting group (e.g., LiOH in an aqueous/organic solvent mixture at 0° C. to 50° C.) gives compound 24. Removal of the amine protecting group (eg. for a Boc group, HCl/dioxane or TFA) and subsequent acylation (eg. HBTU, Hunig's base) gives 25.

Alternatively, optional reduction of the olefin 24 (e.g., $H_2$—Pd/C), followed by the removal of the amine protecting group (e.g., for a Boc group, HCl/dioxane or TFA) and subsequent acylation (e.g., HBTU, Hunig's base) gives 27.

Optional functionalization of the hydroxyl group of compounds 25 or 27 may provide an entry into alternate $R^2$ groups. For example, the alcohol may be converted to a fluoro group, wherein compounds 26 or 28 have $R^2$ as F and $R^{2a}$ as H, by treatment with, for example, DAST. Alternatively, the alcohol of 25 or 27 may be alkylated (e.g., MeI, NaH) to give the methoxy analog, wherein compounds 26 or 28 have $R^2$ as OMe and $R^{2a}$ as H. Alternatively, compounds 25 or 27 may be oxidized (e.g., Swern-like conditions) to provide the ketone, wherein compounds 26 or 28 have $R^2$ and $R^{2a}$ as oxo, which in turn could be treated with a fluorinating agent, such as DAST or Deoxo-Fluor, in an appropriate solvent, such as dichloromethane ("DCM") or chloroform, to give the gem-difluoride analogue, wherein compounds 26 or 28 have $R^2$ as F and $R^{2a}$ as F.

Scheme 7

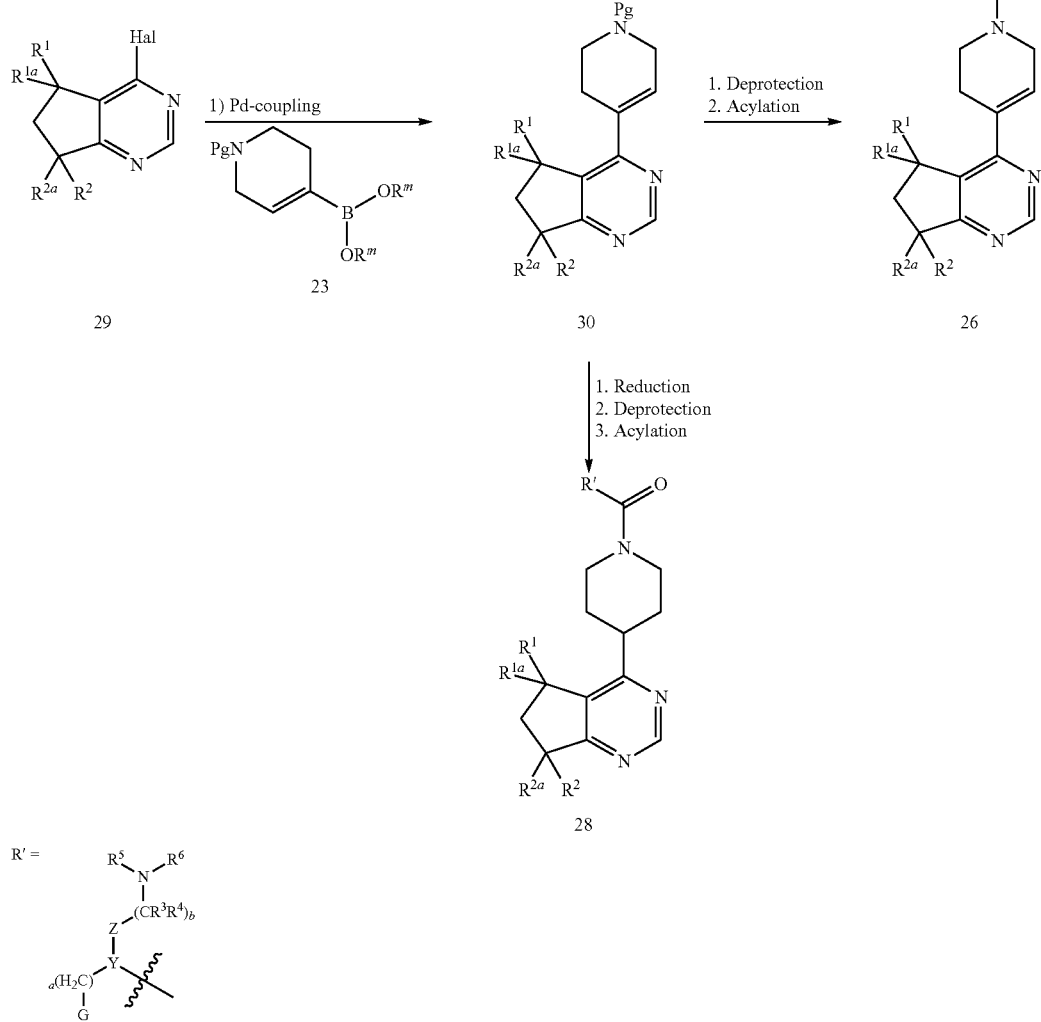

Scheme 7 shows an alternative way to prepare compounds 26 and 28, wherein $R^1$, $R^{1a}$, $R^2$ and $R^{2a}$ are as defined herein. In this scheme, the pyrimidine moieties are functionalized at an earlier stage. A Pd-mediated coupling between the halopyrimidine 29, wherein Hal is Br, Cl or I, and an appropriately substituted boronic acid or ester 23, wherein PG is an amine protecting group and R''' is hydrogen or alkyl optionally substituted with OH or the two R''' groups together with the atoms to which they are attached form a 5 or 6 membered ring having one B atom and two O atoms with the remainder carbon atoms, and the ring may be optionally substituted with alkyl groups, using, for example, Pd(PPh$_3$)$_4$ or Pd(dppf)Cl$_2$ in the presence of Na$_2$CO$_3$, followed by the removal of the benzoate protecting group (e.g., LiOH in an aqueous/organic solvent mixture at 0° C. to 50° C.) gives compound 30.

Removal of the amine protecting group (e.g., for a Boc group, HCl/dioxane or TFA) and subsequent acylation (e.g., HBTU, Hunig's base) gives 26.

Alternatively, optional reduction of the olefin 30 (e.g., H$_2$—Pd/C), followed by the removal of the amine protecting group (e.g., for a Boc group, HCl/dioxane or TFA) and subsequent acylation (e.g., HBTU, Hunig's base) gives compound 28.

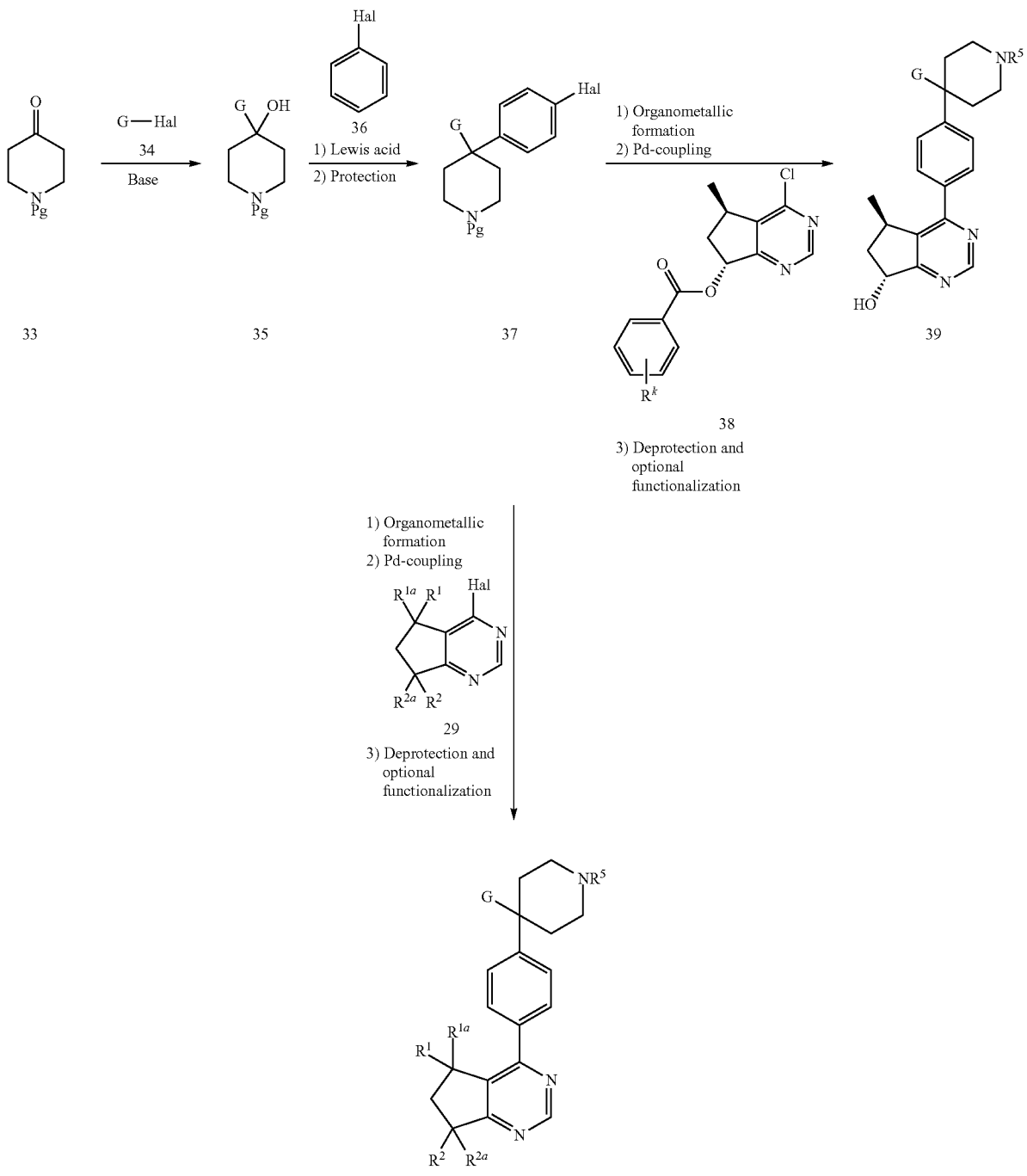

Scheme 8

Scheme 8 shows a method of generating compounds 39 and 40, wherein $R^1$, $R^{1a}$, $R^2$, $R^{2a}$, $R^5$ and G are as defined herein. An appropriately substituted halobenzene 34, wherein Hal is Br, Cl or I, is treated with a strong base, such as BuLi, t-BuLi, Mg, etc., and addition of the newly formed anion into the ketone of compound 33, wherein Pg is an amine protecting group, at −100° C. to 50° C. gives compound 35. Compound 35 is treated with a halobenzene 36, wherein Hal is Br, Cl or I, in the presence of a Lewis acid (e.g., $AlCl_3$ at −20° C. to 100° C.) and reprotection of the amine, if necessary (e.g., $Boc_2O$ for a Boc-group), gives compound 37. Conversion of compound 37 to an appropriate organometallic (e.g., treatment with $Sn_2Me_6$, $Pd(PPh_3)_4$; bispinacol ester boronate, $Pd(dppf)Cl_2$; or Mg) followed by a Pd-mediated coupling with compound 38, wherein $R^k$ is halogen or $NO_2$, using, for example, $PdCl_2(PPh_3)_2$ and aqueous $Na_2CO_3$ in dioxane at room temperature to reflux, and final removal of the amine (e.g., HCl/dioxane for a Boc-group) and the alcohol protecting groups (e.g., LiOH in $THF/H_2O$ at 0° C. to 50° C.) gives compound 39.

Alternatively, a differentially functionalized pyrimidine moiety (e.g., compound 29, wherein Hal is Br, Cl or I) could be used in the same Pd-coupling and deprotection steps to give compound 40.

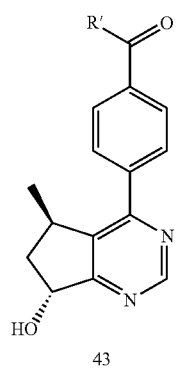

43

R' =

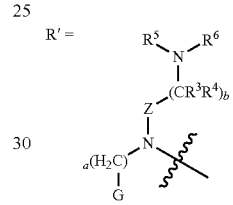

Scheme 9

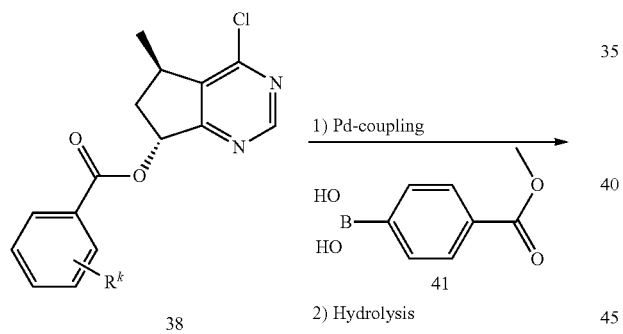

Scheme 9 shows a method of preparing compound 43. A palladium-mediated coupling between compound 38, wherein $R^k$ is halogen or $NO_2$, and compound 41 using, for example, $PdCl_2(dppf)$ and aqueous $Na_2CO_3$ in dioxane at room temperature to reflux, followed by saponification of the esters (e.g., LiOH or NaOH in THF/water at 0° C. to reflux) gives compound 42. The newly formed acid is treated with an appropriately substituted primary or secondary amine under standard coupling conditions (e.g., HBTU/DIPEA/DMF) to give compound 43.

Scheme 10

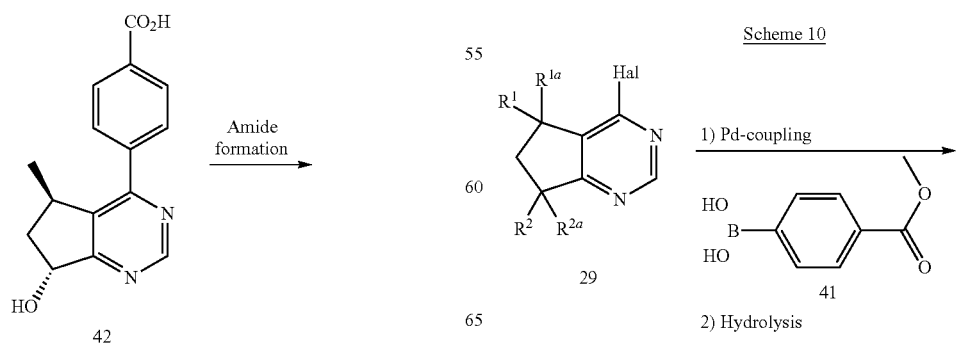

-continued

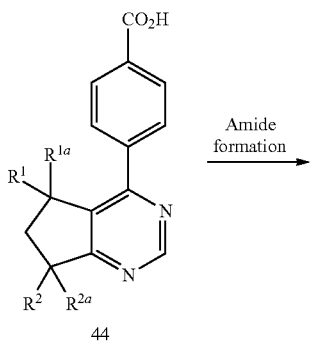

44

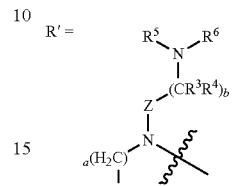

R' =

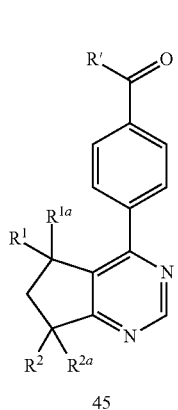

45

Scheme 10 shows a means of preparing compound 45, wherein $R^1$, $R^{1a}$, $R^2$ and $R^{2a}$ are as defined herein, with a differently substituted pyrimidine moiety. A palladium-mediated coupling between compound 29, wherein Hal is Br, Cl or I, and compound 41 using, for example, $PdCl_2(dppf)$ and aqueous $Na_2CO_3$ in dioxane at room temperature to reflux, followed by saponification of the ester (e.g., LiOH or NaOH in THF/water at 0° C. to reflux) gives compound 44. Treatment of the newly formed acid with an appropriately substituted primary or secondary amine under standard coupling conditions (e.g., HBTU/DIPEA/DMF) gives compound 45.

Scheme 11

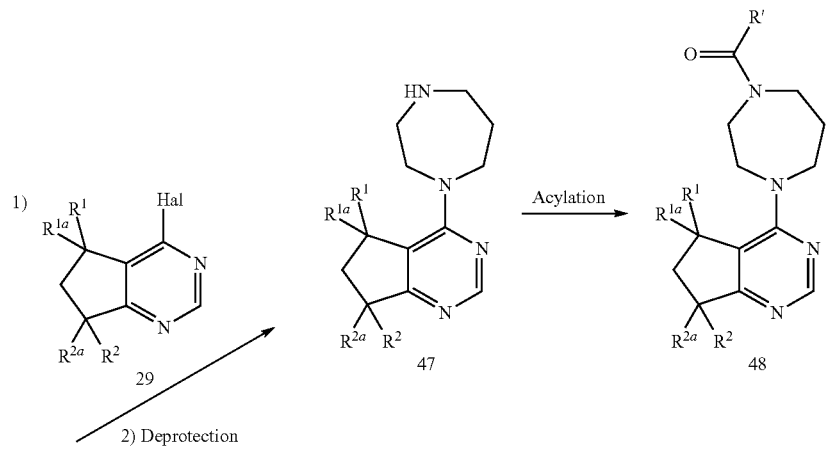

-continued

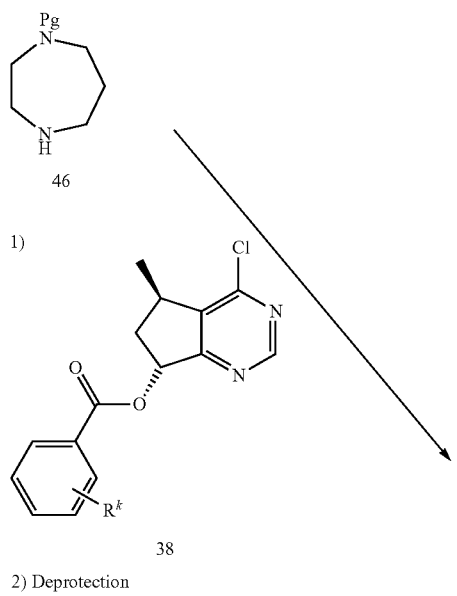

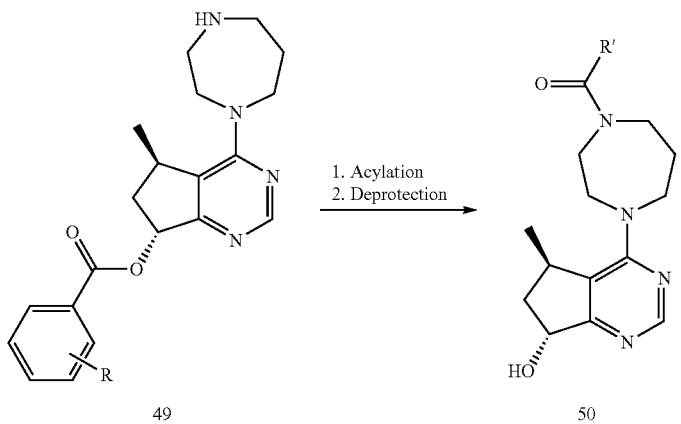

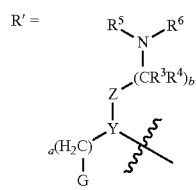

Scheme 11 shows a means of generating compounds 48 and 50, wherein $R^1$, $R^2$ and $R^{2a}$ are as defined herein. An appropriately mono-substituted diazepine 46, wherein PG is an amine protecting group, is treated with compound 29, wherein Hal is Br, Cl or I, and a tertiary amine base (e.g., Hunig's base) in a suitable solvent (e.g., isopropanol) at room temperature to reflux, followed by removal of the amine protecting group, using, for example, in the case of a Boc-group, TFA or HCl/dioxane at 0° C. to room temperature to give compound 47. Treatment of compound 47 with an appropriately substituted acid using standard amide forming conditions (e.g., HBTU/DIPEA/DCM at 0° C. to reflux) gives compound 48.

Alternatively, an appropriately mono-substituted diazepine 46 is treated with compound 38, wherein $R^k$ is halogen or $NO_2$, and a tertiary amine base (e.g., Hunig's base) in a suitable solvent (e.g., isopropanol) at room temperature to reflux, followed by removal of the amine protecting group, using, for example, in the case of a Boc-group, TFA or HCl/dioxane at 0° C. to room temperature to give compound 49. Compound 49 is treated with an appropriately substituted acid using standard amide forming conditions (e.g., HBTU/DIPEA/DCM at 0° C. to reflux) followed by saponification of the ester (e.g., LiOH or NaOH in THF/water at 0° C. to reflux) gives compound 50.

Scheme 12

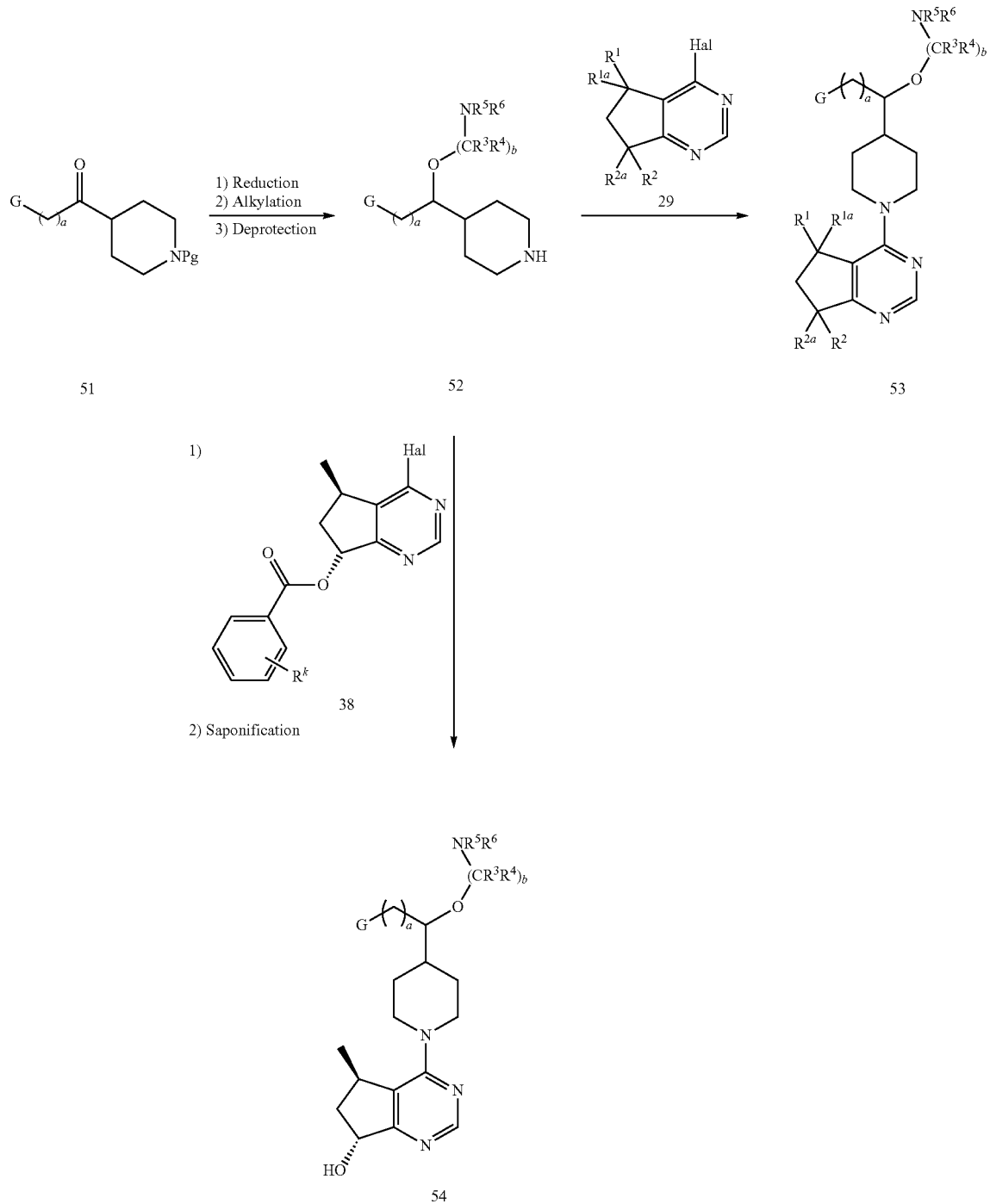

Scheme 12 shows a method for the formation of compounds 53 and 54, wherein $R^1$, $R^{1a}$, $R^2$, $R^{2a}$, $R^3$, $R^4$, $R^5$, $R^6$, G, a and b are as defined herein. Compound 51, wherein PG is an amine protecting group, is reduced using, for example, $NaBH_4$ in EtOH at 0° C. to 50° C. The resulting alcohol is then alkylated with an appropriate amine-containing side chain (e.g., $N(CH_3)_2CH_2CH_2Cl$) using, for example, a base such as NaH in DMF at room temperature to 100° C. This is followed by deprotection of the piperidine amine using, for example, in the case of Boc, HCl/dioxane or TFA at 0° C. to room temperature, gives compound 52. Compound 52 may then be treated with the halopyrimidine 29, wherein Hal is Br, Cl or I, and a tertiary amine base (e.g., Hunig's base) in, for example, DMF at room temperature to 140° C. to give compound 53.

Alternatively, compound 52 may be treated with compound 38, wherein Hal is Br, Cl or I and $R^k$ is halogen or $NO_2$, under similar conditions, followed by saponification of the benzoyl group using, for example, LiOH in THF/water at 0° C. to reflux to give compound 54.

Scheme 13

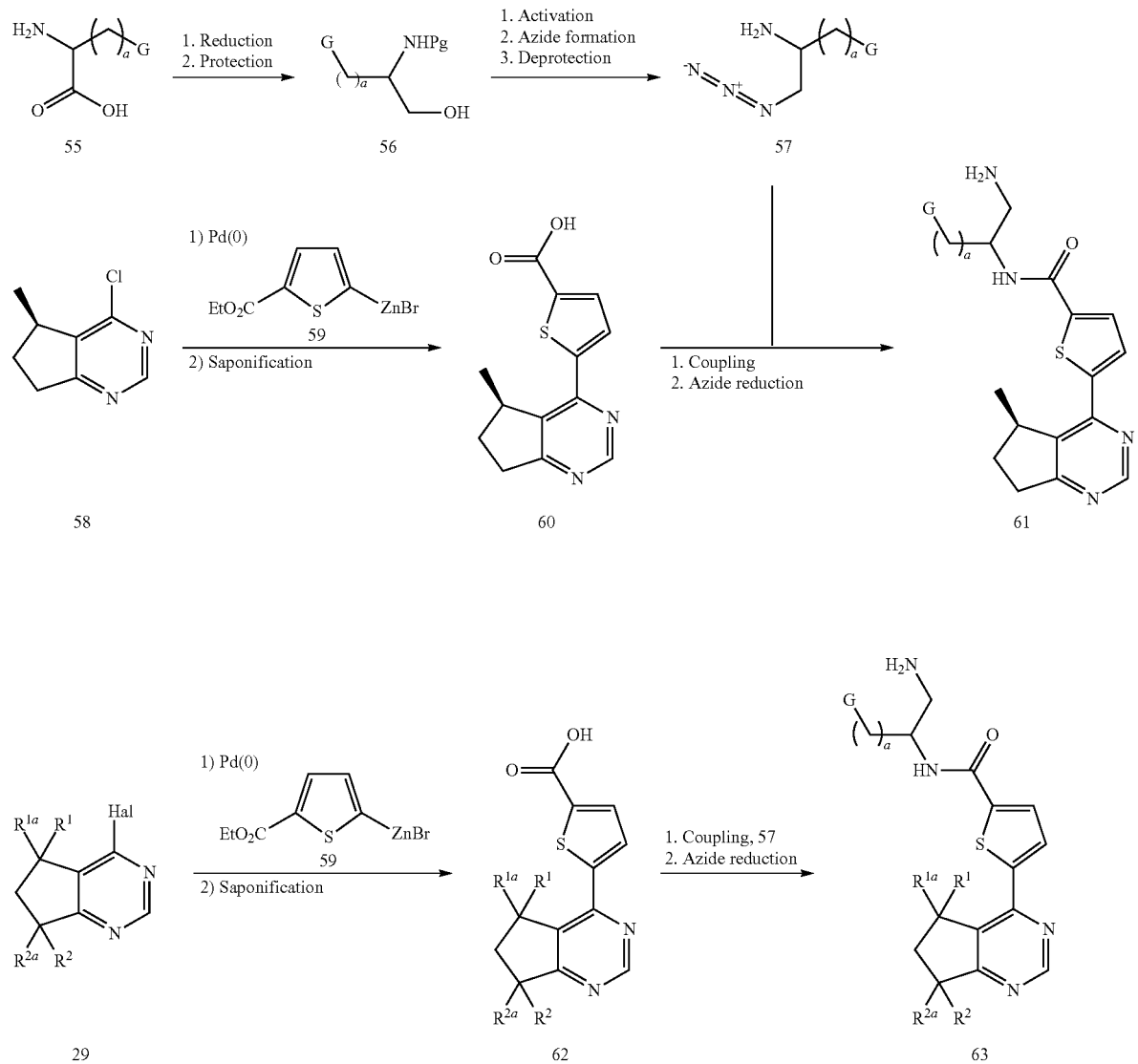

Scheme 13 describes a route to prepare compound 61, wherein G and a are as defined herein. The amino acid 55 is reduced using, for example, LiBH$_4$ and ClSi(CH$_3$)$_3$ in THF at 0° C. to room temperature, followed by protection of the amine, for example, using Boc$_2$O, if Pg is Boc, to give compound 56, wherein PG is an amine protecting group. Activation of the alcohol 56 using, for example, methanesulphonyl chloride and triethylamine in DCM at −20° C. to room temperature, followed by displacement with a protected amine, such as azide (using, for example, sodium azide in DMF at room temperature to 120° C.) and deprotection of the amine (for example, using HCl/dioxane or TFA for a Boc group) can give the aminoazide 57. Compound 60 may be prepared by a palladium mediated coupling between the organozinc 59 and the chloropyrimidine 58 using, for example, Pd(PPh$_3$)$_4$ in THF at room temperature to reflux, followed by saponification of the ester to give the acid 60. Coupling of the acid 60 and the amine 57 under standard conditions (e.g., HBTU/ Hunig's base) and reduction of the azide (e.g., H$_2$—Pd/C or PPh$_3$) can give compound 61.

Alternatively, instead of the chloropyrimidine 58, an alternatively substituted pyrimidine 29, wherein Hal is Br, Cl or I and R$^1$, R$^{1a}$, R$^2$ and R$^{2a}$ are as defined herein, may be used using similar procedures to above, followed by saponification, to give compound 62. A similar coupling with the amine 57 and azide reduction then gives compound 63.

Scheme 14

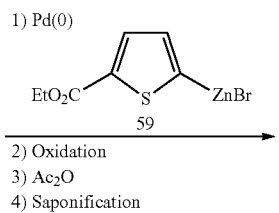

-continued

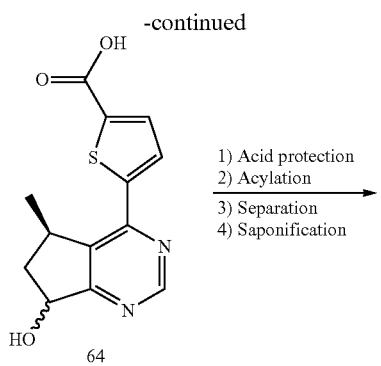

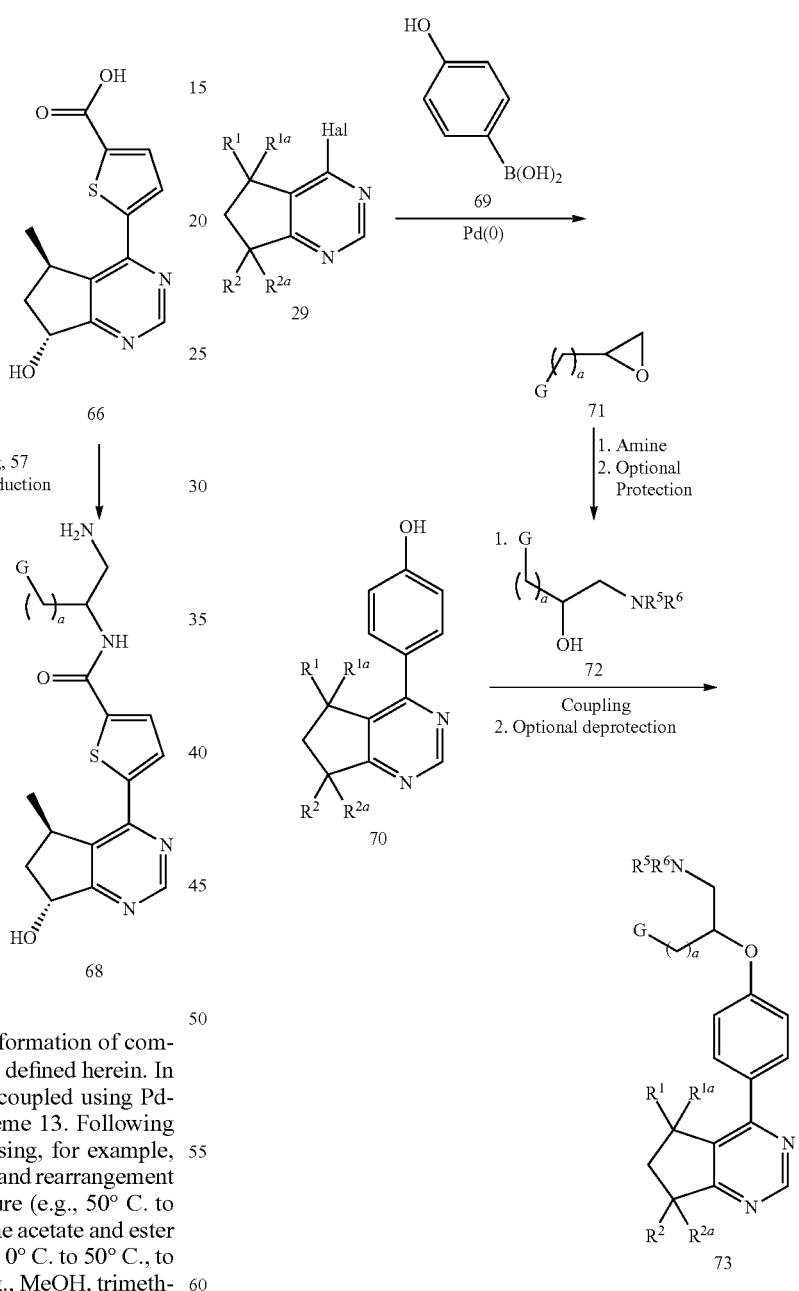

coupled with the aminoazide 57 using standard amide forming conditions (e.g., HBTU, Hunig's base, DCM at −20° C. to reflux), followed by reduction of the azide (e.g., H$_2$—Pd/C or PPh$_3$) to give compounds 67 and 68.

Optionally substituted forms of compounds 67 and 68 may be prepared by replacing the chloropyrimidine 58 in Scheme 14, with the optionally substituted halopyrimidine 11, or by performing the transformations described in Scheme 17.

Scheme 14 describes a method for the formation of compounds 67 and 68, wherein G and a are as defined herein. In this example, compounds 58 and 59 are coupled using Pd-mediated conditions as described in Scheme 13. Following this, the pyrimidine-1-oxide is formed, using, for example, m-CPBA or Oxone, followed by acylation and rearrangement with acetic anhydride at higher temperature (e.g., 50° C. to reflux) and subsequent saponification of the acetate and ester using, for example, LiOH in THF/water at 0° C. to 50° C., to give the acid 64. Protection of the acid (e.g., MeOH, trimethylsilyldiazomethane at −20° C. to room temperature) as the methyl ester, followed by acylation of the alcohol (e.g., p-nitrobenzoyl chloride, NEt$_3$ in DCM at −20° C. to reflux) to facilitate separation, separation (e.g. chromatography or recrystallization) and saponification of the benzoate and methyl esters (using, for example, LiOH in THF/water at 0° C. to 50° C.) gives both compounds 65 and 66. These may be Scheme 15 describes the preparation of compounds 73, wherein $R^1$, $R^{1a}$, $R^2$, $R^{2a}$, $R^5$, $R^6$, G and a are as defined herein. A Pd-mediated reaction between the halopyrimidine 29, wherein Hal is Br, Cl or I, and the boronic acid 69 using, for example, PdCl$_2$(PPh$_3$)$_2$ and aqueous Na$_2$CO$_3$ in isopropanol at room temperature to reflux, gives the phenol 70.

Compound 72 is prepared by the amine-mediated opening of epoxide 71, followed by amine protection (e.g., Boc$_2$O) if the resulting amine is primary or secondary. Coupling of compound 72 to compound 70 under, for example, Mitsunobu conditions (e.g., diethylazodicarboxylate and PPh$_3$ at −40° to 5° C., followed by warming to temperatures up to 50° C.) and optional deprotection, if required (e.g., HCl/dioxane or TFA for a Boc-group), gives compound 73.

Scheme 16

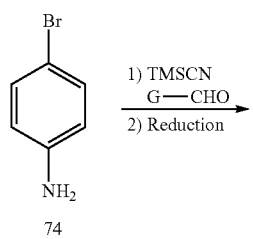

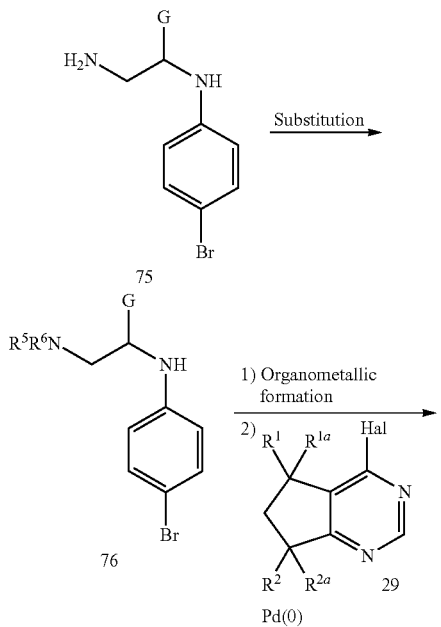

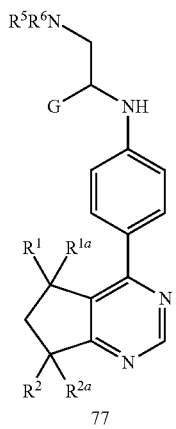

Scheme 16 describes the preparation of compounds 77, wherein $R^1$, $R^{1a}$, $R^2$, $R^{2a}$, $R^5$, $R^6$ and G are as defined herein. The aniline 74 is treated with TMS-CN and an aldehyde in the presence of an acid, such as sulphamic acid, in a protic solvent, such as MeOH, at 0° C. to 50° C., followed by reduction of the resulting nitrile, using, for example, LiAlH$_4$ at −78° C. to room temperature in THF, gives compound 75. Alkylation of the amine (e.g., alkyl halide and base, such as NaH) or reductive amination using a suitable aldehyde or ketone in the presence of a reducing agent, such as sodium triacetoxyborohydride, at 0° C. to 50° C. gives compound 76. Compound 76 may then be converted to an appropriate organometallic reagent by treatment with, for example, a borane, PdCl$_2$ (dppf) and KOAc in DMSO, Sn$_2$(CH$_3$)$_6$ and Pd(PPh$_3$)$_4$ or alternatively an activated form of Mg or Zn. This organometallic reagent may then be coupled to the halopyrimidine 29, wherein Hal is Br, Cl or I, using a palladium-mediated reaction (e.g., Pd(PPh$_3$)$_4$ and aqueous Na$_2$CO$_3$ in, for example, isopropanol at room temperature to reflux) gives compound 77.

Scheme 17

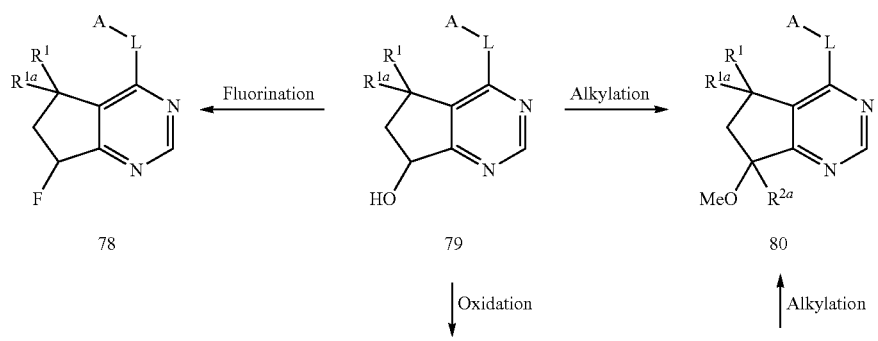

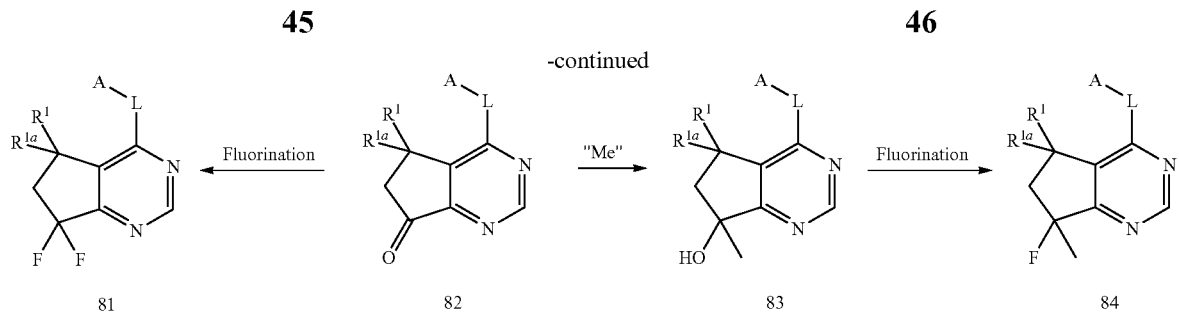

Scheme 17 shows a general method for the functionalization of the hydroxyl group of compound 79, wherein A, L, $R^1$ and $R^{1a}$ are as defined herein, providing alternative $R^2$ and $R^{2a}$ groups. The alcohol 79 may be converted to a fluoro-group 78 by treatment with a fluorinating agent such as, for example, DAST. Alternatively, the alcohol 79 may be alkylated (e.g., a methylating agent such as MeI and a strong base, such as NaI) to give the methoxy analog 80 (in this instance, $R^{2a}$ is hydrogen). Alternatively, compound 79 may be oxidized (e.g., Swern-like conditions) to provide the ketone 82, which in turn could be treated with a fluorinating agent, such as DAST or Deoxo-Fluor, in an appropriate solvent, such as DCM or chloroform, to give the gem-difluoro analogue 81. Ketone 82 could also be treated with an appropriate organo-metallic nucleophile, such as MeMgBr or MeLi, to generate the tertiary alcohol 83. This may be further fluorinated or methylated as described above to give compounds 84 and 80 (in this instance, $R^{2a}$ is methyl), respectively. Scheme 17 will generally apply to compounds of Formula I and intermediates thereof, wherein $R^2$ is OH and $R^{2a}$ is hydrogen.

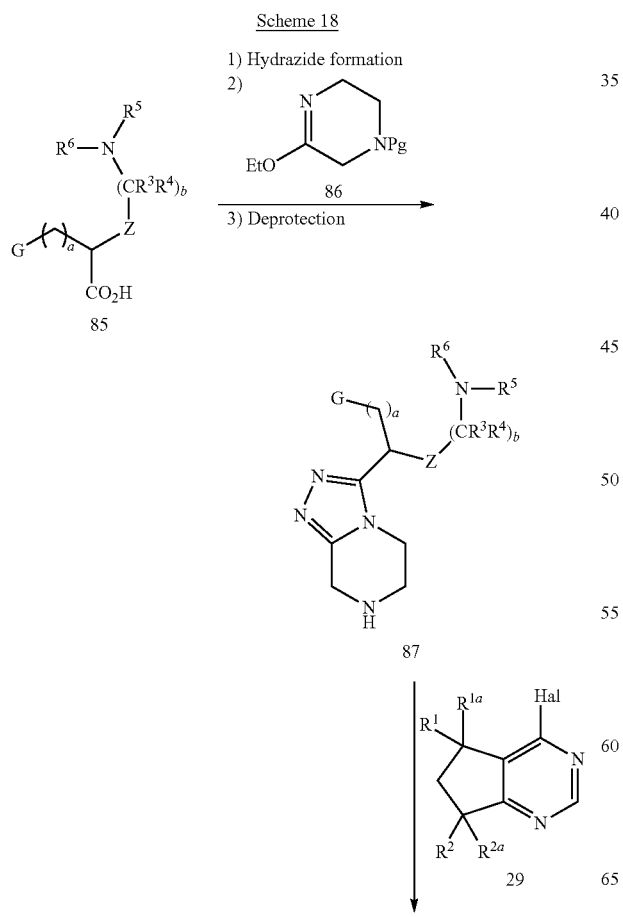

Scheme 18 describes a process for preparing compound 88, wherein $R^1$, $R^{1a}$, $R^2$, $R^{2a}$, $R^3$, $R^4$, $R^5$, $R^6$, G, Z, a, and b are as defined herein. The acid 85 is converted to the hydrazide by treatment with, for example, hydrazine under standard amide coupling conditions (e.g., 1,1-carbonyldiimidazole), followed by condensation with compound 86, wherein PG is an amine protecting group, at room temperature to 150° C. and removal of the protecting group (e.g., if Pg is Boc, the use of HCl/dioxane or TFA) to give compound 87. Compound 87 is treated with compound 29, wherein Hal is Br, Cl or I, in the presence of a base (e.g., $NEt_3$, Hunig's base, etc.) at room temperature to 200° C., optionally in a sealed container with or without microwave assistance, can give compound 88.

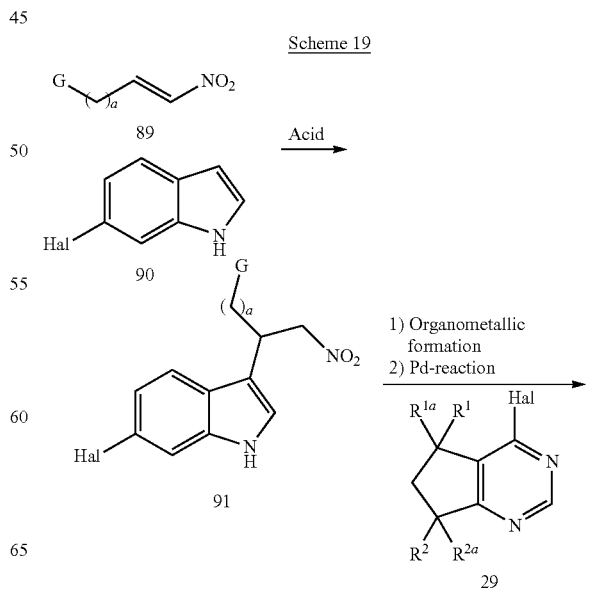

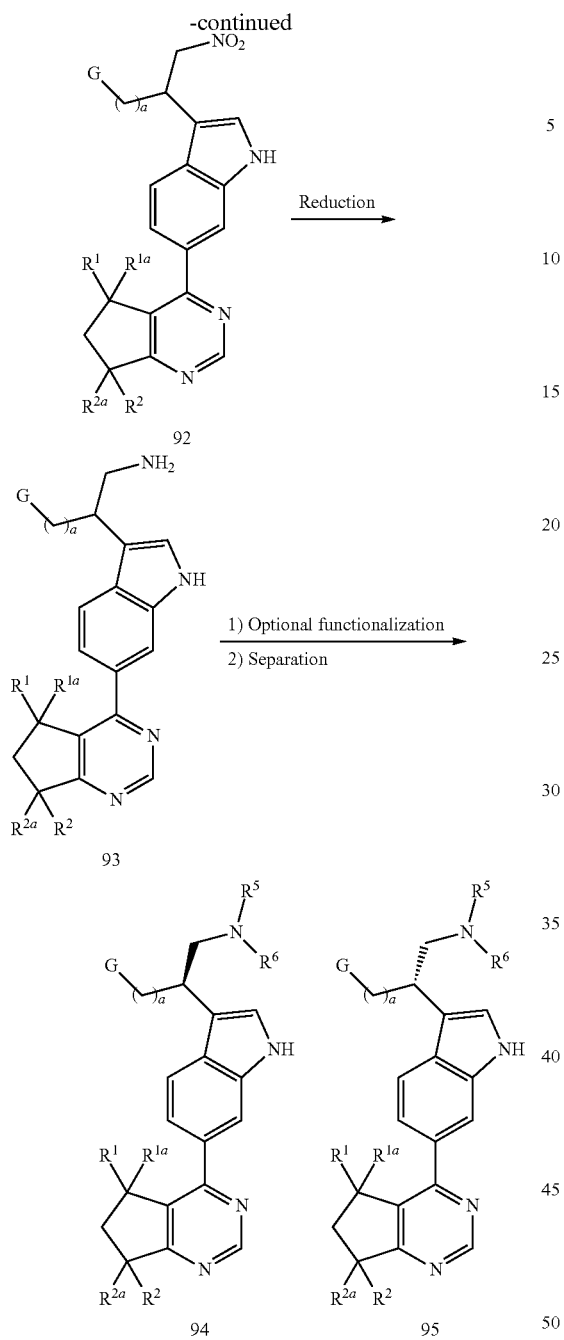

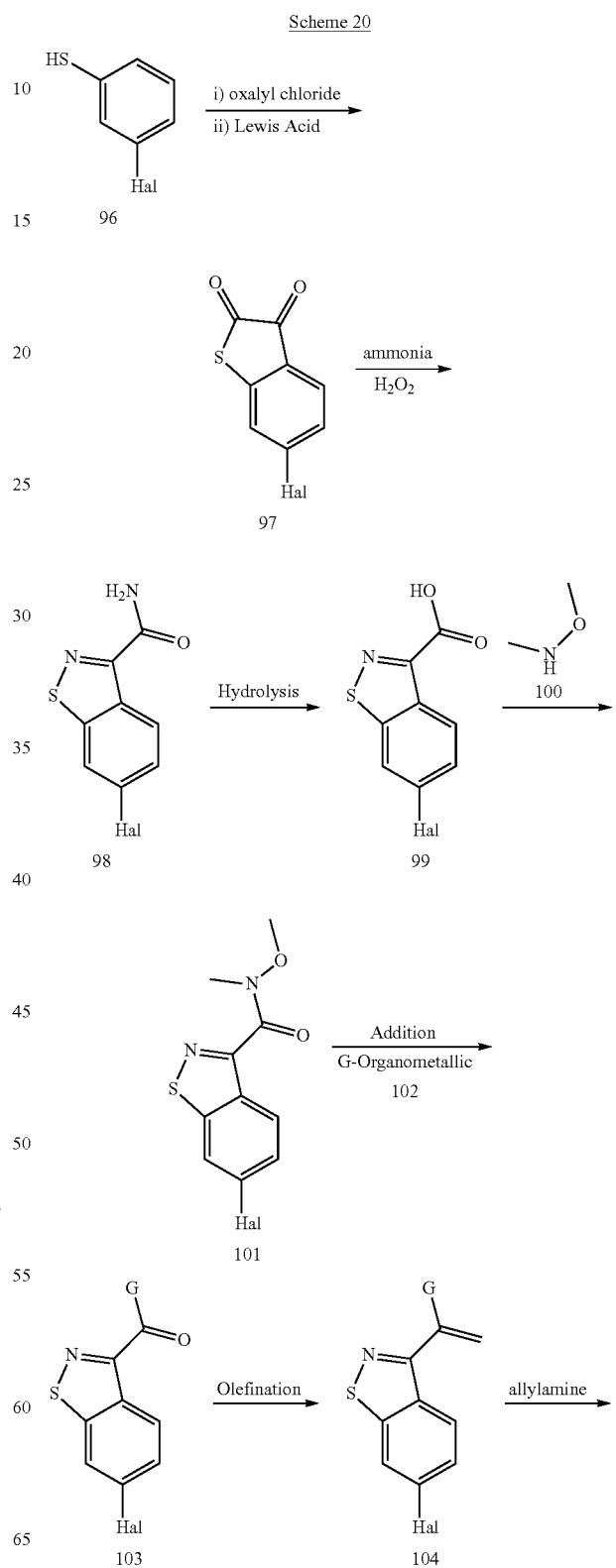

primary amine 93. Optional functionalization of this amine (e.g., reductive amination, alkylation, etc.) followed by separation of the two diastereomers then gives compounds 94 and 95.

Scheme 19 shows a general scheme for the synthesis of compounds 94 and 95, wherein $R^1$, $R^{1a}$, $R^2$, $R^{2a}$, $R^5$, $R^6$, G and a are as defined herein. A Michael reaction between compounds 89 and 90, wherein Hal is Br, Cl or I, in the presence of an acid (e.g., a protic acid such as catalytic, concentrated $H_2SO_4$) gives compound 91. This haloindole 91 may be converted to an organometallic (e.g., treatment with $Sn_2(CH_3)_6$, $Pd(PPh_3)_4$; bispinacol ester boronate, Pd(dppf) $Cl_2$; or activated Mg) followed by a Pd-mediated coupling with compound 29 using, for example, $PdCl_2(PPh_3)_2$ and aqueous $Na_2CO_3$ in dioxane at room temperature to reflux for a Suzuki coupling, or $Ph(PPh_3)_4$ in toluene at room temperature to reflux for a Stille coupling, gives compound 92. Reduction of the nitro group in 92 using, for example, Fe/AcOH or hydrogenation under a $PtO_2$ catalyst gives the

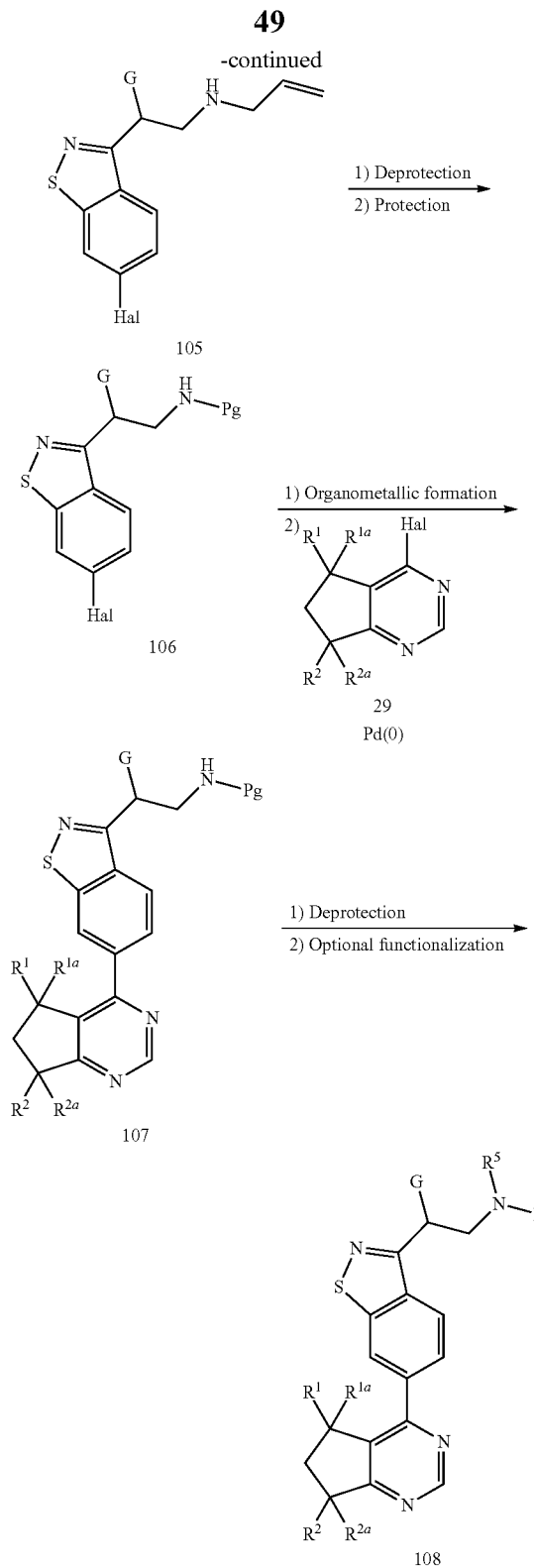

Scheme 20 describes the preparation of compound 108, wherein $R^1$, $R^{1a}$, $R^2$, $R^{2a}$, $R^5$, $R^6$ and G are as defined herein. Acylation of 96, wherein Hal is Br, Cl or I, with oxalyl chloride, followed by treatment of the resulting acid chloride with a Lewis acid, such as $AlCl_3$, gives compound 97, which may then be treated with aqueous ammonium hydroxide and an oxidant, such as hydrogen peroxide, to afford the primary amide 98. Hydrolysis of amide 98 with a base, for example, NaOH, yields carboxylic acid 99 (a procedure is described in J. Med. Chem., 37, 2308-2314 (1994)). Compound 99 is coupled with N,O-dimethylhydroxylamine under standard coupling conditions (e.g., HBTU, DIEA) to produce the amide 101. Compound 101 can react with compound 102, which is a Grignard reagent, zinc or a lithium anion, to produce the ketone 103. An olefination reaction of compound 103 (e.g., with methyltriphenylphosphonium bromide in the presence of a base (for example, NaH, KOBut or NaN(Si$(CH_3)_3)_2$)) leads to the olefin 104, which is reacted with allylamine in an organic solvent, for example DMF, to give compound 105. Removal of the allyl group, for example, by treatment with 1,3-dimethylpyrimidine-2,46(1H,3H,5H)-trione in the presence of $Pd(PPh_3)_4$, followed by reprotection of the free amine with an appropriate amine protecting group, for example, Boc, using $Boc_2O$, gives compound 106, wherein PG is an amine protecting group. Compound 106 may then be converted to an appropriate organometallic reagent by treatment with, for example, a borane, $PdCl_2$(dppf) and KOAc in DMF, $Sn_2(CH_3)_6$ and $Pd(PPh_3)_4$ or alternatively an activated form of Mg or Zn. This organometallic reagent may then be coupled to the halopyrimidine 29, wherein Hal is Br, Cl or I, using a palladium-mediated reaction (e.g., $PdCl_2$(dppf) and aqueous $Na_2CO_3$ in, for example, DMF at room temperature to reflux) to give compound 107. Removal of protecting groups followed by final functionalization of the unprotected free amine (e.g., alkylation or reductive amination to introduce new substituents) gives rise to the final compound 108. These analogues may then be subject to separation techniques to give the single diastereomers.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, Boc, benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113 (3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem., (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. of Chromatogr., (1990) 513:375-378). Enriched or purified enantiomers can be distinguished by methods used to distinguish other chiral molecules with asymmetric carbon atoms, such as optical rotation and circular dichroism.

Administration and Pharmaceutical Formulations

The compounds of the invention may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g. tablets, powders, capsules, solutions, dispersions, suspensions, syrups, sprays, suppositories, gels, emulsions, patches, etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound of the present invention and a carrier or excipient. Suitable carriers and excipients are well known to those skilled in the art and are described in detail in, e.g., Howard C. Ansel et al., Pharmaceutical Dosage Forms and Drug Delivery Systems, (8$^{th}$ Ed. 2004); Alfonso R. Gennaro et al., Remington: The Science and Practice of Pharmacy, (20$^{th}$ Ed. 2000); and Raymond C. Rowe, Handbook of Pharmaceutical Excipients, (5$^{th}$ Ed. 2005). The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

One embodiment of the present invention includes a pharmaceutical composition comprising a compound of Formula I, or a stereoisomer or pharmaceutically acceptable salt thereof. In a further embodiment, the present invention provides a pharmaceutical composition comprising a compound of Formula I, or a stereoisomer or pharmaceutically acceptable salt thereof, together with a pharmaceutically acceptable carrier or excipient.

Methods of Treatment with Compounds of the Invention

The invention includes methods of treating or preventing disease or condition by administering one or more compounds of this invention, or a stereoisomer or pharmaceutically acceptable salt thereof. In one embodiment, a human patient is treated with a compound of Formula I, or a stereoisomer or pharmaceutically acceptable salt thereof, and a pharmaceutically acceptable carrier, adjuvant, or vehicle in an amount to detectably inhibit AKT activity.

In another embodiment of the present invention, a method of treating a hyperproliferative disease in a mammal comprising administering a therapeutically effective amount of the compound of Formula I, or a stereoisomer or pharmaceutically acceptable salt thereof, to the mammal is provided.

In another embodiment, a method of treating or preventing cancer in a mammal in need of such treatment, wherein the method comprises administering to said mammal a therapeutically effective amount of a compound of Formula I, or a stereoisomer or pharmaceutically acceptable salt thereof. The cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia. Another embodiment of the present invention provides the use of a compound of Formula I, or a stereoisomer or pharmaceutically acceptable salt thereof, in the manufacture of a medicament for the treatment of cancer.

In another embodiment, a method of treating or preventing a disease or disorder modulated by AKT, comprising administering to a mammal in need of such treatment an effective amount of a compound of Formula I, or a stereoisomer or pharmaceutically acceptable salt thereof. Examples of such diseases and disorders include, but are not limited to, (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell lung, small cell lung; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); (9) Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; (10) Skin: advanced melanoma, malignant melanoma, basal cell carcinoma, squamous cell carcinoma, Karposi's sarcoma, moles dysplastic nevi, lipoma, angioma, dermatofibroma, keloids, psoriasis; (11) Adrenal glands: neuroblastoma; (12) Breast: metastatic breast; breast adenocarcinoma; (13) Colon; (14) Oral cavity; (15) Hairy cell leukemia; (16) Head and neck; (17) and others including refractory metastatic disease; Kaposi's sarcoma; Bannayan-Zonana syndrome; and Cowden disease or Lhermitte-Duclos disease, among other kinds of hyperproliferative disorders.

Compounds and methods of this invention can be also used to treat diseases and conditions such as rheumatoid arthritis, osteoarthritis, Crohn's disease, angiofibroma, ocular diseases (e.g., retinal vascularisation, diabetic retinopathy, age-related macular degeneration, macular degeneration, etc.), multiple sclerosis, obesity, restenosis, autoimmune diseases, allergy, asthma, endometriosis, atherosclerosis, vein graft stenosis, peri-anastomatic prothetic graft stenosis, prostate hyperplasia, chronic obstructive pulmonary disease, psoriasis, inhibition of neurological damage due to tissue repair, scar tissue formation (and can aid in wound healing), multiple sclerosis, inflammatory bowel disease, infections, particularly bacterial, viral, retroviral or parasitic infections (by increasing apoptosis), pulmonary disease, neoplasm, Parkinson's disease, transplant rejection (as an immunosupressant), septic shock, etc.

Another embodiment of the present invention provides the use of a compound of Formula I, or a stereoisomer or pharmaceutically acceptable salt thereof, in the manufacture of a medicament for the treatment of hyperproliferative diseases. In a further embodiment, the present invention provides the use of a compound of Formula I, or a stereoisomer or pharmaceutically acceptable salt thereof, in the manufacture of a medicament for the treatment of cancer. In a further embodiment, the cancer is selected from carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer, including melanoma, as well as head and neck cancer.

Combination Therapy

The compounds of this invention and stereoisomers and pharmaceutically acceptable salts thereof may be employed alone or in combination with other therapeutic agents for treatment. The compounds of the present invention can be used in combination with one or more additional drugs, for example an anti-inflammatory compound that works by a different mechanism of action. The second compound of the pharmaceutical combination formulation or dosing regimen preferably has complementary activities to the compound of this invention such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

EXAMPLES

In order to illustrate the invention, the following Examples are included. However, it is to be understood that these Examples do not limit the invention and are only meant to suggest a method of practicing the invention. Persons skilled in the art will recognize that the chemical reactions described may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters) (unless otherwise stated). $^1$H NMR spectra were recorded on a Varian instrument operating at 400 MHz. $^1$H-NMR spectra were obtained as CDCl$_3$ [using chloroform (7.25 ppm) as the reference standard] d$_6$-DMSO [using DMSO (2.50 ppm) as the reference standard], CH$_3$OD [using methanol (3.31 ppm) as the reference standard] or d$_6$-acetone [using acetone (2.05 ppm) as the reference standard] solutions (reported in ppm). Alternatively, tetramethylsilane can be used as an internal reference standard (0.00 ppm). When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Example A

AKT-1 Kinase Assay

The activity of the compounds described in the present invention may be determined by the following kinase assay, which measures the phosphorylation of a fluorescently-labeled peptide by full-length human recombinant active AKT-1 by fluorescent polarization using a commercially available IMAP kit.

The assay materials are obtained from an IMAP AKT Assay Bulk Kit, product #R8059, from Molecular Devices, Sunnyvale, Calif. The kit materials include an IMAP Reaction Buffer (5×). The diluted 1×IMAP Reaction Buffer contained 10 mM Tris-HCl, pH 7.2, 10 mM MgCl$_2$, 0.1% BSA, 0.05% NaN$_3$. DTT is routinely added to a final concentration of 1 mM immediately prior to use. Also included is IMAP Binding Buffer (5×), and IMAP Binding Reagent. The Binding Solution is prepared as a 1:400 dilution of IMAP Binding Reagent into 1×IMAP Binding Buffer.

The fluorescein-labeled AKT Substrate (Crosstide) has the sequence (F1)—GRPRTSSFAEG. A stock solution of 20 μM is made up in 1×IMAP Reaction Buffer.

The plates used include a Costar 3657 (382-well made of polypropylene and having a white, v-bottom) that is used for compound dilution and for preparing the compound-ATP mixture. The assay plate is a Packard ProxyPlate™-384 F.

The AKT-1 used is made from full-length, human recombinant AKT-1 that is activated with PDK1 and MAP kinase 2.

To perform the assay, stock solutions of compounds at 10 mM in dimethylsulfoxide ("DMSO") are prepared. The stock solutions and the control compound are serially diluted 1:2 nine times into DMSO (10 μL of compound+10 μL of DMSO) to give 50× dilution series over the desired dosing range. Next, 2.1-μL aliquots of the compounds in DMSO are transferred to a Costar 3657 plate containing 50 μL of 10.4 μM ATP in 1×IMAP Reaction Buffer containing 1 mM DTT. After thorough mixing, aliquots are transferred to a Proxy-Plate™-384 F plate.

The assay is initiated by the addition of 2.5-μL aliquots of a solution containing 200 nM of fluorescently-labeled peptide substrate and 4 nM AKT-1. The plate is centrifuged for 1 minute at 1000 g and incubated for 60 minute at ambient temperature. The reaction is then quenched by the addition of 15 μL of Binding Solution, centrifuged again and incubated for an additional 30 minutes at ambient temperature prior to reading on a Victor 1420 Multilabel HTS Counter configured to measure fluorescence polarization.

Representative compounds were tested in the above assay and found to have IC$_{50}$ values of less than 10 μM.

Example 1

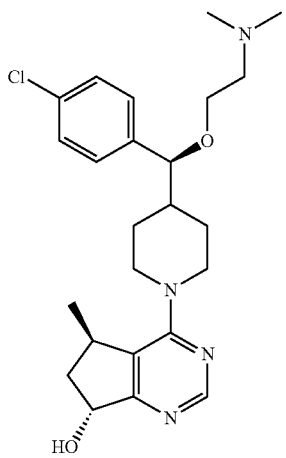

(5R,7R)-4-(4-((S)-(4-chlorophenyl)(2-(dimethylamino)ethoxy)methyl)piperidin-1-yl)-5-methyl-6,7-dihydro-5H-cyclopenta[d]pyrimidin-7-ol Step 1: tert-Butyl 4-(4-chlorobenzoyl)piperidine-1-carboxylate (3.63 g, 11.2 mmol) was dissolved in ethanol (100 mL) then sodium tetrahydroborate (424 mg, 112 mmol) was added to this solution. The reaction mixture was stirred at room temperature for 3 h. LC-MS analysis of the reaction mixture showed no more starting material. The crude reaction mixture was concentrated and the residue was diluted with EtOAc (100 mL) and washed with water (2×50 mL) and brine (50 mL). The organic layer was dried over Na$_2$SO$_4$, filtered and concentrated to yield tert-butyl 4-((4-chlorophenyl)(hydroxy)methyl)piperidine-1-carboxylate (3.46 g, 94%), which was used in the next step directly. m/z: 326 (MH+)

Step 2: To a solution of tert-butyl 4-((4-chlorophenyl)(hydroxyl)methyl)piperidine-1-carboxylate (1.25 g, 3.84 mmol) in DMF (50 mL) was added sodium hydride 60% w/w dispersion on mineral oil (384 mg, 9.59 mmol). The reaction mixture was stirred for 10 minutes at room temperature then 2-chloro-N,N-dimethylethanamine hydrochloride (608 mg, 4.22 mmol) was added. The reaction mixture was stirred at 70° C. for 12 h. LC-MS of the reaction mixture showed no more starting material. The reaction mixture was cooled to room temperature and was diluted with EtOAc (50 mL) and washed with 10% LiCl in water (2×50 mL) followed by water (50 mL) and brine (50 mL). The organic layer was dried over Na$_2$SO$_4$, filtered and concentrated to yield tert-butyl 4-((4-chlorophenyl)(2-(dimethylamino)ethoxy)methyl)piperidine-1-carboxylate that was purified by reversed phase HPLC followed by separation on enantiomers by SFC. (253 mg and 246 mg, 33%) m/z: 397 (MH+)

Step 3: To a solution of tert-butyl 4-((4-chlorophenyl)(2-(dimethylamino)ethoxy)methyl)piperidine-1-carboxylate (156 mg, 0.39 mmol) in methanol (1 mL) was added a solution of 4N HCl on dioxane (1 mL, 4.0 mmol). The reaction mixture was stirred at room temperature for 2 h. LC-MS of the reaction mixture showed no more starting material. The solvent was removed and the (S)-2-((4-chlorophenyl)(piperidin-4-yl)methoxy)-N,N-dimethylethanamine was used in the next step without further purification. m/z: 297 (MH+)

Step 4: To a solution of (5R,7R)-4-chloro-5-methyl-6,7-dihydro-5H-cyclopenta[d]pyrimidin-7-yl 4-nitrobenzoate (65 mg, 0.196 mmol) in THF (1 mL) and water (1 mL) at 0° C. was added lithium hydroxide (19 mg, 0.39 mmol). The reaction mixture was stirred at 0° C. for 30 minutes then it was warmed up to room temperature and stirred for 2 h. LC-MS analysis of the reaction mixture showed no more starting material. THF was removed and water was added (5 mL). The residue was extracted with EtOAc (3×10 mL). The combined organic layers were washed with NaHCO$_3$ (10 mL), brine (10 mL), dried over Na$_2$SO$_4$, filtered and concentrated. The crude product was diluted with 1-butanol (2 mL) and crude (S)-2-((4-chlorophenyl)(piperidin-4-yl)methoxy)-N,N-dimethylethanamine was added followed by DIPEA (0.39 mL, 2.2 mmol). The reaction mixture was heated to 135° C. and was stirred for 4 h. LC-MS of the reaction mixture showed no more starting material. The solvent was evaporated and the residue was purified on silica gel (0%-6% 2N NH$_3$ in MeOH/DCM) gradient elution to yield (5R,7R)-4-(4((S)-(4-chlorophenyl)(2-(dimethylamino)ethoxy)methyl)piperidin-1-yl)-5-methyl-6,7-dihydro-5H-cyclopenta[d]pyrimidin-7-ol as a foam (78 mg, 98%). m/z: 445 (M+); $^1$H NMR (DMSO d$_6$): 9.33 (br s, 1H), 8.61 (s, 1H), 7.48 (d, 2H, J=8.2 Hz), 7.34 (d, 2H, J=8.2 Hz), 5.14-5.11 (m, 1H), 4.69-4.66 (m, 1H), 4.41-4.39 (m, 1H), 4.16-4.14 (m, 1H), 3.45-3.04 (m, 7H), 2.81-2.75 (m, 6H), 2.13-2.00 (m, 4H), 1.39-1.70 (m, 3H), 1.11 (d, 3H, J=6.8 Hz).

Example 2

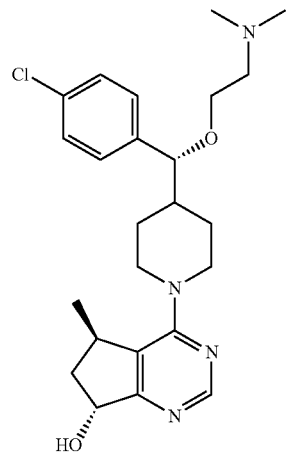

(5R,7R)-4-(4-((R)-(4-chlorophenyl)2-dimethylamino)ethoxy)methyl)piperidin-1-yl)-5-methyl-6,7-dihydro-5H-cyclopenta[d]pyrimidin-7-ol To a solution of (5R,7R)-4-chloro-5-methyl-6,7-dihydro-5H-cyclopenta[d]pyrimidin-7-yl 4-nitrobenzoate (65 mg, 0.196 mmol) in THF (1 mL) and water (1 mL) at 0° C. was added lithium hydroxide (19 mg, 0.39 mmol). The reaction mixture was stirred at 0° C. for 30 minutes then it was warmed up to room temperature and stirred for 2 h. LC-MS analysis of the reaction mixture showed no more starting material. THF was removed and water was added (5 mL). The residue was extracted with EtOAc (3×10 mL). The combined organic layers were washed with NaHCO$_3$ (10 mL), brine (10 mL), dried over Na$_2$SO$_4$, filtered and concentrated. The crude product was diluted with 1-butanol (2 mL) and crude (R)-2-((4-chlorophenyl)(piperidin-4-yl)methoxy)-N,N-dimethylethanamine was added followed by DIPEA (0.39 mL, 2.2 mmol). The reaction mixture was heated to 135° C. and was stirred for 4 h. LC-MS of the reaction mixture showed no more starting material. The solvent was evaporated and the residue was purified on silica gel (0%-6% 2N NH$_3$ in MeOH/DCM) gradient elution to yield (5R,7R)-4-(4-((R)-(4-chlorophenyl)(2-(dimethylamino)ethoxy)methyl)piperidin-1-yl)-5-methyl-6,7-dihydro-5H-cyclopenta[d]pyrimidin-7-ol as a white foam (78 mg, 98%). m/z: 445 (M+); $^1$H NMR (DMSO d$_6$) δ (ppm) 9.46 (br s, 1H), 8.63 (s, 1H), 7.48 (d, 2H, J=8.0 Hz), 7.35 (d, 2H, J=8.1 Hz), 5.18-5.15 (m, 1H), 4.59-4.55 (m, 2H), 4.20-4.16 (m, 1H), 3.58-3.24 (m, 6H), 3.03-2.98 (m, 1H), 2.81-2.75 (m, 6H), 2.14-2.01 (m, 4H), 1.36-1.21 (m, 3H), 1.13 (d, 3H, J=6.9 Hz).

Example 3

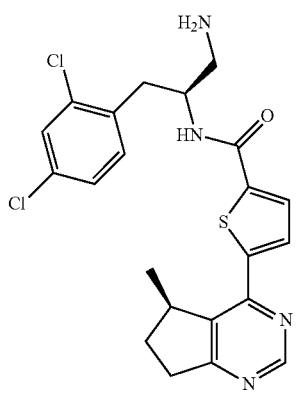

N—((S)-1-amino-3-(2,4-dichlorophenyl)propan-2-yl)-5-((R)-5-methyl-6,7-dihydro-5H-cyclopenta[d]pyrimidin-4-yl)thiophene-2-carboxamide Step 1: (R)-(+)-Pulegone (76.12 g, 0.5 mmol), anhydrous NaHCO$_3$ (12.5 g) and anhydrous ether (500 mL) were added to a 1 L round-bottom flask. The reaction mixture was cooled with an ice-bath under nitrogen. Bromine (25.62 mL, 0.5 mmol) was added dropwise over 30 minutes. The mixture was filtered and carefully added to NaOEt (21%, 412 mL, 1.11 mmol) in an ice-cooled bath. The mixture was stirred at room temperature overnight, and then 5% HCl (1 L) and ether (300 mL) were added. The aqueous phase was extracted with ether (2×300 mL). The combined organic phase was washed with water, dried and concentrated. The residue was added to a warmed solution of semicarbazide hydrochloride (37.5 g) and NaOAc (37.5 g) in water (300 mL). Then boiling ethanol (300 mL) was added to give a clear solution. The mixture was refluxed for 2.5 hours and then stirred at room temperature overnight. The mixture was treated with water (1 L) and ether (300 mL). The aqueous phase was extracted with ether (2×300 mL). The combined organic phase was washed with water, dried and concentrated. The residue was purified by vacuum distillation (73-76° C. at 0.8 mm Hg) to give (2R)-ethyl 2-methyl-5-(propan-2-ylidene)cyclopentanecarboxylate (63 g, 64%). $^1$H NMR (CDCl$_3$, 400 MHz) δ 4.13 (m, 2H), 3.38 (d, J=16 Hz, 0.5H), 2.93 (m, 0.5H), 2.50-2.17 (m, 2H), 1.98 (m, 1H), 1.76 (m, 1H), 1.23 (m, 6H), 1.05 (m, 6H).

Step 2: (2R)-Ethyl 2-methyl-5-(propan-2-ylidene)cyclopentanecarboxylate (24 g, 0.122 mol) in ethyl acetate (100 mL) was cooled to −68° C. with dry ice/isopropanol. Ozonized oxygen (5-7 ft$^3$ h$^{-1}$ of O$_2$) was bubbled through the solution for 3.5 hours. The reaction mixture was flushed with nitrogen at room temperature until the color disappeared. The ethyl acetate was removed under vacuum, and the residue was dissolved in acetic acid (150 mL) and cooled by ice water. Zinc powder (45 g) was then added. The solution was stirred for 30 minutes and then filtered. The filtrate was neutralized with 2N NaOH (1.3 L) and NaHCO$_3$. The aqueous phase was extracted with ether (3×200 mL). The organic phase was combined, washed with water, dried and concentrated to afford (2R)-ethyl 2-methyl-5-oxocyclopentanecarboxylate (20 g, 96%). $^1$H NMR (CDCl$_3$, 400 MHz) δ 4.21 (m, 2H), 2.77 (d, J=11.2 Hz, 1H), 2.60 (m, 1H), 2.50-2.10 (m, 3H), 1.42 (m, 1H), 1.33 (m, 3H), 1.23 (m, 3H).

Step 3: KOH (8.3 g, 147.9 mmol) in water (60 mL) was added to a solution of a mixture of (2R)-ethyl 2-methyl-5-oxocyclopentanecarboxylate (20 g, 117.5 mmol) and thiourea (9.2 g, 120.9 mmol) in ethanol (100 mL). The mixture was refluxed for 10 hours. After cooling, the solvent was removed, and the residue was neutralized with concentrated HCl (12 mL) at 0° C. The mixture was then extracted with DCM (3×150 mL). The solvent was removed, and the residue was purified by silica gel chromatography, eluting with hexane/ethyl acetate (2:1) to give (R)-2-mercapto-5-methyl-6,7-dihydro-5H-cyclopenta[d]pyrimidin-4-ol (12 g, 56%). MS (APCI+) [M+H]$^+$183.

Step 4: Raney Nickel (15 g) and NH$_4$OH (20 mL) were added to a suspension of (R)-2-mercapto-5-methyl-6,7-dihydro-5H-cyclopenta[d]pyrimidin-4-ol (12 g, 65.8 mmol) in distilled water (100 mL). The mixture was refluxed for 3 hours and then filtered. The filtrate was concentrated to afford (R)-5-methyl-6,7-dihydro-5H-cyclopenta[d]pyrimidin-4-ol (9.89 g, 99%). MS (APC+) [M+H]$^+$151.

Steps 5 and 6 describe an alternate synthesis of (R)-5-methyl-6,7-dihydro-5H-cyclopenta[d]pyrimidin-4-ol, starting from (R)-ethyl 2-methyl-5-oxocyclopentanecarboxylate.

Step 5: Ammonium acetate (240 g, 3110 mmol) was added to a solution of (R)-ethyl 2-methyl-5-oxocyclopentanecarboxylate (106 g, 623 mmol) in MeOH (1.2 L). The reaction mixture was stirred at room temperature under nitrogen for 20 hours, after which it was complete as determined by TLC and HPLC. The reaction mixture was concentrated to remove MeOH. The resulting residue was dissolved in DCM, washed twice with H$_2$O, once with brine, dried (Na$_2$SO$_4$), filtered, and concentrated to give (R)-ethyl 2-amino-5-methylcyclopent-1-enecarboxylate (102 g, 97% yield) as an oil. LC/MS (APCI+) m/z 170 [M+H]$^+$.

Step 6: A solution containing (R)-ethyl 2-amino-5-methylcyclopent-1-enecarboxylate (161.6 g, 955 mmol) and ammonium formate (90.3 g, 1433 mmol) in formamide (303.5 mL, 7640 mmol) was heated to an internal temperature of 150° C. and stirred for 17 hours. The reaction mixture was cooled, and transferred to a 2 L single nextracted flask. Excess formamidine was then removed by high vacuum distillation. Once formamidine stopped coming over, the remaining oil in the still pot was dissolved in DCM and washed with brine (3×200 mL). The combined aqueous washes were extracted with DCM. The combined organic extracts were dried (Na$_2$SO$_4$), filtered, and concentrated. The resulting oil was dissolved in minimal DCM, and this solution was added using a separatory funnel to a stirred solution of ether (about 5 volumes of ether vs. DCM solution), causing some precipitate to form. This precipitate was removed by filtration through a medium frit funnel which was rinsed with ether and disposed. The filtrate was concentrated, the trituration from ether repeated two more times and then dried on high vacuum line to give (R)-5-methyl-6,7-dihydro-5H-cyclopenta[d]pyrimidin-4-ol (93.2 g, 65.0% yield) as a pasty solid. LC/MS (APCI−) m/z 149.2.

Step 7: A mixture of (R)-5-methyl-6,7-dihydro-5H-cyclopenta[d]pyrimidin-4-ol (5.8 g, 38.6 mmol) in POCl$_3$ (20 mL) was refluxed for 5 minutes. Excess POCl$_3$ was removed under vacuum, and the residue was dissolved in DCM (50 mL). The mixture was then added to a saturated NaHCO$_3$ solution (200 mL). The aqueous phase was extracted with DCM (3×100 mL), and the combined organic phases were dried and concentrated. The resulting residue was purified by silica gel chromatography, eluting with ethyl acetate to give (R)-4-chloro-5-methyl-6,7-dihydro-5H-cyclopenta[d]pyrimidine (3.18 g, 49%). $^1$H NMR (CDCl$_3$, 400 MHz) δ 8.81 (s, 1H), 3.47 (m, 1H), 3.20 (m, 1H), 3.05 (m, 1H), 2.41 (m, 1H), 1.86 (m, 3H), 1.47 (m, 3H).

Step 8: Pd(PPh$_3$)$_4$ (10 mg, 0.09 mmol) was added to a degassed solution of (R)-4-chloro-5-methyl-6,7-dihydro-5H-cyclopenta-[d]-pyrimidine (300 mg, 1.78 mmol) and a 0.5M solution of 5-ethoxycarbonyl-2-thienylzinc bromide in THF (3.6 mL, 1.78 mmol). The reaction mixture was stirred at 70° C. for 16 hours and then it was cooled to room temperature and diluted with diethyl ether (10 mL). Water was added (5 mL) and a precipitate was formed and filtered. The solid was washed with more diethyl ether and the filtrate was concentrated. The resulting oil was purified on silica gel (0%-75% EtOAc/hexanes) to yield (R)-ethyl 5-(5-methyl-6,7-dihydro-5H-cyclopenta[d]pyrimidin-4-yl)thiophene-2-carboxylate as an oil (400 mg, 78%). m/z: 289 (MH+), $^1$H NMR (CDCl$_3$): δ (ppm) 8.95 (s, 1H), 7.84-7.82 (m, 1H), 7.70-7.69 (m 1H), 4.39 (dq, 2H, J1=7.2 Hz, J2=1.2 Hz), 3.77 (quint., 1H, J=7.2 Hz), 3.23-1.14 (m, 1H), 3.001-2.95 (m, 1H), 2.42-2.31 (m, 1H), 1.98-1.92 (m, 1H), 1.40 (dt, 3H, J1=7.2 Hz, J2=1.2 Hz), 1.29 (d, 3H, J=7.2 Hz).

Step 9: A 1N solution of sodium hydroxide in water (2.4 mL) was added to a solution of (R)-ethyl 5-(5-methyl-6,7-dihydro-5H-cyclopenta[d]pyrimidin-4-yl)thiophene-2-carboxylate (236 mg, 0.818 mmol) in ethanol (2.5 mL). The reaction mixture was stirred at room temperature for 16 hours. LC-MS analysis of the reaction mixture showed no more starting material. Water (5 mL) was added, and the solution was acidified with 1N HCl (1 mL) and extracted with EtOAc (3×5 mL). The combined organic layers were washed with brine, dried over Na$_2$SO$_4$, filtered and concentrated. The resulting (R)-5-(5-methyl-6,7-dihydro-5H-cyclopenta[d]pyrimidin-4-yl)thiophene-2-carboxylic acid was used without further purification. m/z: 261 (MH+).

Step 10: A solution of lithium tetrahydroborate (190 mg, 8.50 mmol) in THF (4 mL) was cooled to 0° C. Chlorotrimethylsilane (2.2 mL, 17 mmol) was added dropwise. The mixture was stirred for 20 minutes at room temperature and then returned to 0° C. (S)-2-amino-3-(2,4-dichlorophenyl)propanoic acid (1.00 g, 4.27 mmol) was then added. The reaction was allowed to warm up slowly to room temperature while stirring overnight. The mixture was cooled to 0° C. and quenched by slow addition of methanol (1 mL) followed by an aqueous solution of 2N sodium hydroxide (4.2 mL, 8.54 mmol). Volatiles were removed under reduces pressure. The slurry was diluted with water (5 mL) and extracted with DCM (3×15 mL). The combined organic layers were washed with brine, dried over Na$_2$SO$_4$, filtered and concentrated to afford (S)-2-amino-3-(2,4-dichlorophenyl)propan-1-ol as a solid that was used in the next step without further purification. MS m/z 220 (M+).

Step 11: di-tert-Butyldicarbonate (850 mg, 3.90 mmol) was added to a solution of (S)-2-amino-3-(2,4-dichlorophenyl)propan-1-ol (859 mg, 3.90 mmol) in CHCl$_3$ (10 mL). The reaction mixture was stirred at room temperature for 18 hours. LC-MS analysis of the reaction mixture showed no more starting material. The solvent was removed under reduced pressure, and the resulting residue was purified on silica gel (49:49:2 DCM: EtOAc: MeOH) to yield (5)-tert-butyl 1-(2,4-dichlorophenyl)-3-hydroxypropan-2-ylcarbamate as a solid (1.17 g, 94%). MS m/z 320 (M+); $^1$H NMR (CDCl$_3$): δ (ppm) 7.38 (s, 1H), 7.23-7.17 (m, 2H), 4.84-4.82 (m, 1H), 3.95-3.87 (m, 1H), 3.74-3.68 (m, 1H), 3.63-3.55 (m, 1H), 3.02-2.98 (m, 2H), 2.31 (br s, 1H), 1.39 (s, 9H).

Step 12: A solution of (S)-tert-butyl 1-(2,4-dichlorophenyl)-3-hydroxypropan-2-ylcarbamate (50 mg, 0.156 mmol) in DCM (1 mL) was cooled to 0° C. Triethylamine (24 µL, 0.172 mmol) was added, followed by methanesulfonyl chloride (24 µL, 0.312 mmol). The reaction mixture was allowed to warm up slowly to room temperature and was stirred for 4 hours. TLC analysis of the reaction mixture showed no more starting material. Diethyl ether was added, and the precipitate was filtered. The filtrate was concentrated, and the resulting residue was diluted with DMF (0.5 mL), and sodium azide (51 mg, 0.781 mmol) was added. The reaction mixture was heated to 100° C. for 16 hours. LC-MS of mixture showed no more starting material. Water was added (5 mL), and the reaction mixture was extracted with diethyl ether (3×5 mL). The combined organic layers were washed with brine, dried over Na$_2$SO$_4$, filtered and concentrated. The crude product was purified on silica gel (0%-70% EtOAc/hexanes gradient elution to yield (S)-tert-butyl 1-azido-3-(2,4-dichlorophenyl) propan-2-ylcarbamate as an oil (32 mg, 59%). m/z 345 (M+); $^1$H NMR (CDCl$_3$) δ (ppm) 7.39 (s, 1H), 7.21-7.17 (m, 2H), 4.71-4.68 (m, 1H), 4.07-4.02 (m, 1H), 3.52-3.38 (m, 2H), 2.95-2.86 (m, 2H), 1.38 (s, 9H).

Step 13: TFA (0.56 mL, 7.24 mmol) was added to a solution of (S)-tert-butyl 1-azido-3-(2,4-dichlorophenyl)propan-2-ylcarbamate (100 mg, 0.290 mmol) in DCM (2 mL) The reaction mixture was stirred at room temperature for 1 hour. LC-MS of the reaction mixture showed no more starting material. The solvent was removed, and the residue was co-evaporated with toluene (3×10 mL). The (S)-1-azido-3-(2,4-dichlorophenyl)propan-2-amine was carried to the next step without further purification. m/z 246 (MH+).

Step 14: (S)-1-Azido-3-(2,4-dichlorophenyl)propan-2-amine (33 mg, 0.134 mmol) was added to a solution of (R)-5-(5-methyl-6,7-dihydro-5H-cyclopenta[d]pyrimidin-4-yl) thiophene-2-carboxylic acid (35 mg, 0.134 mmol) in DCM (0.7 mL) HBTU (56 mg, 0.148 mmol) was added, followed by DIPEA (0.23 mL, 1.34 mmol). The reaction mixture was stirred at room temperature for 1 hour. LC-MS of the reaction mixture showed no more starting material. The solvent was removed, and the resulting residue was purified on silica gel (0%-50% EtOAc/hexanes) gradient elution to yield N—((S)-1-azido-3-(2,4-dichlorophenyl)propan-2-yl)-5-(R)-5-methyl-6,7-dihydro-5H-cyclopenta[d]pyrimidin-4-yl) thiophene-2-carboxamide as an oil (59 mg, 90%). m/z 486 (MH+).

Step 15: 10% Pd/C (6 mg) was added to a solution of N—((S)-1-azido-3-(2,4-dichlorophenyl)propan-2-yl)-5-(R)-5-methyl-6,7-dihydro-5H-cyclopenta[d]pyrimidin-4-yl) thiophene-2-carboxamide (59 mg, 0.121 mmol) in methanol (2.5 mL). The solution was put under vacuum and purged with H$_2$ (3×), and then the reaction mixture was stirred under a hydrogen atmosphere for 2 hours. LC-MS analysis of the reaction mixture showed no more starting material. The reaction mixture was filtered and concentrated to yield N—((S)-1-amino-3-(2,4-dichlorophenyl)propan-2-yl)-5-((R)-5-methyl-6,7-dihydro-5H-cyclopenta[d]pyrimidin-4-yl) thiophene-2-carboxamide as a foam (53 mg, 95%). m/z 461 (M+); $^1$H NMR (DMSO d$_6$) δ (ppm) 8.91 (s, 1H), 8.58-8.56 (m, 1H), 7.90 (br s, 2H), 7.84 (d, 1H, J=4.3 Hz), 7.78 (d, 1H, J=4.1 Hz), 7.60 (m, 1H), 7.39-7.33 (m, 2H), 4.55-4.42 (m, 1H), 3.87-3.77 (m, 1H), 3.19-2.84 (m, 6H), 2.33-2.26 (m, 1H), 1.88-1.82 (m, 1H), 1.18 (d, 3H, J=6.9 Hz).

Example 4

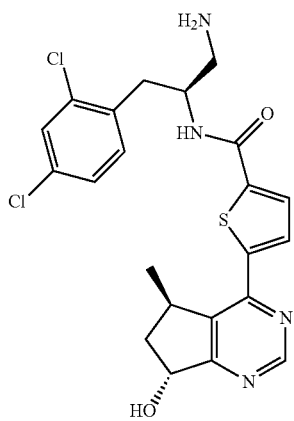

N—((S)-1-amino-3-(2,4-dichlorophenyl)propan-2-yl)-5-(5R,7R)-7-hydroxy-5-methyl-6,7-dihydro-5H-cyclopenta[d]pyrimidin-4-yl)thiophene-2-carboxamide Step 1: m-CPBA (1.06 g, 6.12 mmol) was added portionwise to a solution of (R)-methyl 5-(5-methyl-6,7-dihydro-5H-cyclopenta[d]pyrimidin-4-yl)thiophene-2-carboxylate (883 mg, 3.06 mmol) in CHCl$_3$ (20 mL) at 0° C. The reaction mixture was stirred at 0° C. for 10 minutes then it was warmed up to room temperature and stirred for 18 hours. LC-MS analysis of the reaction mixture showed no more starting material. The reaction mixture was cooled to 0° C., and a solution of Na$_2$S$_2$O$_3$ (968 mg, 6.12 mmol) in water (5 mL) was added dropwise, followed by a solution of Na$_2$CO$_3$ (649 mg, 6.12 mmol) in water (10 mL). The reaction mixture was stirred for 30 minutes at 0° C., and then it was warmed up to room temperature and extracted with CHCl$_3$ (3×25 mL). The combined organic layers were washed with brine, dried over Na$_2$SO$_4$, filtered and concentrated to give the N-oxide as an oil. The crude product was dissolved in acetic anhydride (5.8 mL, 61.2 mmol), and the solution was heated to 90° C. for 2 hours. The excess acetic anhydride was then removed under reduced pressure, and the residue was dissolved in DCM (20 mL) and poured slowly into a stirred aqueous saturated solution of Na$_2$CO$_3$ cooled to 0° C. The mixture was extracted with DCM (3×10 mL). The combined organic layers were washed with brine, dried over Na$_2$SO$_4$, filtered and concentrated to yield an oil. The oil was dissolved in THF (15 mL), and a solution of LiOH (366 mg, 7.65 mmol) in water (2.2 mL) was added. The reaction mixture was stirred at room temperature under N$_2$ for 16 hours. LC-MS analysis of the reaction mixture showed no more starting material. Water was added (10 mL), and the reaction mixture was extracted with EtOAc (3×10 mL). The combined organic layers were washed with brine, dried over Na$_2$SO$_4$, filtered and concentrated to yield a solid that was purified by reversed phase HPLC to give (R)-5-(7-hydroxy-5-methyl-6,7-dihydro-5H-cyclopenta[d]pyrimidin-4-yl)thiophene-2-carboxylic acid (336 mg, 40%) as a mixture of diastereoisomers. m/z 277 (MH$^+$).

Step 2: Trimethylsilyldiazomethane (1.10 mmol) was added dropwise to a suspension of (R)-5-(7-hydroxy-5-methyl-6,7-dihydro-5H-cyclopenta[d]pyrimidin-4-yl)thiophene-2-carboxylic acid (200 mg, 0.723 mmol) in MeOH (5 mL) and Et$_2$O (5 mL) The reaction mixture was stirred for 1 hour at room temperature, and then the solvent was removed under reduced pressure. The residue was diluted with DCM (10 mL) and then cooled to 0° C. Triethylamine (131 µL, 0.94 mmol) was added, followed by the addition of p-nitrobenzoyl chloride (148 mg, 0.792 mmol). The reaction mixture was allowed to warm up slowly to room temperature and was stirred for 4 hours. TLC analysis of the reaction mixture showed no more starting material. The reaction mixture was quenched by the addition of saturated aqueous solution of NaHCO$_3$ (5 mL), and the reaction mixture was extracted with DCM (3×10 mL). The combined organic layers were washed with brine, dried over Na$_2$SO$_4$, filtered and concentrated. The crude product was purified on silica gel (10%-45% EtOAc/hexanes) gradient elution to yield 5-((5R,7R)-5-methyl-7-(4-nitrobenzoyloxy)-6,7-dihydro-5H-cyclopenta[d]pyrimidin-4-yl)thiophene-2-carboxylate as a solid (32 mg, 10%). m/z 440 (MH+); $^1$H NMR (CDCl$_3$) δ (ppm) 9.12 (s, 1H), 8.31-8.26 (m, 4H), 7.87 (d, 1H, J=4.0 Hz), 7.76 (d, 1H, J=4.0 Hz), 6.63 (dd, 1H, J$_1$=7.7 Hz, J$_2$=7.8 Hz), 3.95 (s, 3H), 2.71-2.65 (m, 1H), 2.51-2.43 (m, 1H), 1.43 (d, 3H, J=7.1 Hz).

Step 3: Lithium hydroxide (6 mg, 0.146 mmol) was added to a solution of 5-((5R,7R)-5-methyl-7-(4-nitrobenzoyloxy)-6,7-dihydro-5H-cyclopenta[d]pyrimidin-4-yl)thiophene-2-carboxylate (32 mg, 0.073 mmol) in THF (0.5 mL) and water (0.5 mL). The reaction mixture was stirred at room temperature for 1 hour. LC-MS of the reaction mixture showed no more starting material. THF was removed under reduced pressure, and 1N HCl (5 mL) was added. The reaction mixture was extracted with EtOAc (3×5 mL). The combined organic layers were washed with brine, dried over Na$_2$SO$_4$, filtered and concentrated to give 5-((5R,7R)-7-hydroxy-5-methyl-6,7-dihydro-5H-cyclopenta[d]pyrimidin-4-yl)thiophene-2-carboxylic acid. The crude mixture was used directly in the next step without further purification.

Step 4: (S)-1-Azido-3-(2,4-dichlorophenyl)propan-2-amine (20 mg, 0.0724 mmol) was added to a solution of 5-((5R,7R)-7-hydroxy-5-methyl-6,7-dihydro-5H-cyclopenta[d]pyrimidin-4-yl)thiophene-2-carboxylic acid (35 mg, 0.145 mmol) in DCM (0.5 mL) DMF (125 µL) was added to solubilize the starting material completely. DIPEA (126 µL, 0.724 mmol) was added, followed by the addition of HBTU (30 mg, 0.079 mmol). The reaction mixture was stirred at room temperature for 1 hour. LC-MS of the reaction mixture showed no more starting material. The solvent was removed, and the resulting residue was purified by reversed phase HPLC to yield N—((S)-1-azido-3-(2,4-dichlorophenyl)propan-2-yl)-5-((5R,7R)-7-hydroxy-5-methyl-6,7-dihydro-5H-cyclopenta[d]pyrimidin-4-yl)thiophene-2-carboxamide product as a solid (4 mg, 10%). m/z 504 (MH$^+$).

Step 5: 10% w/w Pd/C (1 mg) was added to a solution of N—((S)-1-azido-3-(2,4-dichlorophenyl)propan-2-yl)-5-((5R,7R)-7-hydroxy-5-methyl-6,7-dihydro-5H-cyclopenta[d]pyrimidin-4-yl)thiophene-2-carboxamide (4.0 mg, 0.008 mmol) in MeOH (0.5 mL). The solution was put under vacuum and purged with H$_2$ (3×). The reaction mixture was then stirred under a hydrogen atmosphere for 2 hours. LC-MS analysis of the reaction mixture showed no more starting material. The reaction mixture was filtered and then concentrated to yield N—((S)-1-amino-3-(2,4-dichlorophenyl)propan-2-yl)-5-(5R,7R)-7-hydroxy-5-methyl-6,7-dihydro-5H-cyclopenta[d]pyrimidin-4-yl)thiophene-2-carboxamide as a solid (3.7 mg, 98%). m/z 477 (M$^+$). $^1$H NMR (DMSO d$_6$) δ (ppm) 8.91 (s, 1H), 8.58-8.56 (m, 1H), 7.90 (br s, 2H), 7.84 (d, 1H, J=4.3 Hz), 7.78 (d, 1H, J=4.1 Hz), 7.60 (m, 1H), 7.39-7.33 (m, 2H), 5.22-5.17 (m, 1H), 4.59-4.50 (m, 1H), 3.87-

3.77 (m, 1H), 3.19-2.84 (m, 5H), 2.33-2.26 (m, 1H), 1.88-1.82 (m, 1H), 1.13 (d, 3H, J=6.9 Hz).

Example 5

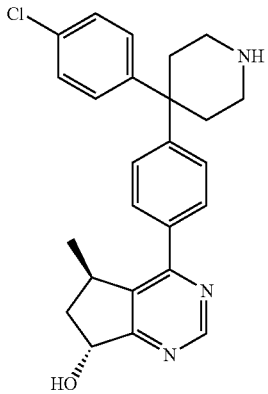

(5R,7R)-4-(4-(4-(4-chlorophenyl)piperidin-4-yl)phenyl)-5-methyl-6,7-dihydro-5H-cyclopenta[d]pyrimidin-7-ol Step 1: Ammonium acetate (240 g, 3110 mmol) was added to a solution of (R)-ethyl 2-methyl-5-oxocyclopentanecarboxylate (106.0 g, 622.8 mmol) in MeOH (1.2 L). The reaction mixture was stirred at room temperature under nitrogen for 20 hours. The reaction was complete as determined by TLC and HPLC. The reaction mixture was concentrated to remove MeOH. The resulting residue was dissolved in DCM, washed twice with H$_2$O, once with brine, dried (Na$_2$SO$_4$), filtered, and concentrated to give (R)-ethyl 2-amino-5-methylcyclopent-1-enecarboxylate (102 g, 97% yield) as an oil. LC/MS (APCI+) m/z 170 [M+H]+.

Step 2: A solution containing (R)-ethyl 2-amino-5-methylcyclopent-1-enecarboxylate (161.6 g, 955.0 mmol) and ammonium formate (90.3 g, 1430 mmol) in formamide (303.5 mL, 7640 mmol) was heated to an internal temperature of 150° C. and stirred for 17 hours. The reaction mixture was cooled, and transferred to a 2 L single nextracted flask. Then excess formamidine was removed by high vacuum distillation. Once formamidine stopped coming over, the remaining oil in the still pot was dissolved in DCM and washed with brine (3×200 mL). The combined aqueous washes were extracted with DCM. The combined organic extracts were dried (Na$_2$SO$_4$), filtered, and concentrated. The resulting oil was dissolved in minimal DCM, and this solution was added using a separatory funnel to a stirred solution of ether (about 5 volumes of ether vs. DCM solution), causing some precipitate to form. This precipitate was removed by filtration through a medium frit funnel, which was rinsed with ether and disposed. The filtrate was concentrated, the trituration from ether repeated two more times and then dried on high vacuum line to give (R)-5-methyl-6,7-dihydro-5H-cyclopenta[d]pyrimidin-4-ol (93.23 g, 65.00% yield) as a pasty solid. LC/MS (APCI−) m/z 149.2.

Step 3: Neat POCl$_3$ (463.9 mL, 5067 mmol) was added slowly by addition funnel to a 0° C. solution of (R)-5-methyl-6,7-dihydro-5H-cyclopenta[d]pyrimidin-4-ol (152.2 g, 1013 mmol) in DCE (1.2 L). After the addition was complete, the reaction mixture was warmed to room temperature. The reaction mixture was then heated to reflux and stirred for 70 minutes. The reaction was complete as determined by HPLC. The reaction mixture was cooled to room temperature, and the excess POCl$_3$ was quenched in 4 portions as follows: The reaction mixture was transferred to a separatory funnel and dripped into a beaker containing ice and a saturated NaHCO$_3$ solution cooled in an ice bath. Once the addition of each portion of the reaction mixture was completed, the quenched mixture was stirred 30 minutes to ensure complete destruction of POCl$_3$ prior to transfer to separatory funnel. The mixture was transferred to the separatory funnel and extracted twice with DCM. The combined extracts were dried (Na$_2$SO$_4$), filtered, and concentrated. The crude was purified on silica gel as follows: silica gel (1 kg) was slurried in 9:1 hexane:ethyl acetate onto a 3 L fritted funnel, the silica settled under vacuum and topped with sand. The crude was loaded with a DCM/hexane mixture, and the compound was eluted using 1 L sidearm flasks under vacuum to give (R)-4-chloro-5-methyl-6,7-dihydro-5H-cyclopenta[d]pyrimidine (104.4 g, 61.09% yield) as an oil.

Step 4: Solid 77% maximum m-CPBA (12 g, 53 mmol) was added portionwise to a 0° C. solution of (R)-4-chloro-5-methyl-6,7-dihydro-5H-cyclopenta[d]pyrimidine (5 g, 30 mmol) in CHCl$_3$ (80 mL). The reaction mixture was stirred at room temperature overnight. The reaction mixture was cooled to 0° C., and then treated by the addition of NaHCO$_3$ (25 g, 196 mmol) slurry in water (100 mL). This was followed by the dropwise addition of Na$_2$CO$_3$ (14 g, 128 mmol) in water (100 mL). The reaction mixture was stirred for 30 minutes. The aqueous phase was extracted with CHCl$_3$. The organic phase was dried with MgSO$_4$ and concentrated under reduced pressure at low temperature (<25° C.) to afford the crude (R)-4-chloro-5-methyl-6,7-dihydro-5H-cyclopenta[d]pyrimidine 1-oxide (5.5 g, 100%), which was used in the next step without further purification.

Step 5: A solution of the (R)-4-chloro-5-methyl-6,7-dihydro-5H-cyclopenta[d]pyrimidine 1-oxide (5.5 g, 29.8 mmol) in Ac$_2$O (40.5 mL, 429 mmol) was heated to 110° C. for 3 hours. After cooling, the acetic anhydride was evaporated, and the resulting residue was taken up in DCM. This solution was added to a stirring cold solution of saturated NaHCO$_3$. The layers were extracted with DCM, dried MgSO$_4$, filtered, and concentrated. The crude oil was chromatographed (Biotage) eluting with 20% EtOAc/hexane, to provide (5R)-4-chloro-5-methyl-6,7-dihydro-5H-cyclopenta[d]pyrimidin-7-yl acetate (3.0 g, 44.4%).

Step 6: A solution of (5R)-4-chloro-5-methyl-6,7-dihydro-5H-cyclopenta[d]pyrimidin-7-yl acetate (11.86 g, 52.33 mmol) in 2:1 THF:H$_2$O (270 mL) was cooled to 0° C. and treated with lithium hydroxide hydrate (3.95 g, 94.2 mmol). The reaction was stirred at room temperature for 4 hours. The reaction was concentrated and diluted with water and acidified with 6N HCl to a pH of 6. The aqueous layer was extracted with EtOAc. The combined organics were washed with brine, dried MgSO$_4$, filtered, and concentrated. The crude residue was chromatographed (Biotage 65) eluting with 30-50% EtOAc/hexane to give (5R)-4-chloro-5-methyl-6,7-dihydro-5H-cyclopenta[d]pyrimidin-7-ol (6.09 g, 63%).

Step 7: Solid 4-nitrobenzoyl chloride (6.73 g, 36.3 mmol) was added to a stirred solution of (5R)-4-chloro-5-methyl-6,7-dihydro-5H-cyclopenta[d]pyrimidin-7-ol (6.09 g, 33.0 mmol) and NEt$_3$ (5.98 mL, 42.9 mmol) in DCM (165 mL) at 0° C. The reaction was warmed to room temperature and then stirred at room temperature for 3 hours. The reaction was diluted with DCM and saturated aqueous NaHCO$_3$. The combined extracts were washed with brine, dried MgSO$_4$, filtered, and concentrated. The crude residue was chromatographed eluting with 10-14% EtOAc/hexane several times to give (5R,7S)-4-chloro-5-methyl-6,7-dihydro-5H-cyclopenta[d]pyrimidin-7-yl 4-nitrobenzoate (3.96 g, 36%) and (5R,7R)-4-chloro-5-methyl-6,7-dihydro-5H-cyclopenta[d]pyrimidin-7-yl-4-nitrobenzoate (5.92 g, 54%).

Step 8: n-Butyl lithium (16 mL, 2.5M solution in hexanes, 39.9 mmol) was added to a solution of 1-bromo-4-chlorobenzne (8.62 g, 45.0 mmol) in anhydrous THF (100 mL) at −78° C. under nitrogen. After 30 minutes at −78° C., 1-Boc-piperidone (6.62 g, 33.2 mmol) was added dropwise as a solution in anhydrous THF (5 mL). After 30 minutes at −78° C., the reaction was quenched with a saturated $NH_4Cl$ solution (100 mL), extracted with EtOAc (2×100 mL). The combined organics were dried ($Na_2SO_4$), filtered and concentrated. The crude product was purified by silica gel chromatography, eluting with EtOAc/hexane (0-40%) to give tert-butyl 4-(4-chlorophenyl)-4-hydroxypiperidine-1-carboxylate (7.64 g, 74% yield). $^1$H NMR ($CDCl_3$, 400 MHz) δ 7.38 (d, H=7.2 Hz, 2H), 7.15 (d, J=7.3 Hz, 2H), 3.94 (br s, 2H), 3.18 (br s, 2H), 1.89 (br s, 2H), 1.46 (s, 11H). LCMS: M+1 312.2.

Step 9: Solid aluminum trichloride (0.68 mL, 5.1 mmol) was added to a solution of tert-butyl 4-(4-chlorophenyl)-4-hydroxypiperidine-1-carboxylate (0.40 g, 1.3 mmol) in bromobenzene (5.4 mL, 51.3 mmol) at 0° C. under nitrogen. After being stirred at 0° C. for 4 hours, the mixture was quenched with ice and concentrated under reduced pressure. The mixture was dissolved in 1N LiOH (30 mL) and extracted with EtOAc (2×30 mL). The combined organics were dried with $Na_2SO_4$, filtered and concentrated. The crude product was directly taken up in EtOAc (4 mL) and aqueous $Na_2CO_3$ solution (2M, 4 mL). Di-tert-butyldicarbonate (0.851 g, 3.9 mmol) was added in one portion. The mixture was stirred at 23° C. overnight. The next day, two layers were separated, and the aqueous layer was further extracted with EtOAc (2×10 mL). The combined organics were dried over $Na_2SO_4$, concentrated, and purified by column chromatography (0-40% EtOAc/hexanes) to give tert-butyl 4-(4-bromophenyl)-4-(4-chlorophenyl)piperidine-1-carboxylate (0.302 g, 51% yield). $^1$H NMR ($CDCl_3$, 400 MHz) δ 7.46 (d, J=7.2 Hz, 2H), 7.32 (d, J=6.9 Hz, 2H), 7.19 (d, J=7.0 Hz, 2H), 7.12 (d, J=7.3 Hz, 2H), 3.54 (br s, 2H), 2.35 (br s, 2H), 1.54 (br s, 2H), 1.43 (s, 11H). LCMS: M+1 452.2.

Step 10: Bispinacol ester boronate (93 mg, 0.37 mmol) was added under nitrogen to a solution of tert-butyl 4-(4-bromophenyl)-4-(4-chlorophenyl)piperidine-1-carboxylate (150 mg, 0.33 mmol) in 1,4-dioxane (5 mL) at 23° C. Potassium acetate (98 mg, 1.0 mmol) was then added, and finally 1,1'-bis(diphenylphosphino)ferrocenepalladium (II) chloride (10 mg, 0.02 mmol) was added. The mixture was heated to 100° C. under nitrogen. After 3 hours, the reaction was cooled to room temperature, diluted with $H_2O$ (10 mL), and extracted with EtOAc (2×10 mL). The combined organics were dried ($Na_2SO_4$), filtered and concentrated. The crude material was purified by column chromatography (gradient from 100% hexane to 4:6 EtOAc:hexanes) to give the boronate (120 mg, 72% yield). (5R,7R)-4-chloro-5-methyl-6,7-dihydro-5H-cyclopenta[d]pyrimidin-7-yl 4-nitrobenzoate (82 mg, 0.246 mmol) was added to this boronate (120 mg, 0.24 mmol), followed by the addition of 1,4-dioxane (3 mL) and aqueous $Na_2CO_3$ solution (1M, 0.3 mL). The mixture was flushed with nitrogen and bis(triphenylphosphine)palladium (II) chloride (8.6 mg, 0.123 mmol) was added in one portion. The mixture was heated at 100° C. under nitrogen for 12 hours. Then the reaction mixture was diluted with 0.1N LiOH solution (10 mL) and extracted into EtOAc (2×10 mL). The combined organic extracts were dried over $Na_2SO_4$, filtered, concentrated under reduced pressure, and purified by column chromatography (0-100% EtOAc/hexanes) to give tert-butyl 4-(4-chlorophenyl)-4-(4-((5R,7R)-5-methyl-7-(4-nitrobenzoyloxy)-6,7-dihydro-5H-cyclopenta[d]pyrimidin-4-yl)phenyl)piperidine-1-carboxylate (36 mg, 29% yield) as an oil.

Step 11: tert-Butyl 4-(4-chlorophenyl)-4-(4-((5R,7R)-5-methyl-7-(4-nitrobenzoyloxy)-6,7-dihydro-5H-cyclopenta[d]pyrimidin-4-yl)phenyl)piperidine-1-carboxylate (36 mg, 0.069 mmol) was dissolved in DCM (3 mL) and cooled to 0° C. Then TFA (1.5 mL) was added dropwise. The resulting solution was stirred at 0° C. for 1 hour, concentrated under reduced pressure, dissolved in DMF (1 mL) and purified by reverse phase HPLC (0-100% $AcCN/H_2O$) to give (5R,7R)-4-(4-(4-(4-chlorophenyl)piperidin-4-yl)phenyl)-5-methyl-6,7-dihydro-5H-cyclopenta[d]pyrimidin-7-ol di-TFA salt (9 mg, 31% yield). $^1$H NMR (DMSO-$d_6$, 400 MHz) δ 9.09 (s, 1H), 7.88 (d, J=8.8 Hz, 2H), 7.52 (d, J=8.4 Hz, 2 H), 7.42 (q, J=4.8 Hz, 4H), 5.64 (d, J=6.0 Hz, 1H), 5.06 (q, J=6.8 Hz, 1H), 3.85 (br s, 1H), 3.05 (br s, 3H), 2.89 (m, 2H), 2.61 (br s, 3H), 2.11 (m, 2H), 1.16 (t, J=6.4 Hz, 3H), 1.04 (d, J=6.6 Hz, 3H). LCMS: M+1 420.4.

Example 6

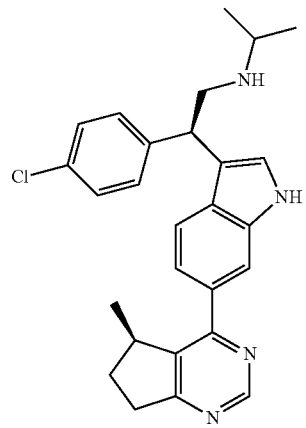

N—((R)-2-(4-chlorophenyl)-2-(6-((R)-5-methyl-6,7-dihydro-5H-cyclopenta[d]pyrimidin-4-yl)-1H-indol-3-yl)ethyl)propan-2-amine Step 1: 1-((1E)-2-Nitrovinyl)-4-chlorobenzene (0.206 g, 1.12 mmol) was added to a solution of 6-bromoindole (0.200 g, 1.02 mmol) in methanol (5 mL), followed by the addition of sufamic acid (39.6 mg, 0.40 mmol). The mixture was stirred at 80° C. for 16 hours. The mixture was concentrated then diluted with EtOAc (15 mL) and washed with $H_2O$ (15 mL). The organic layer was dried ($Na_2SO_4$), filtered and concentrated. The crude product was purified by silica gel chromatography, eluting with EtOAc/hexane (0-50%) to give 6-bromo-3-(1-(4-chlorophenyl)-2-nitroethyl)-1H-indole (0.175 g, 45.2%). $^1$H NMR ($CDCl_3$, 400 MHz) δ 8.12 (s, 1H), 7.51 (s, 1H), 7.28 (d, J=8.5 Hz, 2H), 7.25-7.20 (m, 3H), 7.17 (d, J=8.5 Hz, 1H), 7.15 (s, 1H), 5.12 (t, 1H), 5.01 (q, 1H), 4.88 (q, 1H).

Step 2: A solution containing 6-bromo-3-(1-(4-chlorophenyl)-2-nitroethyl)-1H-indole (0.210 g, 0.553 mmol), bispinacol ester boronate (168 mg, 0.664 mmol) and potassium acetate (0.163 g, 1.66 mmol) in 1,4-dioxane (5.00 mL) was deoxygenated, and then [1,1'-Bis(diphenylphosphino)ferrocene]dichloropalladium(II) complex with dichloromethane (22.6 mg, 0.0276 mmol, 1:1) was added. The mixture was heated at 80° C. for 15 hours. The mixture was cooled to ambient temperature, diluted with H₂O (10 mL) and extracted with EtOAc (2×10 mL). The combined organic were dried (Na₂SO₄), filtered and concentrated. The crude product was purified by silica gel chromatography, eluting with EtOAc/hexane (0-50%) to give pure boronate (0.146 g, 74.5%). (R)-4-Chloro-5-methyl-6,7-dihydro-5H-cyclopenta[d]pyrimidine (52.4 mg, 0.311 mmol), Bis(triphenylphosphine)palladium(II) chloride (17.5 mg, 0.0249 mmol) were added to the boronate (0.146 g, 0.342 mmol), followed by the addition of acetonitrile (0.933 mL) and aqueous KOAc solution (0.933 mL, 1M). The mixture was cooled to ambient temperature, diluted with H₂O (10 mL) and extracted with EtOAc (2×10 mL). The combined organic were dried (Na₂SO₄), filtered and concentrated. The crude product was purified by silica gel chromatography, eluting with EtOAc/hexane (0-100%) to give (5R)-4-(3-(1-(4-chlorophenyl)-2-nitroethyl)-1H-indol-6-yl)-5-methyl-6,7-dihydro-5H-cyclopenta[d]pyrimidine (0.115 g, 85.4%). LCMS: M+1 433.4.

Step 3: A suspension of nickel chloride hexahydrate (31.6 mg, 0.133 mmol) in methanol (10 mL, 200 mmol) was sonicated until complete dissolution. Sodium tetrahydroborate (15.1 mg, 0.398 mmol) was added in small portion to this stirring solution at room temperature. As more and more NaBH₄ was added, a precipitate formed. Upon complete addition of NaBH₄, the suspension was allowed to stir at room temperature for 30 minutes. A solution of (5R)-4-(3-(1-(4-chlorophenyl)-2-nitroethyl)-1H-indol-6-yl)-5-methyl-6,7-dihydro-5H-cyclopenta[d]pyrimidine (115 mg, 0.266 mmol) in MeOH (2 mL) was added to this stirring suspension. Sodium tetrahydroborate (35.2 mg, 0.930 mmol) was carefully added in small portions to this stirring suspension. The reaction mixture was stirred for 1 hour at room temperature. The reaction mixture was filtered thru celite, and the filtrate was treated with aqueous NH₄OH (10 mL, 20% solution NH₄OH). The filtrate was then extracted with CHCl₃ (4×10 mL). The combined organics were dried (Na₂SO₄), filtered and concentrated. Crude 2-(4-chlorophenyl)-2-(6-((R)-5-methyl-6,7-dihydro-5H-cyclopenta[d]pyrimidin-4-yl)-1H-indol-3-yl)ethanamine was carried to next step. LCMS: M+1 403.5.

Step 4: Acetone (0.0195 mL, 0.266 mmol) was added to a solution of 2-(4-chlorophenyl)-2-(6-((R)-5-methyl-6,7-dihydro-5H-cyclopenta[d]pyrimidin-4-yl)-1H-indol-3-yl)ethanamine (107 mg, 0.266 mmol) and N,N-diisopropylethylamine (0.139 mL, 0.797 mmol) in methylene chloride (2.0 mL). The reaction mixture was stirred for 10 minutes, and then sodium triacetoxyborohydride (0.0188 g, 0.0885 mmol) was added. After stirring for 2.5 hours, saturated NaHCO₃ was added, and the mixture was stirred vigorously 10 minutes. The mixture was extracted with DCM (3×10 mL). The combined organic were dried (Na₂SO₄), filtered and concentrated. The crude product was purified by SFC chiral chromatography (Chiral OJH (21.2×250 mm) 25% methanol+0.1% TEA) to give N—((R)-2-(4-chlorophenyl)-2-(6-((R)-5-methyl-6,7-dihydro-5H-cyclopenta[d]pyrimidin-4-yl)-1H-indol-3-yl)ethyl)propan-2-amine (19.8 mg, 16.8%) as the first peak. LCMS: M+1 445.3. ¹H NMR (CDCl₃, 400 MHz) δ 11.16 (s, 1H), 8.93 (s, 1H), 7.93 (s, 1H), 7.49-7.46 (m, 3H), 7.38 (d, J=8.4 Hz, 2H), 7.31 (d, J=8.5 Hz, 2H), 4.36 (t, 1H), 3.89 (m, 1H), 3.23 (m, 1H), 3.14-2.99 (m, 2H), 2.94-2.86 (m, 1H), 2.77 (m, 1H), 2.34 (m, 1H), 1.68 (m, 1H), 0.96 (d, 6H), 0.92 (d, 3H).

Example 7

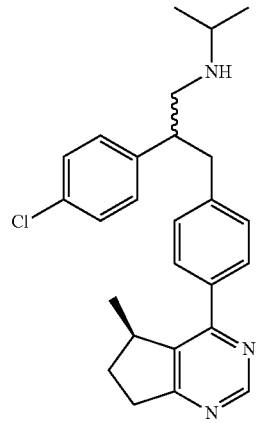

(R)—N-(2-(4-chlorophenyl)-2-(4-(5-methyl-6,7-dihydro-5H-cyclopenta[d]pyrimidin-4-yl)phenoxy)ethyl)propan-2-amine Step 1: 2-Propanamine (1.71 mL, 20.0 mmol) was added to a mixture of 2-(4-chlorophenyl)oxirane (2.69 g, 16.7 mmol) and water (6.67 mL). The mixture was stirred at room temperature. After 24 hours, additional 2-propanamine (1.13 mL, 13.3 mmol) was added. After a total of 40 hours, water (15 mL) was added. The contents were extracted with ether (4×50 mL). The combined ether solutions were dried (Na₂SO₄). After filtration and evaporation of solvents, the material was dissolved in methylene chloride (100 mL) Di-tert-butyldicarbonate (4.01 g, 18.4 mmol) was added, followed by triethylamine (2.56 mL, 18.4 mmol). The mixture was stirred at room temperature for 20 hours. More Boc₂O (2 g) was added. After 4 hours, imidazole (1.136 g, 16.68 mmol) was added. After 20 minutes, the contents were diluted with DCM (50 mL), washed with 1.0M NaH₂PO₄ (2×50 mL), and dried (Na₂SO₄). The crude was purified by flash chromatography to give tert-butyl 2-(4-chlorophenyl)-2-hydroxyethyl(isopropyl)carbamate (3.32 g, 63%).

Step 2: (R)-4-chloro-5-methyl-6,7-dihydro-5H-cyclopenta[d]pyrimidine (137 mg, 0.812 mmol) and 4-hydroxybenzeneboronic acid (123 mg, 0.894 mmol) was dissolved in isopropyl alcohol (1.6 mL). Sodium carbonate in water (0.97 mL, 1.0M) was added slowly, followed by bis(triphenylphosphine)palladium chloride (26.5 mg, 0.0378 mmol). The mixture was stirred at 100° C. (bath) for 16 hours. The contents were diluted with water (5 mL) and EtOAc (10 mL). The aqueous layer was separated and extracted with EtOAc (2×5 mL). The combined EtOAc solutions were washed with brine (5 mL) and dried (Na₂SO₄). The crude was purified by flash chromatography to give (R)-4-(5-methyl-6,7-dihydro-5H-cyclopenta[d]pyrimidin-4-yl)phenol (160 mg, 87%) as viscous oil which solidified upon standing.

Step 3: Diethyl azodicarboxylate (0.166 mL, 1.05 mmol) was added slowly to a solution of tert-butyl 2-(4-chlorophenyl)-2-hydroxyethyl(isopropyl)carbamate (265 mg, 0.843 mmol), (R)-4-(5-methyl-6,7-dihydro-5H-cyclopenta[d]pyrimidin-4-yl)phenol (159 mg, 0.703 mmol), and triphenylphosphine (276 mg, 1.05 mmol) in tetrahydrofuran (7.0 mL) at −30° C. (bath). The mixture was allowed to warm up to room temperature and stirred overnight. Most of the starting material remained. Triphenylphosphine (276 mg, 1.05 mmol) was added. The contents were cooled at −30° C. Diethyl azodicarboxylate (0.166 mL, 1.05 mmol) was added. The mixture was stirred at room temperature for 4 hours. tert-Butyl 2-(4-chlorophenyl)-2-hydroxyethyl(isopropyl) carbamate (265 mg, 0.843 mmol) was added. The mixture was stirred at room temperature overnight. EtOAC (10 mL) and water (10 mL) were added. The organic layer was separated. The aqueous layer was extracted with EtOAc (2×10 mL). The combined organic solutions were dried (Na$_2$SO$_4$). The crude was purified by flash chromatography to give (R)-tert-butyl 2-(4-chlorophenyl)-2-(4-(5-methyl-6,7-dihydro-5H-cyclopenta[d]pyrimidin-4-yl)phenoxy)ethyl(isopropyl) carbamate (26 mg, 7%).

Step 4: Trifluoroacetic acid (0.5 mL) was added dropwise to a solution of (R)-tert-butyl 2-(4-chlorophenyl)-2-(4-(5-methyl-6,7-dihydro-5H-cyclopenta[d]pyrimidin-4-yl)phenoxy)ethyl(isopropyl)carbamate (26 mg, 0.0498 mmol) in methylene chloride (1.0 mL) at 0° C. The mixture was stirred at 0° C. for 10 minutes and then at room temperature for 2 hours. The contents were concentrated. The resulting residue was purified by reverse-phase HPLC to give (R)—N-(2-(4-chlorophenyl)-2-(4-(5-methyl-6,7-dihydro-5H-cyclopenta[d]pyrimidin-4-yl)phenoxy)ethyl)propan-2-amine as TFA salt (7.5 mg, 23%). $^1$H NMR (d6-DMSO, 500 MHz) δ (ppm): 8.9 (s, 1H), 8.7 (s, br, 2H), 7.8 (t, 2H), 7.5 (m, 4H), 7.1 (d, 2H), 5.7 (d, 1H), 3.8 (m, 1H), 3.4-3.5 (m, 2H), 3.3-3.4 (m, 1H), 3.0-3.1 (m, 1H), 2.9 (m, 1H), 2.3 (m, 1H), 1.7 (m, 1H), 1.3 (dd, 6H), 0.9 (dd, 3H). MS (422.3, M+1).

Example 8

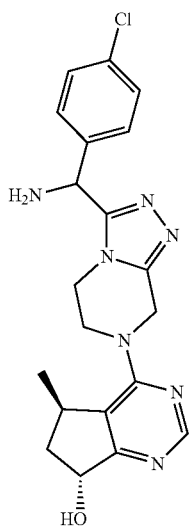

(5R,7R)-4-(3-(Amino(4-chlorophenyl)methyl)-5,6-dihydro-[1,2,4]triazolo[4,3-a]pyrazin-7(8H)-yl)-5-methyl-6,7-dihydro-5H-cyclopenta[d]pyrimidin-7-ol Step 1: 1,1-Carbonyldiimidazole (1.60 g, 9.89 mmol) was added to a solution of 2-(tert-butoxycarbonylamino)-2-(4-chlorophenyl)acetic acid (2.57 g, 9.00 mmol) in CH$_2$Cl$_2$ (22.5 mL, 9.00 mmol), and the mixture was stirred for 30 minutes until gas evolution ceased. Hydrazine (0.367 mL, 11.7 mmol) was then added to this solution, and the mixture was stirred at room temperature for 12 hours. The reaction mixture was diluted with CH$_2$Cl$_2$ and washed with NaHCO$_3$ (10%). The organic layer was dried (Na$_2$SO$_4$) and concentrated. The residue was purified by reversed-phase chromatography (Biotage SP4, 40+M, C$_{18}$, 25% to 100% MeCN/H$_2$O). Fractions containing product were poured into a separatory funnel and extracted with ethyl acetate (3×). The combined organic layers were dried and concentrated to give tert-butyl 1-(4-chlorophenyl)-2-hydrazinyl-2-oxoethylcarbamate as a solid (1.95 g, 72%). LCMS (APCI$^+$) M+H$^+$: 299 (5%); M+H$^+$-Boc: 199 (100%); rt=2.78 minutes. $^1$H NMR (400 MHz, CDCl$_3$) δ 7.73 (s, 1H), 7.30 (s, 4H), 5.85 (d, J=6.6 Hz, 1H), 5.21 (s, 1H), 3.87 (s, 2H), 1.42 (s, 9H).

Step 2: Triethyloxonium hexafluorophosphate (3.20 g, 28.0 mmol) was added to a solution of tert-butyl 3-oxopiperazine-1-carboxylate (2.54 g, 12.7 mmol) in CH$_2$CL$_2$ (31.7 mL) at 0° C., and the resulting solution was stirred at room temperature for 18 hours. The reaction mixture was washed with saturated NaHCO$_3$, dried (Na$_2$SO$_4$), and concentrated to give tert-butyl 3-ethoxy-5,6-dihydropyrazine-1(2H)-carboxylate as an oil. LCMS (APCI$^+$) M+H-t-Bu: 173 (40%); rt=3.14 minutes.

Step 3: A solution of tert-butyl 3-ethoxy-5,6-dihydropyrazine-1(2H)-carboxylate (0.762 g, 3.34 mmol) and tert-butyl 1-(4-chlorophenyl)-2-hydrazinyl-2-oxoethylcarbamate (1.00 g, 3.34 mmol) in toluene (6.67 mL, 3.34 mmol) was heated to reflux and stirred at this temperature for 1 hour. The reaction mixture was cooled to room temperature, diluted with ethyl acetate, and washed with water. The organic layer was dried and concentrated to give a residue that was purified by reverse phase chromatography (Biotage SP4, 40+M, C$_{18}$, 10% to 100% ACN/H$_2$O) to afford tert-butyl 3-((tert-butoxycarbonylamino)(4-chlorophenyl)methyl)-5,6-dihydro-[1,2,4]triazolo[4,3-a]pyrazine-7(8H)-carboxylate (0.92 g, 60%). LCMS (APCI$^+$) M+H$^+$: 463 (25%), 464 (90%), 466 (25%), 467 (5%); rt=3.56 minutes. $^1$H NMR (400 MHz, CDCl$_3$) δ 7.33 (d, J=8.6 Hz, 1H), 7.29 (d, J=8.6 Hz, 1H), 6.12 (d, J=7.8 Hz, 1H), 5.87 (d, J=7.8 Hz, 1H), 4.84 (d, J=17.6 Hz, 1H), 4.75 (d, J=17.6 Hz, 1H), 3.93 (m, 1H), 3.80 (m, 1H), 3.73 (m, 1H), 3.49 (m, 1H), 1.47 (s, 9H), 1.41 (s, 9H).

Step 4: A solution of tert-butyl 3-((tert-butoxycarbonylamino)(4-chlorophenyl)methyl)-5,6-dihydro-[1,2,4]triazolo[4,3-a]pyrazine-7(8H)-carboxylate (0.652 g, 1.41 mmol) in MeOH (7.03 mL, 1.41 mmol) was saturated with HCl (g). The reaction mixture was stirred at room temperature for 30 minutes and then concentrated in vacuo to afford (4-chlorophenyl)(5,6,7,8-tetrahydro-[1,2,4]triazolo[4,3-a]pyrazin-3-yl)methanamine bishydrochloride as a foam (0.47 g, 99%). LCMS (APCI$^+$) M+H$^+$: 264 (50%), 266 (10%), 267 (3%); rt=1.76 minutes. $^1$H NMR (400 MHz, d$_6$-DMSO) δ 10.62 (s, 1H), 10.18 (s, 1H), 9.43 (s, 3H), 7.57 (d, J=8.6 Hz, 2H), 7.53 (d, J=8.6 Hz, 2H), 6.13 (m, 1H), 4.51 (m, 2H), 4.44 (m, 1H), 3.56 (m, 3H).

Step 5: A solution of (4-chlorophenyl)(5,6,7,8-tetrahydro-[1,2,4]triazolo[4,3-a]pyrazin-3-yl)methanamine bishydrochloride (50 mg, 0.149 mmol), (5R,7R)-4-chloro-5-methyl-6,7-dihydro-5H-cyclopenta[d]pyrimidin-7-yl 4-nitrobenzoate (49.8 mg, 0.149 mmol) and DIEA (0.130 mL, 0.745 mmol) in NMP (0.30 mL, 0.149 mmol) was heated at 100° C. for 1 day. The crude reaction mixture was diluted with methanol and filtered. The filtrate was purified (C18, 5-95% MeCN/H$_2$O+1% TFA). The fractions containing product were isolated by basifying with 25% NaOH and extracting into CH$_2$Cl$_2$/isopropanol (3:1). The organic layers were concentrated, and the residue was diluted with methanol. The solution was saturated with HCl (g). The solution was evaporated to give (5R,7R)-4-(3-(Amino(4-chlorophenyl)methyl)-5,6-dihydro-[1,2,4]triazolo[4,3-a]pyrazin-7(8H)-yl)-5-methyl-6,7-dihydro-5H-cyclopenta[d]pyrimidin-7-ol bishydrochloride (15.3 mg, 25%). LCMS (APCI+) rt=2.28 min. ¹H NMR (400 MHz, d₆-DMSO+3 drops D₂O) δ 8.83 (d, J=7.8 Hz, 1H), 7.55 (s, 4H), 6.02 (d, J=8.6 Hz, 1H), 5.30 (m, 1H), 4.54 (m, 1H), 4.36 (m, 1H), 4.24 (m, 1H), 4.09 (m, 1H), 3.48 (m, 1H), 2.21 (, 1H), 2.08 (m, 1H), 1.26 (m, 1H), 1.19 (m, 3H).

Example 9

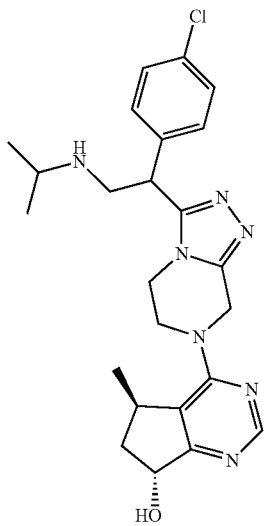

(5R,7R)-4-(3-(1-(4-Chlorophenyl)-2-(isopropylamino)ethyl)-5,6-dihydro-[1,2,4]triazolo[4,3-a]pyrazin-7(8H)-yl)-5-methyl-6,7-dihydro-5H-cyclopenta[d]pyrimidin-7-ol Step 1: Using the procedure from Example 8, Step 1,3-(tert-butoxycarbonyl)isopropyl)amino)-2-(4-chlorophenyl)propanoic acid (2.00 g, 5.85 mmol) was used to afford tert-butyl 2-(4-chlorophenyl)-3-hydrazinyl-3-oxopropyl(isopropyl)carbamate (1.90 g, 5.34 mmol, 91%). LCMS (APCI+) M+H⁺: 356 (100%), 358 (50%), rt 3.50 minutes.

Step 2: Using the procedure from Example 8, Step 3, tert-butyl 2-(4-chlorophenyl)-3-hydrazinyl-3-oxopropyl(isopropyl)carbamate (1.90 g, 5.34 mmol) was used to afford tert-butyl 3-(2-(tert-butoxycarbonyl(isopropyl)amino)-1-(4-chlorophenyl)ethyl)-5,6-dihydro-[1,2,4]triazolo[4,3-a]pyrazine-7(8H)-carboxylate (1.66 g, 3.18 mmol, 60%). LCMS (APCI+) M+H⁺: 519 (66%), 520 (95%), rt 4.09 minutes.

Step 3: Using the procedure from Example 8, Step 4, tert-butyl 3-(2-(tert-butoxycarbonyl(isopropyl)amino)-1-(4-chlorophenyl)ethyl)-5,6-dihydro-[1,2,4]triazolo[4,3-a]pyrazine-7(8H)-carboxylate (1.66 g, 3.18 mmol) was used to afford N-(2-(4-chlorophenyl)-2-(5,6,7,8-tetrahydro-[1,2,4]triazolo[4,3-a]pyrazin-3-yl)ethyl)propan-2-amine bishydrochloride (0.65 g, 1.66 mmol, 52%). LCMS (APCI+) M+H⁺: 320 (100%), 322 (25%), rt 1.89 minutes.

Step 4: Using the procedure from Example 8, Step 5, N-(2-(4-chlorophenyl)-2-(5,6,7,8-tetrahydro-[1,2,4]triazolo[4,3-a]pyrazin-3-yl)ethyl)propan-2-amine bishydrochloride (95 mg, 0.15 mmol) was used to afford (5R,7R)-4-(3-(1-(4-chlorophenyl)-2-(isopropylamino)ethyl)-5,6-dihydro-[1,2,4]triazolo[4,3-a]pyrazin-7(8H)-yl)-5-methyl-6,7-dihydro-5H-cyclopenta[d]pyrimidin-7-ol bishydrochloride (20 mg, 0.042 mmol, 28%). LCMS APCI+ (M+H⁺): rt 2.20 minutes. HPLC purity at 254 nm 98%, rt=1.82 minutes. ¹H NMR (400 MHz, d₆-DMSO+2 drops D₂O) δ 8.81 (d, J=6.6 Hz, 1H), 7.47 (d, J=8.2 Hz, 2H), 7.40 (dd, J=8.6 Hz, 3.5 Hz, 2H), 5.48 (dd, J=29, 16 Hz, 1H), 5.32 (td, J=8.2, 2.0 Hz, 1H), 5.21 (dd, J=32, 17 Hz, 1H), 4.84 (q, J=7 Hz, 1H), 4.31 (m, 2H), 3.84 (m, 1H), 3.71 (m, 1H), 3.43 (m, 4H), 2.23 (dd, J=12, 8.2 Hz, 1H), 2.12 (m, 1H), 1.26 (d, J=6.6 Hz, 6H), 1.16 (t, J=7.5 Hz, 3H).

Example 10

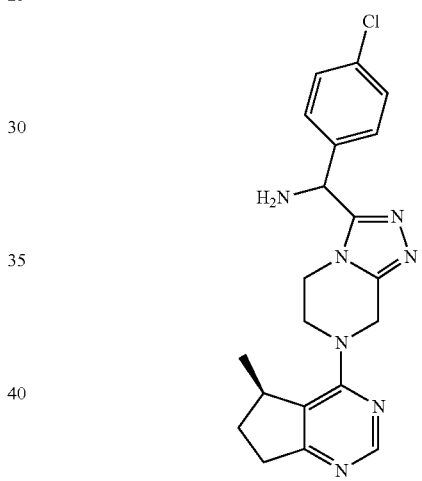

(4-Chlorophenyl)(7-((R)-5-methyl-6,7-dihydro-5H-cyclopenta[d]pyrimidin-4-yl)-5,6,7,8-tetrahydro-[1,2,4]triazolo[4,3-a]pyrazin-3-yl)methanamine Using the procedure from Example 8, Step 5, using (R)-4-chloro-5-methyl-6,7-dihydro-5H-cyclopenta[d]pyrimidine and (4-chlorophenyl)(5,6,7,8-tetrahydro-[1,2,4]triazolo[4,3-a]pyrazin-3-yl)methanamine bishydrochloride (100 mg, 0.30 mmol) to afford (4-chlorophenyl)(7-((R)-5-methyl-6,7-dihydro-5H-cyclopenta[d]pyrimidin-4-yl)-5,6,7,8-tetrahydro-[1,2,4]triazolo[4,3-a]pyrazin-3-yl)methanamine bishydrochloride (75 mg, 0.19 mmol, 64%): LCMS APCI+ (M+H⁺): 396 (60%), 398 (20%), rt 2.48 min. HPLC purity at 254 nm>99%, rt=1.68 min. ¹H NMR (400 MHz, d₆-DMSO) □ 9.51 (s, 3H), 8.85 (d, J=9.4 Hz, 1H), 7.61 (d, J=7.0 Hz, 2H), 7.55 (d, J=7.8 Hz, 2H), 6.08 (br d, J=9.0 Hz, 1H), 5.42 (dd, J=26 Hz, 16 Hz, 1H), 5.19 (dd, J=21 Hz, 18 Hz, 1H), 4.55 (m, 1H), 4.29 (m, 1H), 3.79 (m, 1H), 3.14 (m, 1H), 2.96 (m, 1H), 2.32 (m, 1H), 1.82 (m, 1H), 1.15 (t, J=6.8 Hz, 2H), 1.04 (d, J=6.2 Hz, 3H).

Example 11

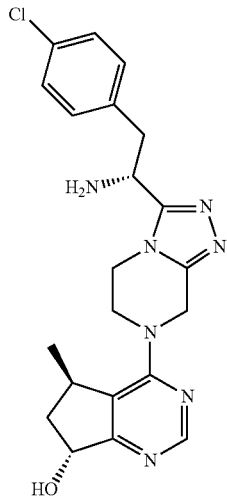

(5R,7R)-4-(3-((R)-1-Amino-2-(4-chlorophenyl) ethyl)-5,6-dihydro-[1,2,4]triazolo[4,3-a]pyrazin-7 (8H)-yl)-5-methyl-6,7-dihydro-5H-cyclopenta[d] pyrimidin-7-ol Step 1: Using the procedure from Example 8, Step 1, (R)-2-(tert-butoxycarbonylamino)-3-(4-chlorophenyl)propanoic acid (3.02 g, 10.0 mmol) was used to afford (R)-tert-butyl 3-(4-chlorophenyl)-1-hydrazinyl-1-oxopropan-2-ylcarbamate (3.16 g, 10.0 mmol, >99%). LCMS APCI+ (M+H$^+$): 314 (95%), 316 (40%), rt 2.92 minutes.

Step 2: Using the procedure from Example 8, Steps 2 and 3, (R)-tert-butyl 3-(4-chlorophenyl)-1-hydrazinyl-1-oxopropan-2-ylcarbamate (3.16 g, 10.0 mmol) was used to afford (R)-tert-butyl 3-(1-(tert-butoxycarbonylamino)-2-(4-chlorophenyl)ethyl)-5,6-dihydro-[1,2,4]triazolo[4,3-a]pyrazine-7(8H)-carboxylate (4.03 g, 8.43 mmol, 84%). LCMS APCI+ (M+H$^+$): 477 (20%), 478 (80%), 479 (20%), rt 3.63 minutes.

Step 3: Using the procedure from Example 8, Step 4, (R)-tert-butyl 3-(1-(tert-butoxycarbonylamino)-2-(4-chlorophenyl)ethyl)-5,6-dihydro-[1,2,4]triazolo[4,3-a]pyrazine-7(8H)-carboxylate (4.03 g, 8.43 mmol) was used to afford (R)-2-(4-chlorophenyl)-1-(5,6,7,8-tetrahydro-[1,2,4]triazolo[4,3-a]pyrazin-3-yl)ethanamine bishydrochloride (2.47 g, 7.06 mmol, 84%). LCMS APCI+ (M+H$^+$): 278 (100%), rt 1.91 minutes. $^1$H NMR (400 MHz, d$_6$-DMSO) δ 10.57 (br s, 1H), 10.43 (br s, 1H), 9.05 (br s, 3H), 7.33 (d, J=8.6 Hz, 2H), 7.20 (d, J=8.6 Hz, 2H), 4.95 (br s, 1H), 4.52 (m, 3H), 3.92 (m, 1H), 3.51 (m, 2H), 3.38 (m, 2H).

Step 4: Using the procedure from Example 8, Step 5, (R)-2-(4-chlorophenyl)-1-(5,6,7,8-tetrahydro-[1,2,4]triazolo[4,3-a]pyrazin-3-yl)ethanamine bishydrochloride (66 mg, 0.114 mmol) was used to afford (5R,7R)-4-(3-((R)-1-amino-2-(4-chlorophenyl)ethyl)-5,6-dihydro-[1,2,4]triazolo[4,3-a]pyrazin-7(8H)-yl)-5-methyl-6,7-dihydro-5H-cyclopenta[d]pyrimidin-7-ol hydrochloride (49 mg, 0.046 mmol, 40%). LCMS APCI+ (M+H$^+$): 426 (100%), 428 (20%), rt 2.17 minutes. HPLC purity at 254 nm>99%, rt=1.73 minutes. $^1$H NMR (400 MHz, d$_6$-DMSO) δ 8.98 (s, 3H), 8.85 (s, 1H), 7.30 (d, J=7.8 Hz, 2H), 7.15 (d, J=8.2 Hz, 2H), 5.30 (m, 1H), 5.23 (s, 2H), 4.85 (br s, 1H), 4.35 (m, 1H), 4.00 (m, 1H), 3.76 (m, 1H), 3.70 (s, 1H), 3.61 (s, 1H), 3.51 (m, 1H), 3.40 (m, 1H), 3.27 (m, 1H), 2.16 (m, 2H), 1.15 (d, J=7.0 Hz, 3H).

Example 12

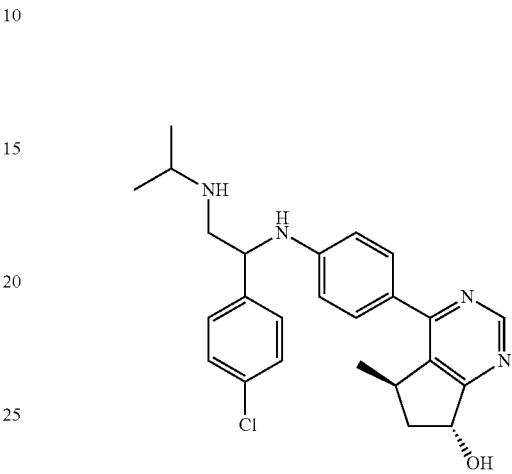

(5R,7R)-4-(4-(1-(4-Chlorophenyl)-2-(isopropylamino)ethylamino)phenyl)-5-methyl-6,7-dihydro-5H-cyclopenta[d]pyrimidin-7-ol hydrochloride Step 1: TMSCN (19.9 mL, 149 mmol) was added to a solution of 4-chlorobenzaldehyde (20.0 g, 142 mmol), 4-bromoaniline (25.1 g, 146 mmol), and sulfamic acid (0.691 g, 7.11 mmol) in MeOH (56.9 mL), and the reaction mixture was stirred at room temperature for 6 hours. The reaction mixture was filtered, and the filter cake was washed with ethanol, affording 2-(4-bromophenylamino)-2-(4-chlorophenyl)acetonitrile as a solid (38.0 g, 83%). $^1$H NMR (400 MHz, d$_6$-DMSO) δ 7.53 (d, J=8.2 Hz, 2H), 7.44 (d, J=8.6 Hz, 2H), 7.37 (d, J=9.0 Hz, 2H), 6.64 (d, J=9.0 Hz, 2H), 5.38 (d, J=9.0 Hz, 1H), 4.06 (d, J=9.0 Hz, 1H).

Step 2: Lithium aluminum hydride (52.9 mL, 52.9 mmol) in THF (1.0M) was added to a solution of 2-(4-bromophenylamino)-2-(4-chlorophenyl)acetonitrile (20.0 g, 62.2 mmol) in THF (311 mL, 62.2 mmol) at −78° C. The reaction was allowed to stir at −78° C. and gradually warmed to room temperature over 4 hours. The reaction mixture was poured into 1N HCl. The solution was then basified and extracted with ethyl acetate (3×). The combined organic layers were washed with brine, dried and concentrated to give an oil. This residue was purified by column chromatography, eluting first with ethyl acetate/hexanes (2:1) then 5% MeOH/CH$_2$Cl$_2$-> 10% MeOH/CH$_2$Cl$_2$+1% NH$_4$OH, affording N1-(4-bromophenyl)-1-(4-chlorophenyl)ethane-1,2-diamine as an oil (9.60 g, 49%). $^1$H NMR (400 MHz, CD$_3$OD) δ 7.38 (d, 2H), 7.34 (d, 2H), 7.15 (d, 2H), 6.53 (d, 2H), 4.59 (dd, J=9.8, 4.7 Hz, 1H), 3.14 (dd, J=12.9, 4.7 Hz, 1H), 3.05 (dd, J=12.9, 9.4 Hz, 1H).

Step 3: NaBH(OAc)$_3$ (4.88 g, 23.0 mmol) was added to a solution of N1-(4-bromophenyl)-1-(4-chlorophenyl)ethane-1,2-diamine (5.00 g, 15.4 mmol) and propan-2-one (1.24 mL, 16.9 mmol) in 1,2-dichloroethane (51.2 mL, 15.4 mmol), and the resulting solution was stirred at room temperature for 12 hours. The reaction was followed by LCMS. The reaction mixture was quenched with saturated NaHCO₃ and extracted with ethyl acetate (3 X). The combined organic layers were dried and concentrated to give the desired product as an oil, which was not further purified (5.40 g, 95%). ¹H NMR (400 MHz, CDCl₃) δ 7.38 (d, J=9.0 Hz, 2H), 7.34 (d, J=9.0 Hz, 2H), 7.15 (d, J=9.0 Hz, 2H), 6.53 (d, J=9.0 Hz, 2H), 4.59 (m, 1H), 3.10 (m, 2H).

Step 4: A mixture of N1-(4-bromophenyl)-1-(4-chlorophenyl)-N-2-isopropylethane-1,2-diamine (0.556 g, 1.51 mmol), 4,4,4',4',5,5,5',5'-octamethyl-2,2'-bi(1,3,2-dioxaborolane) (0.576 g, 2.27 mmol), KOAc (0.594 g, 6.05 mmol) and DMSO (7.56 mL, 1.51 mmol) was degassed with nitrogen for 5 minutes. PdCl₂(dppf)*CH₂Cl₂ (0.062 g, 0.076 mmol) was then added to this solution, and the reaction was heated at 80° C. overnight under nitrogen. After 1 day, additional 4,4,4',4', 5,5,5',5'-octamethyl-2,2'-bi(1,3,2-dioxaborolane) (1.15 g, 4.54 mmol), KOAc (1.19 g, 12.1 mmol) and PdCl₂(dppf)* CH₂Cl₂ (0.124 g, 0.152 mmol) was added, and the reaction was heated at 80° C. for an additional 24 hours. The reaction mixture was diluted with ethyl acetate to precipitate inorganic salts. The slurry was filtered to remove the salts, and the filtrate was concentrated and loaded directly onto a C₁₈ samplet (40+M) and eluted on a Biotage Horizon (10%-100% ACN/H₂O+1% iPA, 1 mM NH₄OAc). The column fractions containing product were poured into a separatory funnel, basified with 1N NaOH and extracted with ethyl acetate. The combined organic layers were dried with sodium sulfate and concentrated to afford the product as a foam (0.220 g, 35%). LCMS APCI+ (M+H⁺): 415 (25%), 417 (10%), rt 3.76 minutes.

Step 5: 1-(4-Chlorophenyl)-N2-isopropyl-N1-(4-(4,4,5,5-tetramethyl-1,3,2-dioxaborolan-2-yl)phenyl)ethane-1,2-diamine (0.075 g, 0.181 mmol), Pd(PPh₃)₄ (0.017 g, 0.015 mmol), and 2N Na₂CO₃ (0.226 mL, 0.452 mmol) were added to a solution of (5R,7R)-4-chloro-5-methyl-6,7-dihydro-5H-cyclopenta[d]pyrimidin-7-yl 4-nitrobenzoate (0.050 g, 0.151 mmol) in n-propanol (0.464 mL, 0.151 mmol). The suspension was degassed by bubbling nitrogen through the solution. The dark suspension was heated at 90° C. for 14 hours. The mixture was cooled to room temperature and then concentrated. The resulting residue was diluted with ethyl acetate and filtered. The filtrate was washed with saturated NaHCO₃ and brine. The organic layer was dried and concentrated. The resulting residue was purified by Biotage SP4 (C₁₈, 25+0-100% ACN). The product-containing fractions were collected and repurified by Gilson C₁₈ (5-95 ACN/H₂O+1% TFA). Tubes containing product were identified by LCMS, collected and evaporated. The material was partially dissolved in CH₂Cl₂, and HCl (g) was bubbled through the mixture to precipitate solid (5R,7R)-4-(4-(1-(4-chlorophenyl)-2-(isopropylamino)ethylamino)phenyl)-5-methyl-6,7-dihydro-5H-cyclopenta[d]pyrimidin-7-ol hydrochloride (8.10 mg, 12%). LCMS APCI+ (M+H⁺): 437 (100%), 439 (30%), rt 2.55 minutes. HPLC purity at 254 nm>99%, rt=2.17 minutes. ¹H NMR (400 MHz, d₆-acetone) δ 8.88 (s, 1H), 7.81 (d, J=8.2 Hz, 1H), 7.78 (d, J=8.6 Hz, 1H), 7.59 (d, J=3.5 Hz, 1H), 7.58 (d, J=3.1 Hz, 1H), 7.40 (d, J=8.2 Hz, 2H), 6.65 (t, J=9.0 Hz, 2H), 5.26 (m, 1H), 5.15 (td, J=7.4, 4.3 Hz, 1H), 3.88 (m, 2H), 3.62 (br s, 2H), 3.50 (br s, 1H), 2.17 (m, 2H), 1.45 (m, 2H), 1.41 (d, J=6.6 Hz, 6H), 1.10 (t, J=7.0 Hz, 3H), 0.88 (m, 1H).

Example 13

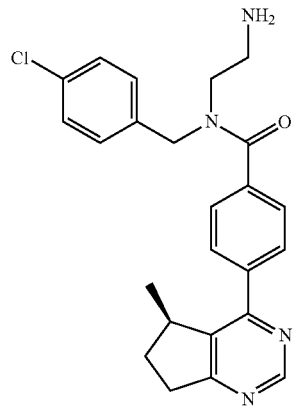

(R)—N-(2-aminoethyl)-N-(4-chlorobenz)-4-(5-methyl-6,7-dihydro-5H-cyclopenta[d]pyrimidin-4-yl)benzamide Step 1: A solution of Na₂CO₃ (1.65 mL, 1M) was added to a solution of (R)-4-chloro-5-methyl-6,7-dihydro-5H-cyclopenta[d]pyrimidine (253 mg, 1.50 mmol) and 4-methoxycarbonylphenylboronic acid (297 mg, 1.65 mmol) in 1,4-dioxane (4.5 mL). The mixture was sparged with N₂ for 2 minutes. The catalyst Pd(dppf)Cl₂ (98 mg, 0.12 mmol) was added in one portion. The reaction vial was sealed and heated in microwave to 110° C. for 30 minutes. Water (20 mL) was added to the mixture and extracted with DCM (3×15 mL). The combined organics were dried (Na₂SO₄), filtered and concentrated. The crude product was purified by flash chromatography (0-50% EtOAc/hexane gradient elution) to give (R)-methyl 4-(5-methyl-6,7-dihydro-5H-cyclopenta[d]pyrimidin-4-yl)benzoate as an oil (300 mg, 70%). ¹H NMR (CDCl₃, 500 MHz) δ 9.07 (s, 1H), 8.16 (d, =8.5 Hz, 2H), 7.88 (d, J=8.5 Hz, 2H), 3.96 (s, 3H), 3.81-3.76 (m, 1H), 3.15-3.00 (m, 2H), 2.44-2.40 (m, 1H), 1.78-1.74 (m, 1H), 1.01 (d, J=6.5 Hz, 3H).

Step 2: A solution of LiOH (64 mg, 2.68 mmol) in H₂O (10 mL) was added to a solution of (R)-methyl 4-(5-methyl-6,7-dihydro-5H-cyclopenta[d]pyrimidin-4-yl)benzoate (359 mg, 1.34 mmol) in THF (6 mL) at 0° C. The mixture was allowed to warm up to room temperature and stirred overnight. The volatile solvent was removed in vacuo. The aqueous layer was acidified with 1N HCl to a pH of 3. A solid precipitated, and was collected by filtration, washed with ether, and dried in vacuo to give (R)-4-(5-methyl-6,7-dihydro-5H-cyclopenta[d]pyrimidin-4-yl)benzoic acid as a solid (306 mg, 90%).

Step 3: DIPEA (37 μL, 0.21 mmol) and O-(benzotriazol-1-yl)-N,N,N',N'-tetramethyluronium hexafluorophosphate (80 mg, 0.21 mmol) were added to a solution of (R)-4-(5-methyl-6,7-dihydro-5H-cyclopenta[d]pyrimidin-4-yl)benzoic acid (51 mg, 0.2 mmol) in DMF (1 mL). The mixture was heated to 70° C. for 18 hours. The mixture was diluted with DCM (10 mL). Saturated NH₄Cl (10 mL) was added. The layers were separated. The aqueous layer was extracted with DCM (2×10 mL). The combined organics were dried (Na₂SO₄), filtered and concentrated. The crude product was purified by flash chromatography (0-100% EtOAc/hexane gradient elution) to give (R)-tert-butyl 2-(N-(4-chlorobenzyl)-4-(5-methyl-6,7-dihydro-5H-cyclopenta[d]pyrimidin-4-yl)benzamido)ethylcarbamate as an oil (49 mg, 31%).

Step 4: TFA (182 µL, 2.36 mmol) was added to a solution of (R)-tert-butyl 2-(N-(4-chlorobenzyl)-4-(5-methyl-6,7-dihydro-5H-cyclopenta[d]pyrimidin-4-yl)benzamido)ethylcarbamate (49 mg, 0.094 mmol) in DCM (1 mL). The mixture was stirred at room temperature for 1.5 hours. The mixture was concentrated in vacuo. The crude product was purified by reverse phase HPLC to give (R)—N-(2-aminoethyl)-N-(4-chlorobenzyl)-4-(5-methyl-6,7-dihydro-5H-cyclopenta[d]pyrimidin-4-yl)benzamide as an oil (9 mg, 22%). MS (APCI+) [M+H]$^+$421.2. $^1$H NMR (D$_2$O, 500 MHz) δ 9.09 (s, 1H), 7.81 (d, J=8.5 Hz, 2H), 7.63 (d, J=8.0 Hz, 2H), 7.35 (d, J=8.5 Hz, 2H), 7.15 (D, J=8.0 Hz, 2H), 4.63 (s, 2H), 3.87 (t, J=6.5 Hz, 2H), 3.82-3.79 (m, 1H), 3.26-3.11 (m, 4H), 2.63 (s, 2H), 2.50-2.42 (m, 1H), 1.86-1.81 (m, 1H), 0.86 (s, J=7.00 Hz, 3H).

Example 14

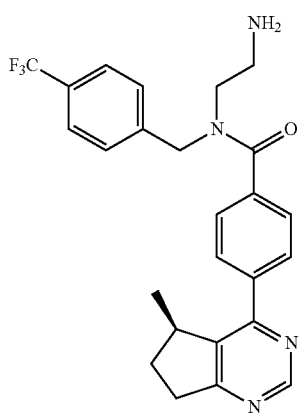

(R)—N-(2-aminoethyl)-N-(4-trifluoromethylbenzyl)-4-(5-methyl-6,7-dihydro-5H-cyclopenta[d]pyrimidin-4-yl)benzamide (R)—N-(2-Aminoethyl)-N-(4-trifluoromethylbenzyl)-4-(5-methyl-6,7-dihydro-5H-cyclopenta[d]pyrimidin-4-yl)benzamide was prepared in a similar manner as (R)—N-(2-aminoethyl)-N-(4-chlorobenzyl)-4-(5-methyl-6,7-dihydro-5H-cyclopenta[d]pyrimidin-4-yl)benzamide. MS (APCI+) [M+H]$^+$455.2. $^1$H NMR (D$_2$O, 500 MHz) δ 8.86 (s, 1H), 7.77-7.96 (m, 4H), 7.56 (d, J=8.0 Hz, 2H0, 7.35 (d, J=8.0 Hz, 2H), 4.75 (s, 2H), 3.84 (t, J=6.0 Hz, 2H), 3.70-3.67 (m, 1H), 3.84 (t, J=6.0 Hz, 2H), 3.24-2.87 (m, 2H), 2.41-2.35 (m, 1H), 1.76-1.71 (m, 1H), 1.27-1.19 (m, 1H), 0.81 (d, J=7.0 Hz, 3H).

Example 15

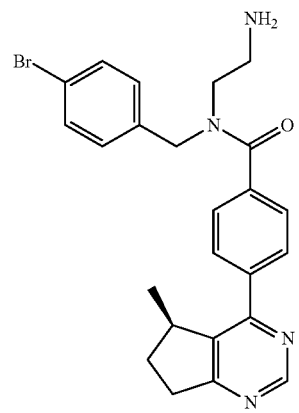

(R)—N-(2-aminoethyl)-N-(4-bromolbenzyl)-4-(5-methyl-6,7-dihydro-5H-cyclopenta[d]pyrimidin-4-yl)benzamide (R)—N-(2-Aminoethyl)-N-(4-bromolbenzyl)-4-(5-methyl-6,7-dihydro-5H-cyclopenta[d]pyrimidin-4-yl)benzamide was prepared in a similar manner as (R)—N-(2-aminoethyl)-N-(4-chlorobenzyl)-4-(5-methyl-6,7-dihydro-5H-cyclopenta[d]pyrimidin-4-yl)benzamide. MS (APCI+) [M+H]$^+$465.2. $^1$H NMR (D$_2$O, 500 MHz) δ 8.82 (s, 1H), 7.68 (d, J=8.5 Hz, 2H), 7.52 (d, J=8.5 Hz, 2H), 7.48 (d, J=8.0 Hz, 7.06 (d, J=8.0 Hz, 2H), 4.58 (s, 2H), 3.75 (t, J=6.5 Hz, 2H), 3.69-3.66 (m 1H), 3.22-2.78 (m, 4H), 2.37-2.29 (m, 1H), 1.71-1.67 (m, 1H), 1.22-1.37 (m, 2H), 0.75 (d, J=6.0 Hz, 3H).

Example 16

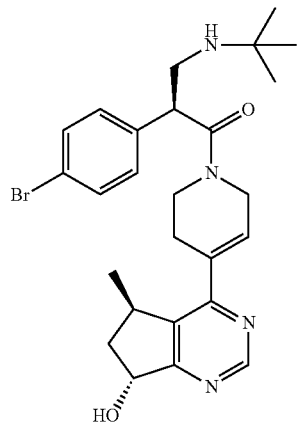

(S)-2-(4-bromophenyl)-3-(tert-butylamino)-1-(4-((5R,7R)-7-hydroxy-5-methyl-6,7-dihydro-5H-cyclopenta[d]pyrimidin-4-yl)-5,6-dihydropiperidin-1(2H)-yl)propan-1-one Step 1: A solution of Na$_2$CO$_3$ (2 mL, 2M) was added to a solution of (5R,7R)-4-chloro-5-methyl-6,7-dihydro-5H-cyclopenta[d]pyrimidin-7-yl 4-nitrobenzoate (334 mg, 1.00 mmol), 3,6-dihydro-2H-pyridine-1-tert-butoxycarbonyl-4-boronic acid, pinacol ester (340 mg, 1.10 mmol) in 1,4-dioxane (6 mL). The mixture was sparged with N$_2$ for 2 minutes. The catalyst Pd(dppf)Cl$_2$ (65 mg, 0.08 mmol) was added in one portion. The reaction vial was sealed and heated in microwave to 120° C. for 20 minutes. A solution of LiOH (0.7 mL, 3M) was added. The mixture was stirred at room temperature for 18 hours. Water (30 mL) was added to the mixture, extracted with DCM (3×20 mL). The combined organics were dried (Na$_2$SO$_4$), filtered and concentrated. The crude product was purified by flash chromatography (0-5% MeOH/DCM gradient elution) to give tert-butyl 4-((5R,7R)-7-hydroxy-5-methyl-6,7-dihydro-5H-cyclopenta[d]pyrimidin-4-yl)-5,6-dihydropyridine-1(2H)-carboxylate as an oil (221 mg, 67%). $^1$H NMR (CDCl$_3$, 400 MHz) δ 9.01 (s, 1H), 6.44 (s, 1H), 5.30 (m, 1H), 4.16-4.11 (m, 2H), 3.71-3.55 (m, 3H), 2.83-2.78 (m, 1H), 2.50-2.30 (m, 1H), 2.28-2.24 (m, 2H), 1.50 (s, 9H), 1.28-1.22 (m, 3H).

Step 2: TFA (193 ΞL, 2.5 mmol) was added to a solution of tert-butyl 4-((5R,7R)-7-hydroxy-5-methyl-6,7-dihydro-5H-cyclopenta[d]pyrimidin-4-yl)-5,6-dihydropyridine-1(2H)-carboxylate (33 mg, 0.10 mmol) in DCM (1 mL). The mixture was stirred at room temperature for 1 hour, and concentrated to give (5R,7R)-5-methyl-4-(1,2,3,6-tetrahydropyridin-4-yl)-6,7-dihydro-5H-cyclopenta[d]pyrimidin-7-ol as an oil, which was used further without purification.

Step 3: DIPEA (174 μL, 1.0 mmol) and O-(benzotriazol-1yl)-N,N,N',N'-tetramethyluronium hexafluorophosphate (42 mg, 0.11 mmol) were added to a solution of (5R,7R)-5-methyl-4-(1,2,3,6-tetrahydropyridin-4-yl)-6,7-dihydro-5H-cyclopenta[d]pyrimidin-7-ol (23 mg, 0.10 mmol) and (S)-2-(4-bromophenyl)-3-(tert-butylamino)propanoic acid (33 mg, 0.11 mmol) in DCM (1 mL). The mixture was stirred at room temperature for 1 hour. The reaction was quenched with saturated NH$_4$Cl, extracted with DCM (2×10 mL). The combined organics were dried (Na$_2$SO$_4$), filtered and concentrated. The crude product was purified by reverse phase HPLC to give (S)-2-(4-bromophenyl)-3-(tert-butylamino)-1-(4-((5R,7R)-7-hydroxy-5-methyl-6,7-dihydro-5H-cyclopenta[d]pyrimidin-4-yl)-5,6-dihydropiperidin-1(2H)-yl)propan-1-one ditrifluoroacetic acid as a solid (13 mg, 24%). MS (APCI+) [M+H]$^+$514.2. $^1$H NMR (D$_2$O, 400 MHz) 8.66 (s, 1H), 7.46 (d, J=8.4 Hz, 2H), 7.10 (J=8.4 Hz, 2H), 6.18-6.15 (m, 1H), 5.06-5.00 (m, 1H), 4.44-4.40 (m, 1H), 4.25-4.22 (m, 1H), 4.01-3.65 (m, 5H), 3.52-3.45 (m, 2H), 3.38-3.05 (m, 3H), 2.05-1.82 (m, 3H), 1.17 (s, 9H), 0.77 (d, J=7.2 Hz, 3H).

Example 17

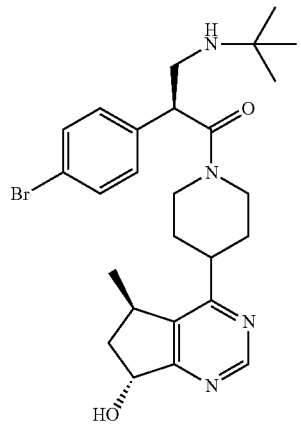

(S)-2-(4-bromophenyl)-3-(tert-butylamino)-1-(4-((5R,7R)-7-hydroxy-5-methyl-6,7-dihydro-5H-cyclopenta[d]pyrimidin-4-yl)piperidin-1-yl)propan-1-one Step 1: 5% Pd/C (10 mg) was added to a solution of tert-butyl 4-((5R,7R)-7-hydroxy-5-methyl-6,7-dihydro-5H-cyclopenta[d]pyrimidin-4-yl)-5,6-dihydropyridine-1(2H)-carboxylate (17 mg, 0.05 mmol) in EtOAc (1 mL). The mixture was stirred at room temperature under a hydrogen atmosphere overnight. The mixture was filtered through celite and concentrated to give tert-butyl 4-((5R,7R)-7-hydroxy-5-methyl-6,7-dihydro-5H-cyclopenta[d]pyrimidin-4-yl)piperidine-1-carboxylate as an oil (13 mg, 78%), which was used further without purification.

Step 2: TFA (77 μL, 1.0 mmol) was added to a solution of tert-butyl 4-((5R,7R)-7-hydroxy-5-methyl-6,7-dihydro-5H-cyclopenta[d]pyrimidin-4-yl)piperidine-1-carboxylate (13 mg, 0.04 mmol) in DCM (1 mL). The mixture was stirred at room temperature for 1 hour and concentrated to give (5R,7R)-5-methyl-4-(piperidin-4-yl)-6,7-dihydro-5H-cyclopenta[d]pyrimidin-7-ol as an oil, which was used further without purification.

Step 3: DIPEA (70.4, 0.40 mmol) and O-(benzotriazol-1yl)-N,N,N',N'-tetramethyluronium hexafluorophosphate (16 mg, 0.042 mmol) were added to a solution of (5R,7R)-5-methyl-4-(piperidin-4-yl)-6,7-dihydro-5H-cyclopenta[d]pyrimidin-7-ol (9.3 mg, 0.04 mmol) and (S)-2-(4-bromophenyl)-3-(tert-butylamino)propanoic acid (12 mg, 0.4 mmol) in DCM (1 mL). The mixture was stirred at room temperature for 1 hour. The reaction was quenched with sat. NH$_4$Cl and extracted with DCM (2×10 mL). The combined organics were dried (Na$_2$SO$_4$), filtered and concentrated. The crude product was purified by reverse phase HPLC to give (S)-2-(4-bromophenyl)-3-(tert-butylamino)-1-(4-((5R,7R)-7-hydroxy-5-methyl-6,7-dihydro-5H-cyclopenta[d]pyrimidin-4-yl)piperidin-1-yl)propan-1-one ditrifluoroacetic acid as a solid (4.6 mg, 22%). MS (APCI+) [M+H]$^+$516.2. $^1$H NMR (D$_2$O, 500 MHz) δ 8.85 (s, 1H), 7.68 (d, J=7.5 Hz, 2H), 7.34 (d, J=7.5 Hz, 2H), 5.33 (t, J=4.5 Hz, 1H), 4.64-4.59 (m, 1H), 4.38-4.34 (m, 1H), 3.97-3.89 (m, 1H), 3.70-3.47 (m, 2H), 3.38-3.13 (m, 3H), 2.91-2.82 (m, 2H), 2.35-2.29 (m, 1H), 2.14-2.07 (m, 1H), 1.94-1.77 (m, 2H), 1.58-1.47 (m, 1H), 1.40 (s, 9H), 1.18 (d, J=7.0 Hz, 3H).

Example 18

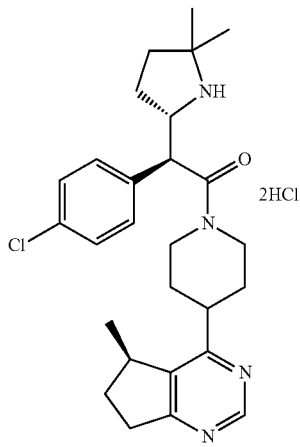

(S)-2-(4-chlorophenyl)-2-((S)-5,5-dimethylpyrrolidin-2-yl)-1-(4-((R)-5-methyl-6,7-dihydro-5H-cyclopenta[d]pyrimidin-4-yl)piperidin-1-yl)ethanone Step 1: A solution of Na₂CO₃ (0.36 mL, 2M) was added to a solution of (R)-4-chloro-5-methyl-6,7-dihydro-5H-cyclopenta[d]pyrimidine (101 mg, 0.60 mmol), 3,6-dihydro-2H-pyridine-1-tert-butoxycarbonyl-4-boronic acid, pinacol ester (204 mg, 0.66 mmol) in 1,4-dioxane (1.8 mL). The mixture was sparged with N₂ for 2 minutes. The catalyst Pd(PPh₃)₂Cl₂ (21 mg, 0.03 mmol) was added in one portion. The mixture was heated at 110° C. under N₂ for 8 hours. Water (20 mL) was added to the mixture and extracted with DCM (3×15 mL). The combined organics were dried (Na₂SO₄), filtered and concentrated. The crude product was purified by flash chromatography (first with 0-50% EtOAc/hexane, then with 0-4% MeOH/DCM gradient elution) to give (R)-tert-butyl 4-(5-methyl-6,7-dihydro-5H-cyclopenta[d]pyrimidin-4-yl)-5,6-dihydropyridine-1(2H)-carboxylate as an oil (127 mg, 67%). ¹H NMR (CDCl₃, 500 MHz) δ 8.91 (s, 1H), 6.31 (s, 1H), 3.64-3.55 (m, 1H), 3.10-3.03 (m, 2H), 2.98-2.90 (m, 2H), 2.83-2.78 (m, 1H), 2.42-2.34 (m, 2H), 1.77-1.69 (m, 2H).1.49 (s, 9H), 1.19 (d, J=7.0 Hz, 3H).

Step 2: 5% Pd/C (40 mg) was added to a solution of (R)-tert-butyl 4-(5-methyl-6,7-dihydro-5H-cyclopenta[d]pyrimidin-4-yl)-5,6-dihydropyridine-1(2H)-carboxylate (63 mg, 0.20 mmol) in EtOAc (4 mL). The mixture was stirred at room temperature under a hydrogen atmosphere overnight. The mixture was filtered through celite and concentrated to give (R)-tert-butyl 4-(5-methyl-6,7-dihydro-5H-cyclopenta[d]pyrimidin-4-yl)piperidine-1-carboxylate as an oil (58 mg, 91%), which was used further without purification.

Step 3: TFA (193 μL, 2.50 mmol) was added to a solution of (R)-tert-butyl 4-(5-methyl-6,7-dihydro-5H-cyclopenta[d]pyrimidin-4-yl)piperidine-1-carboxylate (32 mg, 0.10 mmol) in DCM (1 mL). The mixture was stirred at room temperature for 1 hour and concentrated to give (R)-5-methyl-4-(piperidin-4-yl)-6,7-dihydro-5H-cyclopenta[d]pyrimidine as an oil, which was used further without purification.

Step 4: DIPEA (174 μL, 1.00 mmol) and O-(benzotriazol-1yl)-N,N,N',N'-tetramethyluronium hexafluorophosphate (25 mg, 0.065 mmol) were added to a solution of (R)-5-methyl-4-(piperidin-4-yl)-6,7-dihydro-5H-cyclopenta[d]pyrimidine (22 mg, 0.10 mmol) and (S)-2-((S)-1-(tert-butoxycarbonyl)-5,5-dimethylpyrrolidin-2-yl)-2-(4-chlorophenyl) acetic acid (20 mg, 0.054 mmol) in DCM (2 mL). The mixture was stirred at room temperature for 2 hours. The reaction was quenched with saturated NH₄Cl and extracted with DCM (2×10 mL). The combined organics were dried (Na₂SO₄), filtered and concentrated. The crude product was purified by flash chromatography (0-5% MeOH/DCM gradient elution) to give (S)-tert-butyl 5-((S)-1-(4-chlorophenyl)-2-(4-((R)-5-methyl-6,7-dihydro-5H-cyclopenta[d]pyrimidin-4-yl)piperidin-1-yl)-2-oxoethyl)-2,2-dimethylpyrrolidine-1-carboxylate as a solid (26 mg, 84%). ¹H NMR (CD₃OD, 500 MHz) δ 8.73 (s, 3H), 7.42 (d, J=8.5 Hz, 2H), 7.25 (d, J=8.5 Hz, 2H), 4.73-4.70 (m, 2H), 4.40-4.35 (m, 1H), 3.89-3.86 (m, 1H), 3.76-3.70 (m, 2H), 3.49-3.43 (m, 1H), 3.25-3.20 (m, 2H), 3.18-2.97 (m, 2H), 2.86-2.70 (m, 3H), 2.34-2.25 (m, 1H), 2.16-2.13 (m, 1H), 1.83-1.67 (m, 2H), 1.54 (s, 9H), 1.38 (s, 3H), 1.36 (s, 3H), 1.25-1.20 (m, 3H).

Step 5: A solution of 4M HCl in 1,4-dioxane (0.344 mL) was added to a solution of (S)-tert-butyl 5-((S)-1-(4-chlorophenyl)-2-(4-((R)-5-methyl-6,7-dihydro-5H-cyclopenta[d]pyrimidin-4-yl)piperidin-1-yl)-2-oxoethyl)-2,2-dimethylpyrrolidine-1-carboxylate (26 mg, 0.046 mmol) in 1,4-dioxane (1 mL) at 0° C. The mixture was allowed to warm up and stirred at room temperature for 4 hours. The mixture was concentrated in vacuo. The resulting residue was dissolved in minimal DCM and added to the ether (5 mL) at 0° C. A solid precipitated. The mixture was decanted and dried in vacuo to give (S)-2-(4-chlorophenyl)-2-((S)-5,5-dimethylpyrrolidin-2-yl)-1-(4-((R)-5-methyl-6,7-dihydro-5H-cyclopenta[d]pyrimidin-4-yl)piperidin-1-yl)ethanone dihydrochloride as a solid (26 mg, 100%). MS (APCI+) [M+H]⁺467.3. ¹H NMR (D₂O, 500 MHz) δ 8.96 (s, 1H), 7.48 (d, J=8.5 Hz, 2H), 7.38 (d, J=8.5 Hz, 2H), 4.60-4.20 (m, 3H), 4.01-3.52 (m, 6H), 3.48-3.05 (m, 4H), 2.85-2.82 (m, 1H), 2.43-2.36 (m, 1H), 1.96-1.86 (m, 5H), 1.32 (s, 3H), 1.1.31 (s, 3H), 1.19 (d, J=7.5 Hz, 3H).

Example 19

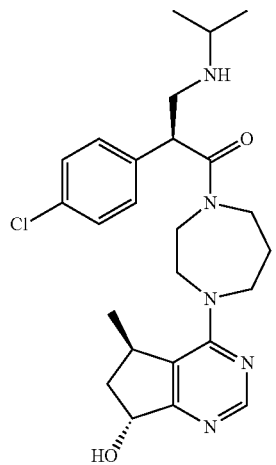

(S)-2-(4-chlorophenyl)-1-(4-((5R,7R)-7-hydroxy-5-methyl-6,7-dihydro-5H-cyclopenta[d]pyrimidin-4-yl)-1,4-diazepan-1-yl)-3-(isopropylamino)propan-1-one Step 1: (5R,7R)-4-Chloro-5-methyl-6,7-dihydro-5H-cyclopenta[d]pyrimidin-7-yl 4-nitrobenzoate (65 mg, 0.195 mmol) was dissolved in i-PrOH (5 mL), and then tert-butyl 1,4-diazepane-1-carboxylate (51 mg, 0.253 mmol) was added. N,N-Diisopropylethylamine (49 mg, 0.350 mmol) was added, and the reaction mixture was heated to 80° C. for 12 hours, after which the solvents were removed under reduced pressure. The resulting residue was taken up into EtOAc and then washed twice with water and once with brine. The organic portion was dried over magnesium sulfate, filtered, and then concentrated. The resulting residue was purified via silica gel chromatography to give tert-butyl 4-((5R,7R)-5-methyl-7-(4-nitrobenzoyloxy)-6,7-dihydro-5H-cyclopenta[d]pyrimidin-4-yl)azepane-1-carboxylate (78 mg, 81%). LCMS (APCI+) M+=498.1, Rt=3.81 min.

Step 2: tert-Butyl 4-((5R,7R)-5-methyl-7-(4-nitrobenzoyloxy)-6,7-dihydro-5H-cyclopenta[d]pyrimidin-4-yl) azepane-1-carboxylate (78 mg, 0.160 mmol) was dissolved in dichloromethane (2 mL) and then HCl (4M in dioxane, 0.58 mL) was added. The resulting mixture was stirred at ambient for 4 hours, at which time it was concentrated via rotary evaporation. The resulting (5R,7R)-4-(1,4-diazepan-1-yl)-5-methyl-6,7-dihydro-5H-cyclopenta[d]pyrimidin-7-yl 4-nitrobenzoate hydrochloride (64 mg, 94%) was used without further purification. LCMS (APCI+) M+H+=398.1, Rt=2.32 min.

Step 3: (5R,7R)-4-(1,4-Diazepan-1-yl)-5-methyl-6,7-dihydro-5H-cyclopenta[d]pyrimidin-7-yl 4-nitrobenzoate hydrochloride (61 mg, 0.140 mmol) and 3-(tert-butoxycarbonyl(isopropyl)amino)-2-(4-chlorophenyl)propanoic acid (48 mg, 0.140 mmol) were suspended in dichloromethane (5 mL) N,N-Diisopropylethylamine (54 mg, 0.420 mmol) was then added. HBTU (53 mg, 0.140 mmol) was added, and the resultant solution was stirred at ambient for 16 hours. After this time, the reaction mixture was quenched by the addition of saturated sodium carbonate solution and then extracted twice with dichloromethane. The combined organic portions were dried over sodium sulfate, filtered, and concentrated. The residue thus obtained was purified by silica gel chromatography to give (5R,7R)-4-(4-((S)-3-(tert-butoxycarbonyl(isopropyl)amino)-2-(4-chlorophenyl)propanoyl)-1,4-diazepan-1-yl)-5-methyl-6,7-dihydro-5H-cyclopenta[d]pyrimidin-7-yl 4-nitrobenzoate (50 mg, 50%). LCMS (APCI+) M+=721.1, Rt=4.51 min.

Step 4: (5R,7R)-4-(4-((S)-3-(tert-butoxycarbonyl(isopropyl)amino)-2-(4-chlorophenyl)propanoyl)-1,4-diazepan-1-yl)-5-methyl-6,7-dihydro-5H-cyclopenta[d]pyrimidin-7-yl 4-nitrobenzoate (50 mg, 0.069 mmol) was dissolved in a THF/water mixture (1:1, 2 mL), and then solid lithium hydroxide (6 mg, 0.139 mmol) was added. The resultant mixture was stirred at ambient for 16 hours, at which time it was diluted with EtOAc and then washed twice with saturated sodium bicarbonate solution. The organic layer was dried over magnesium sulfate, filtered and concentrated. The resulting residue was taken up in dichloromethane (5 mL), and then HCl (4M in dioxane, 0.25 mL) was added. The mixture was stirred for 16 hours, at which time solvents were removed via rotary evaporation. The resulting residue was dissolved in dichloromethane (1 mL) and then added to diethyl ether (50 mL). The resulting precipitate was collected by filtration and dried to give (S)-2-(4-chlorophenyl)-1-(4-((5R,7R)-7-hydroxy-5-methyl-6,7-dihydro-5H-cyclopenta[d]pyrimidin-4-yl)-1,4-diazepan-1-yl)-3-(isopropylamino)propan-1-one dihydrochloride (29 mg, 78%). LCMS (APCI+) M+=472.2, Rt=2.05 min.

Example 20

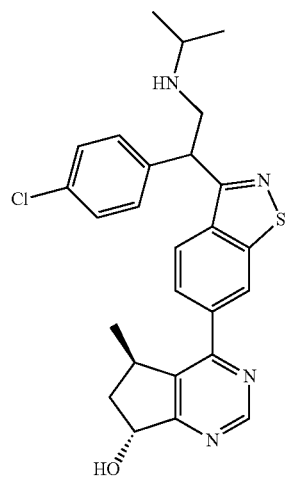

(5R,7R)-4-(3-(1-(4-chlorophenyl)-2-(isopropylamino)ethyl)benzo[d]isothiazol-6-yl-5-methyl-6,7-dihydro-5H-cyclopenta[d]pyrimidin-7-ol Step 1: Oxalyl chloride (3.7 mL, 42 mmol) was added dropwise to a solution of 3-bromothiophenol (5.00 g, 26.4 mmol) in ether (20 mL). The mixture was heated at reflux for 1.5 hours, cooled to room temperature, and concentrated in vacuo. The resulting residue was taken up in DCM (50 mL) and cooled to 0° C. Aluminum chloride (4.23 g, 31.7 mmol) was added in portions. The resultant mixture was stirred at reflux for 30 minutes, cooled to room temperature and poured into ice water with stirring. The organic layer was separated and successively washed with saturated aqueous NaHCO$_3$, water and brine. The organic layer was dried and concentrated in vacuo to give a solid, which was suspended in 20% EtOAc in hexanes (50 mL) and heated at reflux for 10 minutes. After cooling, the precipitated solid was collected by filtration to afford crude 6-bromobenzo[b]thiophene-2,3-dione (3.22 g, 50%). The 6-bromobenzo[b]thiophene-2,3-dione was added to ammonium hydroxide (35% aqueous solution, 40 mL) at 5-10° C., followed by dropwise addition of hydrogen peroxide (35% aqueous solution, 5.5 mL, 66 mmol). The resulting mixture was stirred at room temperature for 30 minutes, and then filtered to give 6-bromobenzo[b]thiophene-3-carboxamide (1.30 g, 38%) as a solid. $^1$H NMR (DMSO-d$_6$, 400 MHz) δ 8.66 (d, J=8.8 Hz, 1H), 8.62 (s, 1H), 8.23 (s, 1H), 7.81 (s, 1H), 7.73 (d, J=8.8 Hz, 1H).

Step 2: 10N NaOH solution (10 mL, 100 mmol) was added to a solution of 6-bromobenzo[b]thiophene-3-carboxamide (1.20 g, 4.67 mmol) in MeOH (80 mL). The mixture was heated at reflux overnight. After cooling, the mixture was acidified with 2N HCl. The resulting precipitate was filtered and dried to give 6-bromobenzo[d]isothiazole-3-carboxylic acid (1.10 g, 91%) as a solid. $^1$H NMR (DMSO-d$_6$, 400 MHz) δ 8.65 (s, 1H), 8.55 (d, J=8.8 Hz, 1H), 7.77 (d, J=8.8 Hz, 1H).

Step 3: DIEA (11.7 mL, 67.4 mmol) and HBTU (7.03 g, 18.5 mmol) were added to a solution of 6-bromobenzo[d]isothiazole-3-carboxylic acid (4.35 g, 16.9 mmol) and N,O- dimethylhydroxylamine hydrochloride (2.14 g, 21.9 mmol) in DMF (100 mL). The reaction was stirred at room temperature for 2 hours. The mixture was partitioned between water and EtOAc. The organic layer was washed with aqueous NaHCO₃ solution and brine, dried and concentrated. The residue was purified by column chromatography (hexane:EtOAc, 3:1) to give 6-bromo-N-methoxy-N-methylbenzo[d]isothiazole-3-carboxamide (4.60 g, 91%) as a solid. ¹H NMR (CDCl₃, 400 MHz) δ 8.12 (m, 2H), 8.59 (d, J=8.8 Hz, 1H), 3.83 (s, 3H), 3.49 (s, 3H).

Step 4: 4-Chlorophenyl magnesium bromide (1.0 N in THF, 16 mL, 16 mmol) was added to a stirred solution of 6-bromo-N-methoxy-N-methylbenzo[d]isothiazole-3-carboxamide (3.5 g, 12 mmol) in THF (100 mL). The reaction mixture was stirred at 0° C. for 1 hour. The reaction was poured into 1N HCl and extracted into ether. The combined organic layers were washed with brine, dried and concentrated. The crude product was suspended in ether and stirred for 15 minutes. The solid was collected by filtration to give (6-bromobenzo[d]isothiazol-3-yl)(4-chlorophenyl)methanone (3.3 g, 81%). ¹H NMR (CDCl₃, 400 MHz) δ 8.60 (d, J=8.8 Hz, 1H), 8.23 (d, J=8.4 Hz, 2H), 8.19 (s, 1H), 7.68 (d, J=8.8 Hz, 1H), 7.51 (d, J=8.4 Hz, 2H).

Step 5: A mixture of NaH (60% mineral oil dispersion, 0.060 g, 1.5 mmol) and DMSO (3 mL) was stirred at 70° C. for 45 minutes. The solution was then cooled with cold water, and methyltriphenylphosphonium bromide (0.58 g, 1.6 mmol) in DMSO (3 mL) was added dropwise. Stirring was continued for 15 minutes. 6-Bromobenzo[d]isothiazol-3-yl)(4-chlorophenyl)methanone (0.300 g, 0.850 mmol) was then added in a single portion. The mixture was stirred at room temperature for 1.5 hours and then poured into ice-water. The mixture was extracted with EtOAc. The combined organic layers were washed with brine, dried and concentrated. The resulting residue was purified by column chromatography (hexane:DCM, 10:1 to 6:1) to give 6-bromo-3-(1-(4-chlorophenyl)vinyl)benzo[d]isothiazole (0.26 g, 87%) as a solid. ¹H NMR (CDCl₃, 400 MHz) δ 8.22 (d, J=8.8 Hz, 1H), 8.12 (s, 1H), 7.51 (d, J=8.8 Hz, 1H), 7.30 (m, 4H), 5.97 (s, 1H), 5.81 (s, 1H).

Step 6: A mixture of 6-bromo-3-(1-(4-chlorophenyl)vinyl)benzo[d]isothiazole (600 mg, 1.71 mmol), DMF (3 mL) and allylamine (3 mL) was stirred at room temperature for 3 days. The reaction was partitioned between EtOAc and water. The organic phase was washed with brine, dried and concentrated. The residue was purified by column chromatography (DCM:MeOH, 20:1) to give N-(2-(6-bromobenzo[d]isothiazol-3-yl)-2-(4-chlorophenyl)ethyl)prop-2-en-1-amine (464 mg, 66%). ¹H NMR (CDCl₃, 400 MHz) δ 8.06 (d, J=1.6 Hz, 1H), 7.59 (d, J=8.8 Hz, 1H), 7.41 (dd, J=8.8 Hz, J=1.6 Hz, 1H), 7.25 (m, 4H), 5.86 (m, 1H), 5.16 (dd, J=17.2 Hz, J=1.6 Hz, 1H), 5.08 (d, J=10.4 Hz, 1H), 4.72 (t, J=7.2 Hz, 1H), 3.62 (dd, J=12.0 Hz, J=8.0 Hz, 1H), 3.31 (m, 2H), 3.20 (dd, J=12.0 Hz, J=6.8 Hz, 1H).

Step 7: A mixture of N-(2-(6-bromobenzo[d]isothiazol-3-yl)-2-(4-chlorophenyl)ethyl)prop-2-en-1-amine (0.441 g, 1.08 mmol), 1,3-dimethylpyrimidine-2,4,6(1H,3H,5H)-trione (0.507 g, 3.24 mmol), Pd(PPh₃)₄ (0.013 g, 0.011 mmol) and DCM (4 mL) was heated at 35° C. under N₂ for 4 hours. After cooling, DCM was evaporated. The resulting residue was taken up in ether, washed with saturated NaHCO₃ and brine, dried and concentrated. The crude product was dissolved in THF (8 mL). Boc₂O (0.28 g, 1.3 mmol) and Et₃N (0.23 mL, 1.6 mmol) were added. The mixture was stirred at room temperature for 1 hour. The solvent was evaporated, and the residue partitioned between EtOAc and water. The organic phase was separated and washed with brine, dried and concentrated. The resulting residue was purified by column chromatography (hexanes:EtOAc, 6:1) to give tert-butyl 2-(6-bromobenzo[d]isothiazol-3-yl)-2-(4-chlorophenyl) ethylcarbamate (0.39 g, 77%) as a solid. LCMS (APCI+) m/z 467, 469 [M+H]+; Rt=3.71 min.

Step 8: Bis(pinacolato)diboron (0.25 g, 1.0 mmol), tert-butyl 2-(6-bromobenzo[d]isothiazol-3-yl)-2-(4-chlorophenyl)ethylcarbamate (0.39 g, 0.83 mmol) and potassium acetate (0.25 g, 2.5 mmol) were added to DMF (4 mL). The reaction solution was deoxygenated and then dichloro[1,1'-bis(diphenylphosphino)-ferrocene]palladium(II) dichloromethane adduct (34 mg, 0.042 mmol) was added. The mixture was heated to 80° C. for 4 hours. The mixture was cooled to room temperature and partitioned between EtOAc and water. The aqueous phase was extracted with EtOAc. The combined organic layers were washed with brine, dried and concentrated. The resulting residue was purified by column chromatography (hexanes:EtOAc, 8:1) to give tert-butyl 2-(4-chlorophenyl)-2-(6-(4,4,5,5-tetramethyl-1,3,2-dioxaborolan-2-yl)benzo[d]isothiazol-3-yl)ethylcarbamate (0.36 g, 84%) as a solid. LCMS (APCI+) m/z 515, 517 [M+H]+; Rt=4.96 min.

Step 9: DMF (3 mL) and 2M aqueous Na₂CO₃ (0.38 mL, 0.76 mmol) were added to a nitrogen flushed flask containing tert-butyl 2-(4-chlorophenyl)-2-(6-(4,4,5,5-tetramethyl-1,3,2-dioxaborolan-2-yl)benzo[d]isothiazol-3-yl)ethylcarbamate (150 mg, 0.291 mmol), (5R,7R)-4-chloro-5-methyl-6,7-dihydro-5H-cyclopenta[d]pyrimidin-7-yl 4-nitrobenzoate (117 mg, 0.350 mmol) and dichloro[1,1'-bis(diphenylphosphino)-ferrocene]palladium(II) dichloromethane adduct (12 mg, 0.015 mmol). The mixture was heated at 80° C. for 1 hour. The mixture was cooled to room temperature and partitioned between EtOAc and water. The combined organic layers were washed with saturated aqueous NaHCO₃ and brine, dried and concentrated. The residue was purified by flash chromatography on silica gel, eluting with hexanes:EtOAc (4:1 to 1:1) to give (5R,7R)-4-(3-(2-(tert-butoxycarbonylamino)-1-(4-chlorophenyl)ethyl)benzo[d]isothiazol-6-yl)-5-methyl-6,7-dihydro-5H-cyclopenta[d]pyrimidin-7-yl 4-nitrobenzoate (102 mg, 51%) as an oil. LCMS (APCI+) m/z 630, 632 [M+H]+; Rt=4.68 min.

Step 10: 1 N LiOH aqueous solution (0.30 mL, 0.30 mmol) was added to a stirred solution of (5R,7R)-4-(3-(2-(tert-butoxycarbonylamino)-1-(4-chlorophenyl)ethyl)benzo[d]isothiazol-6-yl)-5-methyl-6,7-dihydro-5H-cyclopenta[d]pyrimidin-7-yl 4-nitrobenzoate (102 mg, 0.149 mmol) in THF (3 mL). The reaction mixture was stirred at room temperature overnight. The solvent was evaporated. The resulting residue was partitioned between EtOAc and water. The aqueous layer was extracted with EtOAc. The combined organic layers were washed with brine, dried and concentrated. The resulting residue was purified by column chromatography (DCM:MeOH, 60:1) to give tert-butyl 2-(4-chlorophenyl)-2-(6-((5R,7R)-7-hydroxy-5-methyl-6,7-dihydro-5H-cyclopenta[d]pyrimidin-4-yl)benzo[d]isothiazol-3-yl)ethylcarbamate (62 mg, 78%) as an oil. LCMS (APCI+) m/z 537, 539 [M+H]+; Rt=3.99 min.

Step 11: A solution of tert-butyl 2-(4-chlorophenyl)-2-(6-((5R,7R)-7-hydroxy-5-methyl-6,7-dihydro-5H-cyclopenta[d]pyrimidin-4-yl)benzo[d]isothiazol-3-yl)ethylcarbamate (41 mg, 0.076 mmol) in DCM was treated with 4N HCl in dioxane (0.5 mL). The reaction was stirred at room temperature overnight. The reaction was concentrated and triturated with ether (twice) to yield (5R,7R)-4-(3-(2-amino-1-(4-chlorophenyl)ethyl)benzo[d]isothiazol-6-yl)-5-methyl-6,7-dihydro-5H-cyclopenta[d]pyrimidin-7-ol trihydrochloride (32 mg, 77%). LCMS (APCI+) m/z 437, 439 [M+H]+; Rt=2.48 min.

Step 12: DIEA (0.035 mL, 0.20 mmol) was added to a stirred suspension of (5R,7R)-4-(3-(2-amino-1-(4-chlorophenyl)ethyl)benzo[d]isothiazol-6-yl)-5-methyl-6,7-dihydro-5H-cyclopenta[d]pyrimidin-7-ol trihydrochloride (22 mg, 0.050 mmol) in DCE (1.5 mL). The suspension was shaken until dissolved. A solution of acetone (0.022 mL, 0.30 mmol) in THF (0.3 mL) was added. The reaction was allowed to stir at room temperature for 15 minutes, at which point Na(OAc)$_3$BH (27 mg, 0.13 mmol) was added. The reaction was allowed to stir at room temperature for 1 hour. The reaction mixture was diluted with DCM, washed with saturated aqueous NaHCO$_3$ solution and brine, dried and concentrated. The resulting residue was purified by column chromatography (DCM:7N ammonia in MeOH, 30:1) to give the free base, which was taken up in DCM and acidified with 2N HCl in ether. Removal of the solvents under reduced pressure gave (5R,7R)-4-(3-(1-(4-chlorophenyl)-2-(isopropylamino)ethyl)benzo[d]isothiazol-6-yl)-5-methyl-6,7-dihydro-5H-cyclopenta[d]pyrimidin-7-ol trihydrochloride. LCMS (APCI+) m/z 479, 481 [M+H]+; Rt=2.69 min.

While the invention has been described in conjunction with the enumerated embodiments, it will be understood that they are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound of Formula I:

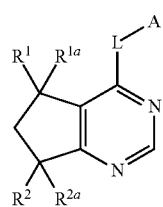

or a stereoisomer or pharmaceutically acceptable salt thereof, wherein:
  $R^1$ and $R^{1a}$ are independently selected from hydrogen, methyl, ethyl, —CH=CH$_2$, —CH$_2$OH, CF$_3$, CHF$_2$ or CH$_2$F;
  $R^2$ is selected from hydrogen, OH, OCH$_3$ or F;
  $R^{2a}$ is selected from hydrogen, methyl or F, or
  $R^2$ and $R^{2a}$ are oxo;

L is selected from:

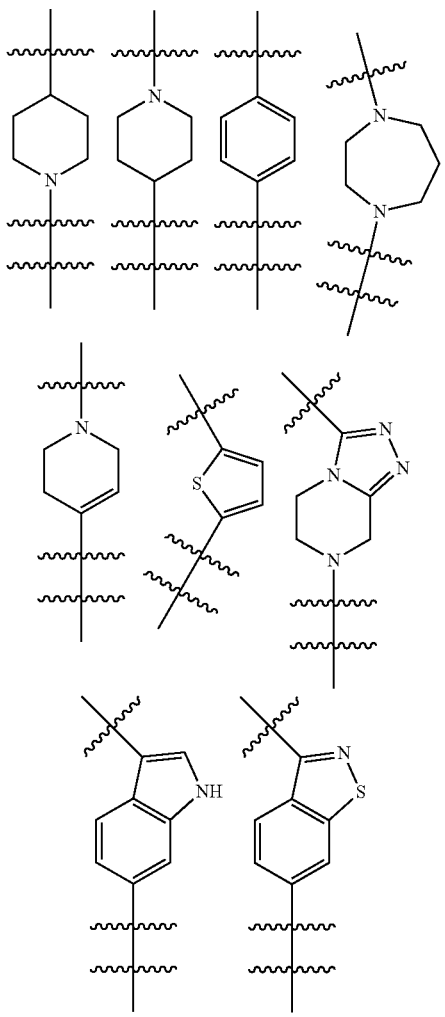

wherein the single wavy line is where L attaches to A and the double wavy line is where L attaches to the pyrimidine;
  A is:

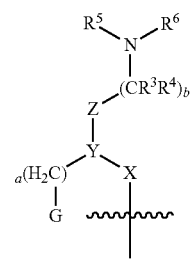

X is a direct bond from L to Y, CH$_2$, O, C=O, NH or C(=O)NH;
  Y is CH or N;
  Z is absent, CH$_2$ or O, wherein L, X, Y, Z and b are selected so that any nitrogen is not bonded directly to another nitrogen;
  G is phenyl optionally substituted with one to four $R^a$ groups or a 5-6 membered heteroaryl optionally substituted by a halogen;

$R^3$ and $R^4$ are independently selected from hydrogen or methyl;

$R^5$ and $R^6$ are independently selected from hydrogen or $C_1$-$C_4$ alkyl;

a is 0 or 1;

b is 0, 1 or 2; and each $R^a$ is independently halogen, $C_1$-$C_6$-alkyl, $C_3$-$C_6$-cycloalkyl, —O—($C_1$-$C_6$-alkyl), $CF_3$, —$OCF_3$, S($C_1$-$C_6$-alkyl), CN, —$OCH_2$-phenyl, $NH_2$, —$NO_2$, —NH—($C_1$—$C_6$-alkyl), —N—($C_1$—$C_6$-alkyl)$_2$, piperidine, pyrrolidine, $CH_2F$, $CHF_2$, —$OCH_2F$, —$OCHF_2$, —OH, —$SO_2$($C_1$-$C_6$-alkyl), C(O)$NH_2$, C(O)NH($C_1$-$C_6$-alkyl), and C(O)N($C_1$-$C_6$-alkyl)$_2$; or b is 1, $R^3$ is hydrogen and $R^4$ and $R^5$ together with the atoms to which they are attached form an optionally substituted 5-6 membered heterocyclic ring having one ring nitrogen atom, and $R^6$ is selected from the group consisting of H or $C_1$-$C_4$ alkyl optionally substituted with OH or O($C_1$-$C_3$ alkyl), such that A has the structure:

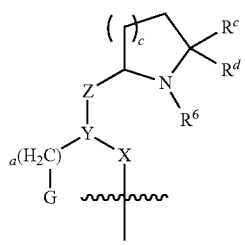

$R^c$ and $R^d$ are independently selected from hydrogen and methyl; and c is 1 or 2; or b is 1, Z is $CH_2$ and $R^5$ and Y together with the atoms to which they are attached form an optionally substituted 6 membered heterocyclic ring having one ring nitrogen atom, and $R^6$ is selected from the group consisting of hydrogen or $C_1$-$C_4$ alkyl optionally substituted with OH or O($C_1$-$C_3$ alkyl), such that A has the structure:

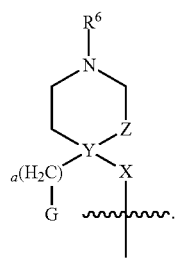

2. A compound of claim 1, wherein Formula I is selected from:

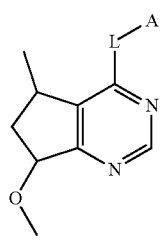 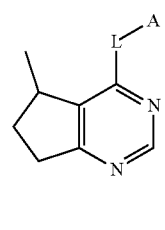 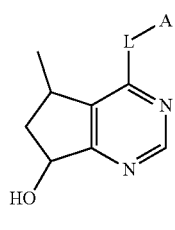

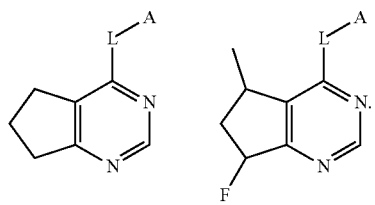

3. A compound of claim 2, wherein Formula I is selected from:

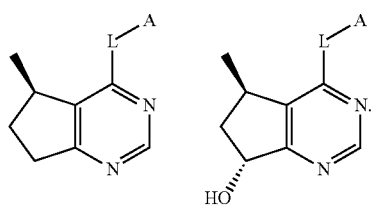

4. A compound as claimed in claim 1, wherein L is:

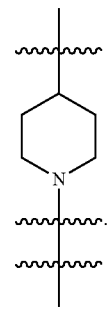

5. A compound as claimed in claim 1, wherein L is:

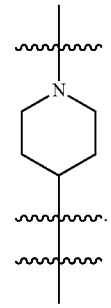

6. A compound as claimed in claim 1, wherein L is:

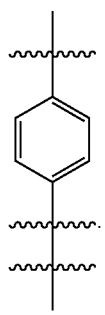

7. A compound as claimed in claim 1, wherein L is:

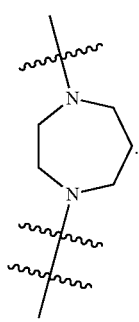

8. A compound as claimed in claim 1, wherein L is:

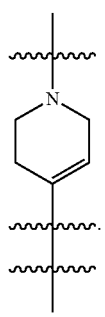

9. A compound as claimed in claim 1, wherein L is:

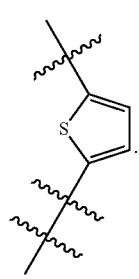

10. A compound as claimed in claim 1, wherein L is:

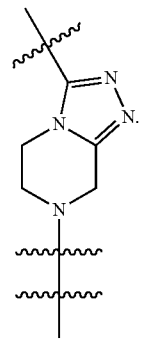

11. A compound as claimed in claim 1, wherein L is:

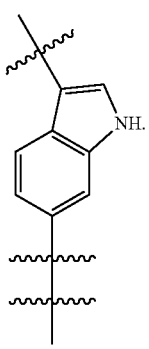

12. A compound as claimed in claim 1, wherein L is:

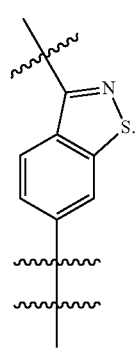

13. A compound as claimed in claim 1, wherein X is a direct bond from L to Y, Y is CH and Z is O.

14. A compound as claimed in claim 1, wherein X is C(=O)NH, Y is CH and Z is absent.

15. A compound as claimed in claim 1, wherein X is a direct bond from L to Y, Y is CH and Z is absent.

16. A compound as claimed in claim 1, wherein X is NH, Y is CH and Z is absent.

17. A compound as claimed in claim 1, wherein X is C=O, Y is N, Z is absent and b is 1 or 2.

18. A compound as claimed in claim 1, wherein X is C=O, Y is CH and Z is absent.

19. A compound as claimed in claim 1, wherein $R^3$ is hydrogen.

20. A compound as claimed in claim 1, wherein $R^3$ is methyl.

21. A compound as claimed in claim 1, wherein $R^4$ is hydrogen.

22. A compound as claimed in claim 1, wherein $R^4$ is methyl.

23. A compound as claimed in claim 1, wherein $R^5$ is hydrogen.

24. A compound as claimed in claim 1, wherein $R^5$ is $C_1$-$C_4$ alkyl.

25. A compound of claim 24, wherein $R^5$ is selected from methyl, isopropyl and tert-butyl.

26. A compound as claimed in claim 1, wherein $R^6$ is hydrogen.

27. A compound as claimed in claim 1, wherein $R^6$ is methyl.

28. A compound as claimed in claim 1, wherein b is 1, $R^3$ is hydrogen and $R^4$ and $R^5$ together with the atoms to which they are attached form an optionally substituted 5-6 membered heterocyclic ring having one ring nitrogen atom, such that A has the structure A8:

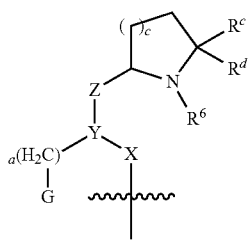

A8 wherein c is 1 or 2;

$R^c$ and $R^d$ are independently selected from hydrogen and methyl; and $R^6$ is selected from the group consisting of H or $C_1$-$C_4$ alkyl optionally substituted with OH or O($C_1$-$C_3$ alkyl).

29. A compound of claim 28, wherein c is 1.

30. A compound as claimed in claim 1, wherein b is 1, Z is $CH_2$ and $R^5$ and Y together with the atoms to which they are attached form an optionally substituted 6 membered heterocyclic ring having one ring nitrogen atom, and $R^6$ is selected from the group consisting of hydrogen or $C_1$-$C_4$ alkyl optionally substituted with OH or O($C_1$-$C_3$ alkyl), such that A has the structure A9:

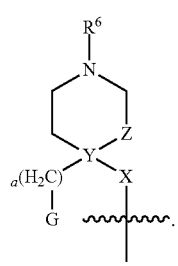

A9

31. A compound as claimed in claim 1, wherein G is selected from the group consisting of 4-chlorophenyl, 4-bromophenyl, 4-trifluoromethylphenyl and 2,4-dichlorophenyl.

32. A compound of Formula I as defined in claim 1 which is:

(5R,7R)-4-(4-((S)-(4-chlorophenyl)(2-(dimethylamino)ethoxy)methyl)piperidin-1-yl)-5-methyl-6,7-dihydro-5H-cyclopenta[d]pyrimidin-7-ol;

(5R,7R)-4-(4-((R)-(4-chlorophenyl)(2-(dimethylamino)ethoxy)methyl)piperidin-1-yl)-5-methyl-6,7-dihydro-5H-cyclopenta[d]pyrimidin-7-ol;

N—((S)-1-amino-3-(2,4-dichlorophenyl)propan-2-yl)-5-((R)-5-methyl-6,7-dihydro-5H -cyclopenta[d]pyrimidin-4-yl)thiophene-2-carboxamide;

N—((S)-1-amino-3-(2,4-dichlorophenyl)propan-2-yl)-5-((5R,7R)-7-hydroxy-5-methyl-6,7-dihydro-5H-cyclopenta[d]pyrimidin-4-yl)thiophene-2-carboxamide;

(5R,7R)-4-(4-(4-(4-chlorophenyl)piperidin-4-yl)phenyl)-5-methyl-6,7-dihydro-5H-cyclopenta[d]pyrimidin-7-ol;

N—((R)-2-(4-chlorophenyl)-2-(6-((R)-5-methyl-6,7-dihydro-5H-cyclopenta[d]pyrimidin-4-yl)-1H-indol-3-yl)ethyl)propan-2-amine;

(R)—N-(2-(4-chlorophenyl)-2-(4-(5-methyl-6,7-dihydro-5H-cyclopenta[d]pyrimidin-4-yl)phenoxy)ethyl)propan-2-amine;

(5R,7R)-4-(3-(Amino(4-chlorophenyl)methyl)-5,6-dihydro-[1,2,4]triazolo[4,3-a]pyrazin-7(8H)-yl)-5-methyl-6,7-dihydro-5H-cyclopenta[d]pyrimidin-7-ol;

(5R,7R)-4-(3-(1-(4-Chlorophenyl)-2-(isopropylamino)ethyl)-5,6-dihydro-[1,2,4]triazolo[4,3-a]pyrazin-7(8H)-yl)-5-methyl-6,7-dihydro-5H-1-cyclopenta[d]pyrimidin-7-ol;

(4-Chlorophenyl)(7-((R)-5-methyl-6,7-dihydro-5H-cyclopenta[d]pyrimidin-4-yl)-5,6,7,8-tetrahydro-[1,2,4]triazolo[4,3-a]pyrazin-3-yl)methanamine;

(5R,7R)-4-(3-((R)-1-Amino-2-(4-chlorophenyl)ethyl)-5,6-dihydro-[1,2,4]triazolo[4,3-a]pyrazin-7(8H)-yl)-5-methyl-6,7-dihydro-5H-cyclopenta[d]pyrimidin-7-ol;

(5R,7R)-4-(4-(1-(4-Chlorophenyl)-2-(isopropylamino)ethylamino)phenyl)-5-methyl-6,7-dihydro-5H-cyclopenta[d]pyrimidin-7-ol hydrochloride;

(R)—N-(2-aminoethyl)-N-(4-chlorobenzyl)-4-(5-methyl-6,7-dihydro-5H-cyclopenta[d]pyrimidin-4-yl)benzamide;

(R)—N-(2-aminoethyl)-N-(4-trifluoromethylbenzyl)-4-(5-methyl-6,7-dihydro-5H-cyclopenta[d]pyrimidin-4-yl)benzamide;

(R)—N-(2-aminoethyl)-N-(4-bromolbenzyl)-4-(5-methyl-6,7-dihydro-5H-cyclopenta[d]pyrimidin-4-yl)benzamide;

(S)-2-(4-bromophenyl)-3-(tert-butylamino)-1-(4-((5R,7R)-7-hydroxy-5-methyl-6,7-dihydro-5H-cyclopenta[d]pyrimidin-4-yl)-5,6-dihydropiperidin-1(2H)-yl)propan-1-one;

(S)-2-(4-bromophenyl)-3-(tert-butylamino)-1-(4-((5R,7R)-7-hydroxy-5-methyl-6,7-dihydro-5H-cyclopenta[d]pyrimidin-4-yl)piperidin-1-yl)propan-1-one;

(S)-2-(4-chlorophenyl)-2-((S)-5,5-dimethylpyrrolidin-2-yl)-1-(4-((R)-5-methyl-6,7-dihydro-5H-cyclopenta[d]pyrimidin-4-yl)piperidin-1-yl)ethanone;

(S)-2-(4-chlorophenyl)-1-(4-((5R,7R)-7-hydroxy-5-methyl-6,7-dihydro-5H-cyclopenta[d]pyrimidin-4-yl)-1,4-diazepan-1-yl)-3-(isopropylamino)propan-1-one;

or (5R,7R)-4-(3-(1-(4-chlorophenyl)-2-(isopropylamino)ethyl)benzo[d]isothiazol-6-yl)-5-methyl-6,7-dihydro-5H-cyclopenta[d]pyrimidin-7-ol, or a pharmaceutically acceptable salt thereof.

33. A pharmaceutical composition, comprising a compound as claimed in claim 1, and a pharmaceutically acceptable carrier or excipient.

* * * * *